US007514210B2

(12) United States Patent
Holliger et al.

(10) Patent No.: US 7,514,210 B2
(45) Date of Patent: Apr. 7, 2009

(54) COMPARTMENTALISED SELF REPLICATION METHOD FOR IN VITRO EVOLUTION OF MOLECULAR LIBRARIES

(75) Inventors: Phillipp Holliger, Cambridge (GB); Farid Ghadassy, Cambridge (GB); Jennifer Lee Ong, Cambridge (GB)

(73) Assignee: Medical Research Council, London (GB)

( * ) Notice: Subject to any disclaimer, the term of this patent is extended or adjusted under 35 U.S.C. 154(b) by 821 days.

(21) Appl. No.: 10/387,387

(22) Filed: Mar. 13, 2003

(65) Prior Publication Data

US 2004/0005594 A1 Jan. 8, 2004

Related U.S. Application Data

(63) Continuation of application No. PCT/GB01/04108, filed on Sep. 13, 2001.

(60) Provisional application No. 60/285,501, filed on Apr. 20, 2001, provisional application No. 60/283,771, filed on Apr. 13, 2001.

(30) Foreign Application Priority Data

Sep. 13, 2000 (GB) ................................. 0022458.4

(51) Int. Cl.
*C12Q 1/68* (2006.01)
*C12P 19/34* (2006.01)
*C12N 15/00* (2006.01)
*C12N 15/74* (2006.01)
*C12N 1/21* (2006.01)
*C07H 21/00* (2006.01)

(52) U.S. Cl. .......................... 435/6; 435/91.1; 435/91.2; 435/91.5; 435/91.52; 435/194; 435/440; 435/252.33; 435/471; 536/23.2

(58) Field of Classification Search ................ 435/91.2, 435/91.31, 91.5, 91.52, 194, 440; 536/23.1, 536/23.2
See application file for complete search history.

(56) References Cited

U.S. PATENT DOCUMENTS 5,290,479 A    3/1994   Clark ......................... 252/351

FOREIGN PATENT DOCUMENTS

| EP | 1482036 A2 | 12/2004 |
|---|---|---|
| WO | WO 94/26766 | 11/1994 |
| WO | WO 96/40723 | 12/1996 |
| WO | WO 97/47763 | 12/1997 |
| WO | WO 98/13502 | 4/1998 |
| WO | WO 98/23733 | 6/1998 |
| WO | WO 98/34120 | 8/1998 |
| WO | WO 99/02671 | 1/1999 |
| WO | WO 00/04139 | 1/2000 |
| WO | WO 00/40712 | 7/2000 |

OTHER PUBLICATIONS

Seffernick et al., J. Bacteriol. 183(8):2405-2410, 2001.*
Witkowski et al., Biochemistry 38:11643-11650, 1999.*
Branden et al., Introduction to Protein Structure, Garland Publishing Inc., New York, p. 247, 1991.*
Patel et al., PNAS 97(10):5095-5100, May 2000.*
Ghadassy, F.J. et al., (2001), "Directed evolution of polymerase function by compartmentalized self-replication", *PNAS*, 98(8): 4552-4557.
Pelletier, J.N. et al., (1999), "An in vivo library-versus-library selection of optimized protein-protein interactions", *Nature Biotechnology*, 17: 683-690.
Anarbaev, R.O. et al., (1998), "Klenow fragment and DNA polymerase α-primase fromserva calf thymus in water-in-oil microemulsions", *Biochimica et Biophysica Acta*, 1384: 315-324.
Tawfik, D.S. et al., (1998), "Man-made cell-like compartments for molecular evolution", *Nature Biotechnology*, 16: 652-656.
Suzuki, M. et al., (1996), "Random mutagenesis of *Thermus aquaticus* DNA polymerase I: Concordance of immutable sites in vivo with the crystal structure", *Proc. Natl. Acad. Sci. USA*, 93: 9670-9675.
Vainshtein, I. et al., (1996), "Peptide rescue of an N-terminal truncation of the Stoffel fragment of *Taq* DNA polymerase", *Protein Science*, 5: 1785-1792.
Oberholzer, T. et al., (1995), "Polymerase chain reaction in liposomes", *Chemistry & Biology*, 2: 677-682.
Eigen, M. et al., (1991), "The Hypercycle. Coupling of RNA and Protein Biosynthesis in the Infection Cycle of an RNA Bacteriophage", *Biochemistry*, 30(46): 11005-11018.
Eigen, M. et al., (1980), "Hypercycles and Compartments. Compartments Assists—but do not replace—Hypercyclic Organization of Early Genetic Information", *J. Theor. Biol.*, 85: 407-411.
Eigen, M., (1976), "Wie entsteht Information? Prinzipien der Selbstorganisation in der Biologie", *Berichte der Bunsen-Gesellschaft Fur Physikalische Chemie*, 80(11): 1059-1081.
International Search Report of International Application No. PCT/GB01/04108.

(Continued)

*Primary Examiner*—Delia M Ramirez
(74) *Attorney, Agent, or Firm*—Edwards Angell Palmer & Dodge LLP; Kathleen Williams

(57) ABSTRACT

We describe a method of selecting an enzyme having replicase activity, the method comprising the steps of: (a) providing a pool of nucleic acids comprising members each encoding a replicase or a variant of the replicase; (b) subdividing the pool of nucleic acids into compartments, such that each compartment comprises a nucleic acid member of the pool together with the replicase or variant encoded by the nucleic acid member; (c) allowing nucleic acid replication to occur; and (d) detecting amplification of the nucleic acid member by the replicase. Methods for selecting agents capable of modulating replicase activity, and for selecting interacting polypeptides are also disclosed.

20 Claims, 9 Drawing Sheets

OTHER PUBLICATIONS

Walde, et al., "Oparin's Reactions Revisited: Enzymatic Synthesis of Poly (adenylic acid) in Micelles and Self-Reproducing Vesicles", Journal of the American Chemical Society (1994), V. 116, No. 7, pp. 7541-7547.

The European Search Report (EP04078077).

Dove, Simon L. et al., Conversion of the omega subunit of *Escherichia coli* RNA polymerase into a transcriptional activator or an activation target, Genes & Development, 12: 745-754, 1998.

Marsolier, Marie-Claude et al., A RNA polymerase III-based two-hybrid system to study RNA polymerase II transcriptional regulators, Journal of Molecular Biology, 268: 243-249, 1997.

Yamada, Yasushi et al., Increased Activity of Chromo bacterium viscosum Lipase in Aerosol OT Reverse Micelles in the Presence of Nonionic Surfactants, Biotechnology Progress, 9:468-472, 1993.

\* cited by examiner

SEQUENCE LISTING

<160> NUMBER OF SEQ ID NOS: 28

<210> SEQ ID NO 1
<211> LENGTH: 62
<212> TYPE: DNA
<213> ORGANISM: Artificial
<220> FEATURE:
<221> NAME/KEY: misc_feature
<222> LOCATION: (1)..(62)
<223> OTHER INFORMATION: Synthetic PCR primer for the amplification of
      Taq polymerase-encoding DNA and for the introduction of
      restriction sites for cloning.

<400> SEQUENCE: 1
ggcgactcta gataacgagg gcaaaaaatg cgtggtatgc ttcctctttt tgagcccaag       60
gg                                                                    62

<210> SEQ ID NO 2
<211> LENGTH: 43
<212> TYPE: DNA
<213> ORGANISM: Artificial
<220> FEATURE:
<221> NAME/KEY: misc_feature
<222> LOCATION: (1)..(43)
<223> OTHER INFORMATION: Synthetic PCR primer for the amplification of
      Taq polymerase-encoding DNA and for the introduction of
      restriction sites for cloning.

<400> SEQUENCE: 2
gcggtgcgga gtcgactcac tccttggcgg agagccagtc ctc                        43

<210> SEQ ID NO 3
<211> LENGTH: 23
<212> TYPE: DNA
<213> ORGANISM: Artificial
<220> FEATURE:
<221> NAME/KEY: misc_feature
<222> LOCATION: (1)..(23)
<223> OTHER INFORMATION: Synthetic PCR primer used in screening for
      inserts and mutations when cloning Taq polymerase DNA.

<400> SEQUENCE: 3
aaaaatctag ataacgaggg caa                                              23

<210> SEQ ID NO 4
<211> LENGTH: 28
<212> TYPE: DNA
<213> ORGANISM: Artificial
<220> FEATURE:
<221> NAME/KEY: misc_feature
<222> LOCATION: (1)..(28)
<223> OTHER INFORMATION: Synthetic PCR primer used in screening for
      inserts and mutations when cloning Taq polymerase DNA.

<400> SEQUENCE: 4
accaccgaac tgcgggtgac gccaagcg                                         28

<210> SEQ ID NO 5
<211> LENGTH: 25
<212> TYPE: DNA
<213> ORGANISM: Artificial
<220> FEATURE:
<221> NAME/KEY: misc_feature
<222> LOCATION: (1)..(25)
<223> OTHER INFORMATION: Synthetic PCR primer used to screen amplified
      Taq polymerase sequences for mutation.

```
<400> SEQUENCE: 5
gggtacgtgg agaccctctt cggcc                                          25

<210> SEQ ID NO 6
<211> LENGTH: 17
<212> TYPE: DNA
<213> ORGANISM: Artificial
<220> FEATURE:
<221> NAME/KEY: misc_feature
<222> LOCATION: (1)..(17)
<223> OTHER INFORMATION: Synthetic PCR primer used in error-prone PCR
      mutagenesis of Taq polymerase DNA.

<400> SEQUENCE: 6
gtaaaacgac ggccagt                                                   17

<210> SEQ ID NO 7
<211> LENGTH: 17
<212> TYPE: DNA
<213> ORGANISM: Artificial
<220> FEATURE:
<221> NAME/KEY: misc_feature
<222> LOCATION: (1)..(17)
<223> OTHER INFORMATION: Synthetic PCR primer used in error-prone PCR
      mutagenesis of Taq polymerase DNA.

<400> SEQUENCE: 7
caggaaacag ctatgac                                                   17

<210> SEQ ID NO 8
<211> LENGTH: 40
<212> TYPE: DNA
<213> ORGANISM: Artificial
<220> FEATURE:
<221> NAME/KEY: misc_feature
<222> LOCATION: (1)..(40)
<223> OTHER INFORMATION: Synthetic PCR primer used in error-prone PCR
      mutagenesis of Taq polymerase DNA.

<400> SEQUENCE: 8
caggaaacag ctatgacaaa aatctagata acgagggcaa                          40

<210> SEQ ID NO 9
<211> LENGTH: 45
<212> TYPE: DNA
<213> ORGANISM: Artificial
<220> FEATURE:
<221> NAME/KEY: misc_feature
<222> LOCATION: (1)..(45)
<223> OTHER INFORMATION: Synthetic PCR primer used in error-prone PCR
      mutagenesis of Taq polymerase DNA.

<400> SEQUENCE: 9
gtaaaacgac ggccagtacc accgaactgc gggtgacgcc aagcg                    45

<210> SEQ ID NO 10
<211> LENGTH: 38
<212> TYPE: DNA
<213> ORGANISM: Artificial
<220> FEATURE:
<221> NAME/KEY: misc_feature
<222> LOCATION: (1)..(38)
<223> OTHER INFORMATION: Synthetic PCR primer that introduces a 3'
      purine-purine mismatch (A-G  mismatch)

<400> SEQUENCE: 10
caggaaacag ctatgacaaa aatctagata acgaggga                            38
```

```
<210> SEQ ID NO 11
<211> LENGTH: 45
<212> TYPE: DNA
<213> ORGANISM: Artificial
<220> FEATURE:
<221> NAME/KEY: misc_feature
<222> LOCATION: (1)..(45)
<223> OTHER INFORMATION: Synthetic PCR primer that introduces a 3'
      pyrimidine-pyrimidine mismatch (C-C  mismatch)

<400> SEQUENCE: 11
gtaaaacgac ggccagtacc accgaactgc gggtgacgcc aagcc            45

<210> SEQ ID NO 12
<211> LENGTH: 26
<212> TYPE: DNA
<213> ORGANISM: Artificial
<220> FEATURE:
<221> NAME/KEY: misc_feature
<222> LOCATION: (1)..(26)
<223> OTHER INFORMATION: Synthetic oligonucleotide primer used in 3SR.

<400> SEQUENCE: 12
ggagtagatg cttgcttttc tgagcc                                  26

<210> SEQ ID NO 13
<211> LENGTH: 28
<212> TYPE: DNA
<213> ORGANISM: Artificial
<220> FEATURE:
<221> NAME/KEY: misc_feature
<222> LOCATION: (1)..(28)
<223> OTHER INFORMATION: Synthetic oligonucleotide used for PCR/3SR
      amplification of Taq polymerase mutants.

<400> SEQUENCE: 13
gctctggtta tctgcatcat cgtctgcc                                28

<210> SEQ ID NO 14
<211> LENGTH: 2500
<212> TYPE: DNA
<213> ORGANISM: Artificial
<220> FEATURE:
<221> NAME/KEY: misc_feature
<222> LOCATION: (1)..(2500)
<223> OTHER INFORMATION: Mutant of Taq polymerase.

<400> SEQUENCE: 14
aaccttggta tgcttcctct ttttgagccc aagggtcgcg tcctcctggt ggacggccac    60
cacctggcct accgcacctt ccacgccctg aagggcctca ccaccagccg ggggagccg    120 gtgcaggcgg tctacggctt cgccaagagc ctcctcaagg ccctcaagga ggacggggac   180
gcggtgatcg tggtctttga cgccaaggcc ccctcctccc gccacgaggc ctacgggggg   240
tacaaggcgg ccgggccc cacgccggag gactttcccc ggcaactcgc cctcatcaag    300
gagctggtgg acctcctggg gctggcgcgc ctcgaggtcc cgggctacga ggcggacgac   360
gtcctggcca gctggccaa gaaggcggaa aaggagggct acgaggtccg catcctcacc   420
gccgacaaag accttttacca gctccttttcc gaccgcatcc acgtcctcca ccccgagggg   480
tacctcatca cccccggcctg gctttgggaa agtacggggg tgaggcccga ccagtgggcc   540
gactaccggg ccctgaccgg ggacgagtcc gacaaccttc ccgggtgcaa gggcatcggg   600
gagaagacgg cgaagaagct tctgaggagg tgggggagcc tggaagccct cctcgagaac   660
ctggaccggc tgaagcccgc catccggag aagatcctgg cccacacgga cgatctgaag   720
```

```
ctctcctggg acctggccaa ggtgcgcacc gacctgcccc tggaggtgga cttcgccaaa      780 aggcggggagc ccgaccggga gaggcttagg gcctttctgg agaggcttga gtttggcagc     840
ctcctccacg agttcggcct tctggaaagc cccaaggccc tggaggaggc cccctggccc     900
ccgccggaag gggccttcgt gggctttgtg ctttcccgca aggagcccat gtgggccgat     960
cttctggccc tggccgccgc caggggggc cgggtccacc gggcccccga gccttataaa     1020
gccctcaggg acttgaagga ggcgcggggg cttctcgcca agacctgag cgttctggcc     1080 ctaagggaag gccttggcct cccgccggc gacgacccca tgctcctcgc ctacctcctg     1140
gacccttcca acaccacccc cgagggggtg gcccggcgct acggcgggga gtggacggag     1200
gaggcggggg agcgggccgc cctttccgag aggctcttcg ccaacctgtg ggggaggctt     1260 gaggggggagg agaggctcct ttggctttac cgggaggtgg agaggcccct ttccgctgtc     1320
ctggcccaca tggaggccac ggggtgcgc ctggacgtgg cctatctcag gccttgtcc     1380 ctggaggtgg ccgaggagat cgcccgcctc gaggccgagg tcttccgcct ggccggccac     1440
cccttcaacc tcaactcccg ggaccagctg gaaagggtcc tctttgacga gctagggctt     1500
cccgccatcg gcaagacgga aagaccggc aagcgctcca ccagcgccgc cgtcctggag     1560
gccctccgcg aggcccaccc catcgtggag aagatcctgc agtaccggga gctcaccaag     1620
ctgaagagca cctacattga ccccttgccg gacctcatcc accccaggac gggccgcctc     1680
cacacccgct tcaaccagac ggccacggcc acgggcaggc taagtagctc cgatcccaac     1740
ctccagaaca tccccgtccg caccccgctt ggcagagga tccgcggggc cttcatcgcc     1800
gaggaggggt ggctattggt ggtcctggac tatagccaga tagagctcag ggtgctggcc     1860
cacctctccg cgacgagaa cctgatccgg gtcttcagg aggggcggga catccacacg     1920
gaaaccgcca gctggatgtt cggcgtcccc cgggaggccg tggacccct gatgcgccgg     1980 gcggccaaga ccatcaactt cggggttctc tacggcatgt cggcccaccg cctctcccag     2040
gagctagcca tcccttacga ggaggcccag gccttcattg agcgctactt tcagagcttc     2100
cccaaggtgc gggcctggat tgagaagacc ctggaggag gcaggaggcg ggggtacgtg     2160
gagaccctct tcggccgtcg ccgctacgtg ccagacctag aggcccgggt gaagagcgtg     2220
cgggaggcgg ccgagcgcat ggccttcaac atgcccgtcc agggcaccgc cgccgacctc     2280
atgaagctgg ctatggtgaa gctcttcccc aggctggagg aaatggggc caggatgctc     2340 cttcaggtcc acgacgagct ggtcctcgag gccccaaaag agagggcgga ggccgtggcc     2400
cggctggcca aggaggtcat ggagggggtg tatccctgg ccgtgccct ggaggtggag     2460 gtggggatag gggaggactg gctctctgcc aaggagtgag                          2500
```

<210> SEQ ID NO 15
<211> LENGTH: 829
<212> TYPE: PRT
<213> ORGANISM: Artificial
<220> FEATURE:
<221> NAME/KEY: MISC_FEATURE
<222> LOCATION: (1)..(829)
<223> OTHER INFORMATION: Mutant of Taq polymerase.

<400> SEQUENCE: 15

```
Met Leu Pro Leu Phe Glu Pro Lys Gly Arg Val Leu Leu Val Asp Gly
 1               5                  10                  15

His His Leu Ala Tyr Arg Thr Phe His Ala Leu Lys Gly Leu Thr Thr
            20                  25                  30
```

-continued

```
Ser Arg Gly Glu Pro Val Gln Ala Val Tyr Gly Phe Ala Lys Ser Leu
        35                  40                  45

Leu Lys Ala Leu Lys Glu Asp Gly Asp Ala Val Ile Val Val Phe Asp
        50                  55                  60

Ala Lys Ala Pro Ser Ser Arg His Glu Ala Tyr Gly Gly Tyr Lys Ala
65                  70                  75                  80

Gly Arg Ala Pro Thr Pro Glu Asp Phe Pro Arg Gln Leu Ala Leu Ile
                85                  90                  95

Lys Glu Leu Val Asp Leu Leu Gly Leu Ala Arg Leu Glu Val Pro Gly
                100                 105                 110

Tyr Glu Ala Asp Asp Val Leu Ala Ser Leu Ala Lys Lys Ala Glu Lys
            115                 120                 125

Glu Gly Tyr Glu Val Arg Ile Leu Thr Ala Asp Lys Asp Leu Tyr Gln
        130                 135                 140

Leu Leu Ser Asp Arg Ile His Val Leu His Pro Glu Gly Tyr Leu Ile
145                 150                 155                 160

Thr Pro Ala Trp Leu Trp Glu Lys Tyr Gly Leu Arg Pro Asp Gln Trp
                165                 170                 175

Ala Asp Tyr Arg Ala Leu Thr Gly Asp Glu Ser Asp Asn Leu Pro Gly
            180                 185                 190

Val Lys Gly Ile Gly Glu Lys Thr Ala Lys Lys Leu Leu Glu Glu Trp
        195                 200                 205

Gly Ser Leu Glu Ala Leu Leu Glu Asn Leu Asp Arg Leu Lys Pro Ala
        210                 215                 220

Ile Arg Glu Lys Ile Leu Ala His Thr Asp Asp Leu Lys Leu Ser Trp
225                 230                 235                 240

Asp Leu Ala Lys Val Arg Thr Asp Leu Pro Leu Glu Val Asp Phe Ala
                245                 250                 255

Lys Arg Arg Glu Pro Asp Arg Glu Arg Leu Arg Ala Phe Leu Glu Arg
            260                 265                 270

Leu Glu Phe Gly Ser Leu Leu His Glu Phe Gly Leu Leu Glu Ser Pro
        275                 280                 285

Lys Ala Leu Glu Glu Ala Pro Trp Pro Pro Glu Gly Ala Phe Val
        290                 295                 300

Gly Phe Val Leu Ser Arg Lys Glu Pro Met Trp Ala Asp Leu Leu Ala
305                 310                 315                 320

Leu Ala Ala Ala Arg Gly Gly Arg Val His Arg Ala Pro Glu Pro Tyr
                325                 330                 335

Lys Ala Leu Arg Asp Leu Lys Glu Ala Arg Gly Leu Leu Ala Lys Asp
            340                 345                 350

Leu Ser Val Leu Ala Leu Arg Glu Gly Leu Gly Leu Pro Pro Gly Asp
        355                 360                 365

Asp Pro Met Leu Leu Ala Tyr Leu Leu Asp Pro Ser Asn Thr Thr Pro
370                 375                 380

Glu Gly Val Ala Arg Arg Tyr Gly Gly Glu Trp Thr Glu Glu Ala Gly
385                 390                 395                 400

Glu Arg Ala Ala Leu Ser Glu Arg Leu Phe Ala Asn Leu Trp Gly Arg
                405                 410                 415

Leu Glu Gly Glu Glu Arg Leu Leu Trp Leu Tyr Arg Glu Val Glu Arg
            420                 425                 430

Pro Leu Ser Ala Val Leu Ala His Met Glu Ala Thr Gly Val Arg Leu
        435                 440                 445

Asp Val Ala Tyr Leu Arg Ala Leu Ser Leu Glu Val Ala Glu Glu Ile
```

```
                450             455             460
Ala Arg Leu Glu Ala Glu Val Phe Arg Leu Ala Gly His Pro Phe Asn
465             470             475             480

Leu Asn Ser Arg Asp Gln Leu Glu Arg Val Leu Phe Asp Glu Leu Gly
            485             490             495

Leu Pro Ala Ile Gly Lys Thr Glu Lys Thr Gly Lys Arg Ser Thr Ser
            500             505             510

Ala Ala Val Leu Glu Ala Leu Arg Glu Ala His Pro Ile Val Glu Lys
            515             520             525

Ile Leu Gln Tyr Arg Glu Leu Thr Lys Leu Lys Ser Thr Tyr Ile Asp
530             535             540

Pro Leu Pro Asp Leu Ile His Pro Arg Thr Gly Arg Leu His Thr Arg
545             550             555             560

Phe Asn Gln Thr Ala Thr Ala Thr Gly Arg Leu Ser Ser Ser Asp Pro
            565             570             575

Asn Leu Gln Asn Ile Pro Val Arg Thr Pro Leu Gly Gln Arg Ile Arg
            580             585             590

Arg Ala Phe Ile Ala Glu Glu Gly Trp Leu Leu Val Val Leu Asp Tyr
            595             600             605

Ser Gln Ile Glu Leu Arg Val Leu Ala His Leu Ser Gly Asp Glu Asn
610             615             620

Leu Ile Arg Val Phe Gln Glu Gly Arg Asp Ile His Thr Glu Thr Ala
625             630             635             640

Ser Trp Met Phe Gly Val Pro Arg Glu Ala Val Asp Pro Leu Met Arg
            645             650             655

Arg Ala Ala Lys Thr Ile Asn Phe Gly Val Leu Tyr Gly Met Ser Ala
            660             665             670

His Arg Leu Ser Gln Glu Leu Ala Ile Pro Tyr Glu Glu Ala Gln Ala
            675             680             685

Phe Ile Glu Arg Tyr Phe Gln Ser Phe Pro Lys Val Arg Ala Trp Ile
            690             695             700

Glu Lys Thr Leu Glu Glu Gly Arg Arg Arg Gly Tyr Val Glu Thr Leu
705             710             715             720

Phe Gly Arg Arg Arg Tyr Val Pro Asp Leu Glu Ala Arg Val Lys Ser
            725             730             735

Val Arg Glu Ala Ala Glu Arg Met Ala Phe Asn Met Pro Val Gln Gly
            740             745             750

Thr Ala Ala Asp Leu Met Lys Leu Ala Met Val Lys Leu Phe Pro Arg
            755             760             765

Leu Glu Glu Met Gly Ala Arg Met Leu Leu Gln Val His Asp Glu Leu
            770             775             780

Val Leu Glu Ala Pro Lys Glu Arg Ala Glu Ala Val Ala Arg Leu Ala
785             790             795             800

Lys Glu Val Met Glu Gly Val Tyr Pro Leu Ala Val Pro Leu Glu Val
            805             810             815

Glu Val Gly Ile Gly Glu Asp Trp Leu Ser Ala Lys Glu
            820             825

<210> SEQ ID NO 16
<211> LENGTH: 2553
<212> TYPE: DNA
<213> ORGANISM: Artificial
<220> FEATURE:
<221> NAME/KEY: misc_feature
<222> LOCATION: (2552)..(2553)
```

<223> OTHER INFORMATION: "n" can be any of g, a, t and c.
<220> FEATURE:
<221> NAME/KEY: misc_feature
<222> LOCATION: (1)..(2553)
<223> OTHER INFORMATION: Mutant of Taq polymerase.

<400> SEQUENCE: 16

| | | | | |
|---|---|---|---|---|
| gatgctccct | cttttgagc | ccaagggtcg | cgtcctcctg | gtggacggcc | accacctggc | 60 |
| ctaccgcacc | ttccacgccc | tgaagggcct | caccaccagc | cgggggagc | cggtgcaggc | 120 |
| ggtctacggc | ttcgccaaga | gcctcctcaa | ggccctcaag | gaggacgggg | acgcggtgat | 180 |
| cgtggtcttt | gacgccaagg | cccctcctt | ccgccacgag | gcctacgggg | ggtacaaggc | 240 |
| gggccgggcc | cccacgccgg | aggactttcc | ccggcaactc | gccctcatca | aggagctggt | 300 |
| ggacctcctg | gggctggcgc | gcctcgaggt | cccgggctac | gaggcggacg | acgtcctggc | 360 |
| cagcctggcc | aagaaggcgg | aaaaggaggg | ctacgaggtc | cgcatcctca | ccgccgacaa | 420 |
| agaccttac | cagctccttt | ccgaccgcat | ccacgtcctc | caccccgagg | ggtacctcat | 480 |
| caccccggcc | tggctttggg | aaaagtacgg | cctgaggccc | gaccagtggg | ccgactaccg | 540 |
| ggccctgacc | ggggacgagt | ccgacaacct | tcccggggtc | aagggcatcg | gggagaagac | 600 |
| ggcgaggaag | cttctggagg | agtggggag | cctggaagcc | ctcctcaaga | acctggaccg | 660 |
| gctgaagccc | gccatccggg | agaagatcct | ggcccacatg | gacgatctga | agctctcctg | 720 |
| ggacctggcc | aaggtgcgca | ccgacctgcc | cctggaggtg | gacttcgcca | aaaggcggga | 780 |
| gcccgaccgg | gagaggcttg | gccttttctg | gagaggcttg | agcttggcag | cctcctccac | 840 |
| gagttcggcc | ttctggaaag | ccccaaggcc | ctggaggagg | cctcctggcc | ccgccggaa | 900 |
| ggggccttcg | tgggctttgt | gctttcccgc | aaggagccca | tgtgggccga | tcttctggcc | 960 |
| ctggccgccg | caggggggg | ccgggtccac | cgggcccccg | agccttataa | agccctcaga | 1020 |
| gacctgaagg | aggcgcgggg | gcttctcgcc | aaagacctga | gcgttctggc | cctgagggaa | 1080 |
| ggccttggcc | tcccgcccgg | cgacgacccc | atgctcctcg | cctacctcct | ggacccttcc | 1140 |
| aacaccaccc | ccgaggggt | ggccccggcg | tacggcgggg | agtggacgga | ggaggcgggg | 1200 |
| gagcgggccg | cccttttccga | gaggctcttc | gccaacctgt | ggggaggct | tgaggggag | 1260 |
| gagaggctcc | tttggctta | ccgggaggtg | gagaggcccc | ttttccgctgt | cctgccccac | 1320 |
| atggaggcca | cgggggtgcg | cctggacgtg | gcctatctca | gggccttgtc | cctggaggtg | 1380 |
| gccgaggaga | tcgcccgcct | cgaggccgag | gtcttccgcc | tggccggcca | cccccttcaac | 1440 |
| ctcaactccc | gagaccagct | ggaaagggtc | tctttgacg | agctagggct | tcccgccatc | 1500 |
| ggcaagacgg | agaagaccgg | caagcgctcc | accagcgccg | ccgtcctgga | ggccctccgc | 1560 |
| gaggcccacc | ccatcgtgga | aagatcctg | cagtaccggg | agctcaccaa | gctgaagagc | 1620 |
| acctacattg | accccttgcc | ggacctcatc | cacccagga | cgggccgcct | ccacaccgc | 1680 |
| ttcaaccaga | cggccacggc | cacgggcagg | ctaagtagct | ccgatcccaa | cctccagaac | 1740 |
| atcccgtcc | gcaccccgct | tgggcagagg | atccgccggg | ccttcatcgc | cgaggagggg | 1800 |
| tggctattgg | tggccctgga | ctatagccag | atagagctca | ggtgctggc | ccacctctcc | 1860 |
| ggcgacgaga | acctgatccg | ggtcttccag | gaggggcggg | acatccacac | ggagaccgcc | 1920 |
| agctggatgt | tcgcgtccc | ccgggaggcc | gtggaccccc | tgatgcgccg | gcggccaag | 1980 |
| accatcaact | tcggggtcct | ctacggcatg | tcggccaccg | cctctcccag | gagctagcca | 2040 |
| tcccttacga | ggaggcccag | gccttcattg | agcgctactt | tcagagcttc | cccaaggtgc | 2100 |
| gggcctggat | tgagaagacc | ctggaggagg | gcaggaggcg | ggggtacgtg | gagacccctct | 2160 |

```
tcggccgccg ccgctacgtg ccagacctag aggcccgggt gaagagcgtg cgggaggcgg    2220
ccgagcgcat ggccttcaac atgcccgtcc agggcaccgc cgccgacctc atgaagctgg    2280
ctatggtgaa gctcttcccc aggctggagg aaatggggc caggatgctc cttcaggtcc     2340
acgacgagct ggtcctcgag gccccaaaag agagggcgga ggccgtggcc cggctggcca    2400
aggaggtcat ggaggggtg tatcccctgg ccgtgcccct ggaggtggag gtggggatag      2460
gggaggactg gctctccgcc aaggagggag tcgacctgca ggcagcgctt ggcgtcaccc    2520
gcagttcggt ggtactggcc gtcgttttac ann                                 2553
```

<210> SEQ ID NO 17
<211> LENGTH: 829
<212> TYPE: PRT
<213> ORGANISM: Artificial
<220> FEATURE:
<221> NAME/KEY: MISC_FEATURE
<222> LOCATION: (1)..(829)
<223> OTHER INFORMATION: Mutant of Taq polymerase.

<400> SEQUENCE: 17

```
Met Leu Pro Leu Phe Glu Pro Lys Gly Arg Val Leu Leu Val Asp Gly
1               5                   10                  15

His His Leu Ala Tyr Arg Thr Phe His Ala Leu Lys Gly Leu Thr Thr
            20                  25                  30

Ser Arg Gly Glu Pro Val Gln Ala Val Tyr Gly Phe Ala Lys Ser Leu
        35                  40                  45

Leu Lys Ala Leu Lys Glu Asp Gly Asp Ala Val Ile Val Val Phe Asp
    50                  55                  60

Ala Lys Ala Pro Ser Phe Arg His Glu Ala Tyr Gly Gly Tyr Lys Ala
65                  70                  75                  80

Gly Arg Ala Pro Thr Pro Glu Asp Phe Pro Arg Gln Leu Ala Leu Ile
                85                  90                  95

Lys Glu Leu Val Asp Leu Leu Gly Leu Ala Arg Leu Glu Val Pro Gly
            100                 105                 110

Tyr Glu Ala Asp Asp Val Leu Ala Ser Leu Ala Lys Lys Ala Glu Lys
        115                 120                 125

Glu Gly Tyr Glu Val Arg Ile Leu Thr Ala Asp Lys Asp Leu Tyr Gln
    130                 135                 140

Leu Leu Ser Asp Arg Ile His Val Leu His Pro Glu Gly Tyr Leu Ile
145                 150                 155                 160

Thr Pro Ala Trp Leu Trp Glu Lys Tyr Gly Leu Arg Pro Asp Gln Trp
                165                 170                 175

Ala Asp Tyr Arg Ala Leu Thr Gly Asp Glu Ser Asp Asn Leu Pro Gly
            180                 185                 190

Val Lys Gly Ile Gly Glu Lys Thr Ala Arg Lys Leu Leu Glu Glu Trp
        195                 200                 205

Gly Ser Leu Glu Ala Leu Leu Lys Asn Leu Asp Arg Leu Lys Pro Ala
    210                 215                 220

Ile Arg Glu Lys Ile Leu Ala His Met Asp Asp Leu Lys Leu Ser Trp
225                 230                 235                 240

Asp Leu Ala Lys Val Arg Thr Asp Leu Pro Leu Glu Val Asp Phe Ala
                245                 250                 255

Lys Arg Arg Glu Pro Asp Arg Glu Arg Leu Arg Ala Phe Leu Glu Arg
            260                 265                 270

Leu Glu Leu Gly Ser Leu Leu His Glu Phe Gly Leu Leu Glu Ser Pro
```

```
                275                 280                 285
Lys Ala Leu Glu Glu Ala Ser Trp Pro Pro Glu Gly Ala Phe Val
290                 295                 300
Gly Phe Val Leu Ser Arg Lys Glu Pro Met Trp Ala Asp Leu Leu Ala
305                 310                 315                 320
Leu Ala Ala Arg Gly Gly Arg Val His Arg Ala Pro Glu Pro Tyr
            325                 330                 335
Lys Ala Leu Arg Asp Leu Lys Glu Ala Arg Gly Leu Leu Ala Lys Asp
                340                 345                 350
Leu Ser Val Leu Ala Leu Arg Glu Gly Leu Gly Leu Pro Pro Gly Asp
                355                 360                 365
Asp Pro Met Leu Leu Ala Tyr Leu Leu Asp Pro Ser Asn Thr Thr Pro
370                 375                 380
Glu Gly Val Ala Arg Arg Tyr Gly Gly Glu Trp Thr Glu Glu Ala Gly
385                 390                 395                 400
Glu Arg Ala Ala Leu Ser Glu Arg Leu Phe Ala Asn Leu Trp Gly Arg
                405                 410                 415
Leu Glu Gly Glu Glu Arg Leu Leu Trp Leu Tyr Arg Glu Val Glu Arg
                420                 425                 430
Pro Leu Ser Ala Val Leu Ala His Met Glu Ala Thr Gly Val Arg Leu
                435                 440                 445
Asp Val Ala Tyr Leu Arg Ala Leu Ser Leu Glu Val Ala Glu Glu Ile
            450                 455                 460
Ala Arg Leu Glu Ala Glu Val Phe Arg Leu Ala Gly His Pro Phe Asn
465                 470                 475                 480
Leu Asn Ser Arg Asp Gln Leu Glu Arg Val Leu Phe Asp Glu Leu Gly
                485                 490                 495
Leu Pro Ala Ile Gly Lys Thr Glu Lys Thr Gly Lys Arg Ser Thr Ser
                500                 505                 510
Ala Ala Val Leu Glu Ala Leu Arg Glu Ala His Pro Ile Val Glu Lys
                515                 520                 525
Ile Leu Gln Tyr Arg Glu Leu Thr Lys Leu Lys Ser Thr Tyr Ile Asp
530                 535                 540
Pro Leu Pro Asp Leu Ile His Pro Arg Thr Gly Arg Leu His Thr Arg
545                 550                 555                 560
Phe Asn Gln Thr Ala Thr Ala Thr Gly Arg Leu Ser Ser Ser Asp Pro
            565                 570                 575
Asn Leu Gln Asn Ile Pro Val Arg Thr Pro Leu Gly Gln Arg Ile Arg
                580                 585                 590
Arg Ala Phe Ile Ala Glu Glu Gly Trp Leu Leu Val Ala Leu Asp Tyr
            595                 600                 605
Ser Gln Ile Glu Leu Arg Val Leu Ala His Leu Ser Gly Asp Glu Asn
            610                 615                 620
Leu Ile Arg Val Phe Gln Glu Gly Arg Asp Ile His Thr Glu Thr Ala
625                 630                 635                 640
Ser Trp Met Phe Gly Val Pro Arg Glu Ala Val Asp Pro Leu Met Arg
                645                 650                 655
Arg Ala Ala Lys Thr Ile Asn Phe Gly Val Leu Tyr Gly Met Ser Ala
                660                 665                 670
His Arg Leu Ser Gln Glu Leu Ala Ile Pro Tyr Glu Glu Ala Gln Ala
            675                 680                 685
Phe Ile Glu Arg Tyr Phe Gln Ser Phe Pro Lys Val Arg Ala Trp Ile
690                 695                 700
```

```
Glu Lys Thr Leu Glu Glu Gly Arg Arg Gly Tyr Val Glu Thr Leu
705                 710                 715                 720

Phe Gly Arg Arg Arg Tyr Val Pro Asp Leu Glu Ala Arg Val Lys Ser
            725                 730                 735

Val Arg Glu Ala Ala Glu Arg Met Ala Phe Asn Met Pro Val Gln Gly
            740                 745                 750

Thr Ala Ala Asp Leu Met Lys Leu Ala Met Val Lys Leu Phe Pro Arg
            755                 760                 765

Leu Glu Glu Met Gly Ala Arg Met Leu Leu Gln Val His Asp Glu Leu
            770                 775                 780

Val Leu Glu Ala Pro Lys Glu Arg Ala Glu Ala Val Ala Arg Leu Ala
785                 790                 795                 800

Lys Glu Val Met Glu Gly Val Tyr Pro Leu Ala Val Pro Leu Glu Val
                805                 810                 815

Glu Val Gly Ile Gly Glu Asp Trp Leu Ser Ala Lys Glu
            820                 825

<210> SEQ ID NO 18
<211> LENGTH: 829
<212> TYPE: PRT
<213> ORGANISM: Artificial
<220> FEATURE:
<221> NAME/KEY: MISC_FEATURE
<222> LOCATION: (1)..(829)
<223> OTHER INFORMATION: Mutant of Taq polymerase.

<400> SEQUENCE: 18

Met Leu Pro Leu Phe Glu Pro Lys Gly Arg Val Leu Leu Val Asp Gly
1               5                   10                  15

His His Leu Ala Tyr Arg Thr Phe His Ala Leu Lys Gly Leu Thr Thr
            20                  25                  30

Ser Arg Gly Glu Pro Val Gln Ala Val Tyr Gly Phe Ala Lys Ser Leu
        35                  40                  45

Leu Lys Ala Leu Lys Glu Asp Gly Asp Ala Val Ile Val Val Phe Asp
50                  55                  60

Ala Lys Ala Pro Ser Phe Arg His Glu Ala Tyr Gly Gly Tyr Lys Ala
65                  70                  75                  80

Gly Arg Ala Pro Thr Pro Glu Asp Phe Pro Arg Gln Leu Ala Leu Ile
            85                  90                  95

Lys Glu Leu Val Asp Leu Leu Gly Leu Ala Arg Leu Glu Val Pro Gly
            100                 105                 110

Tyr Glu Ala Asp Asp Val Leu Ala Ser Leu Ala Lys Lys Ala Glu Lys
            115                 120                 125

Glu Gly Tyr Glu Val Arg Ile Leu Thr Ala Asp Lys Asp Leu Tyr Gln
130                 135                 140

Leu Leu Ser Asp Arg Ile His Val Leu His Pro Glu Gly Tyr Leu Ile
145                 150                 155                 160

Thr Pro Ala Trp Leu Trp Glu Lys Tyr Gly Leu Arg Pro Asp Gln Trp
            165                 170                 175

Ala Asp Tyr Arg Ala Leu Thr Gly Asp Glu Ser Asp Asn Leu Pro Gly
            180                 185                 190

Val Lys Gly Ile Gly Glu Lys Thr Ala Lys Lys Leu Leu Glu Glu Trp
            195                 200                 205

Gly Ser Leu Glu Ala Leu Leu Glu Asn Leu Asp Arg Leu Lys Pro Ala
210                 215                 220
```

-continued

```
Ile Arg Glu Lys Ile Leu Ala His Thr Asp Asp Leu Lys Leu Ser Trp
225                 230                 235                 240

Asp Leu Ala Lys Val Arg Thr Asp Leu Pro Leu Glu Val Asp Phe Ala
            245                 250                 255

Lys Arg Arg Glu Pro Asp Arg Glu Arg Leu Arg Ala Phe Leu Glu Arg
            260                 265                 270

Leu Glu Phe Gly Ser Leu Leu His Glu Phe Gly Leu Leu Glu Ser Pro
            275                 280                 285

Lys Ala Leu Glu Glu Ala Pro Trp Pro Pro Glu Gly Ala Phe Val
290                 295                 300

Gly Phe Val Leu Ser Arg Lys Glu Pro Met Trp Ala Asp Leu Leu Ala
305                 310                 315                 320

Leu Ala Ala Ala Arg Gly Gly Arg Val His Arg Ala Pro Glu Pro Tyr
                325                 330                 335

Lys Ala Leu Arg Asp Leu Lys Glu Ala Arg Gly Leu Leu Ala Lys Asp
                340                 345                 350

Leu Ser Val Leu Ala Leu Arg Glu Gly Leu Gly Leu Pro Pro Gly Asp
            355                 360                 365

Asp Pro Met Leu Leu Ala Tyr Leu Leu Asp Pro Ser Asn Thr Thr Pro
370                 375                 380

Glu Gly Val Ala Arg Arg Tyr Gly Gly Glu Trp Thr Glu Glu Ala Gly
385                 390                 395                 400

Glu Arg Ala Ala Leu Ser Glu Arg Leu Phe Ala Asn Leu Trp Gly Arg
                405                 410                 415

Leu Glu Gly Glu Glu Arg Leu Leu Trp Leu Tyr Arg Glu Val Glu Arg
            420                 425                 430

Pro Leu Ser Ala Val Leu Ala His Met Glu Ala Thr Gly Val Arg Leu
            435                 440                 445

Asp Val Ala Tyr Leu Arg Ala Leu Ser Leu Glu Val Ala Glu Glu Ile
450                 455                 460

Ala Arg Leu Glu Ala Glu Val Phe Arg Leu Ala Gly His Pro Phe Asn
465                 470                 475                 480

Leu Asn Ser Arg Asp Gln Leu Glu Arg Val Leu Phe Asp Glu Leu Gly
            485                 490                 495

Leu Pro Ala Ile Gly Lys Thr Glu Lys Thr Gly Lys Arg Ser Thr Ser
            500                 505                 510

Ala Ala Val Leu Glu Ala Leu Arg Glu Ala His Pro Ile Val Glu Lys
            515                 520                 525

Ile Leu Gln Tyr Arg Glu Leu Thr Lys Leu Lys Ser Thr Tyr Ile Asp
530                 535                 540

Pro Leu Pro Asp Leu Ile His Pro Arg Thr Gly Arg Leu His Thr Arg
545                 550                 555                 560

Phe Asn Gln Thr Ala Thr Ala Thr Gly Arg Leu Ser Ser Ser Asp Pro
                565                 570                 575

Asn Leu Gln Asn Ile Pro Val Arg Thr Pro Leu Gly Gln Arg Ile Arg
            580                 585                 590

Arg Ala Phe Ile Ala Glu Glu Gly Trp Leu Leu Val Val Leu Asp Tyr
            595                 600                 605

Ser Gln Ile Glu Leu Arg Val Leu Ala His Leu Ser Gly Asp Glu Asn
            610                 615                 620

Leu Ile Arg Val Phe Gln Glu Gly Arg Asp Ile His Thr Glu Thr Ala
625                 630                 635                 640

Ser Trp Met Phe Gly Val Pro Arg Glu Ala Val Asp Pro Leu Met Arg
```

-continued

```
                    645                 650                 655
Arg Ala Ala Lys Thr Ile Asn Phe Gly Val Leu Tyr Gly Met Ser Ala
                660                 665                 670
His Arg Leu Ser Gln Glu Leu Ala Ile Pro Tyr Glu Glu Ala Gln Ala
            675                 680                 685
Phe Ile Glu Arg Tyr Phe Gln Ser Phe Pro Lys Val Arg Ala Trp Ile
        690                 695                 700
Glu Lys Thr Leu Glu Glu Gly Arg Arg Arg Gly Tyr Val Glu Thr Leu
705                 710                 715                 720
Phe Gly Arg Arg Arg Tyr Val Pro Asp Leu Glu Ala Arg Val Lys Ser
                725                 730                 735
Val Arg Glu Ala Ala Glu Arg Met Ala Phe Asn Met Pro Val Gln Gly
                740                 745                 750
Thr Ala Ala Asp Leu Met Lys Leu Ala Met Val Lys Leu Phe Pro Arg
            755                 760                 765
Leu Glu Glu Met Gly Ala Arg Met Leu Leu Gln Val His Asp Glu Leu
        770                 775                 780
Val Leu Glu Ala Pro Lys Glu Arg Ala Glu Ala Val Ala Arg Leu Ala
785                 790                 795                 800
Lys Glu Val Met Glu Gly Val Tyr Pro Leu Ala Val Pro Leu Glu Val
                805                 810                 815
Glu Val Gly Ile Gly Glu Asp Trp Leu Ser Ala Lys Glu
            820                 825
```

<210> SEQ ID NO 19
<211> LENGTH: 2499
<212> TYPE: DNA
<213> ORGANISM: Artificial
<220> FEATURE:
<221> NAME/KEY: misc_feature
<222> LOCATION: (1)..(2499)
<223> OTHER INFORMATION: Thermostable mutant of Bacteriophage
      T7 polymerase.

<400> SEQUENCE: 19

```
tcgtggtacg catcctcttt tgagcccaa gggccgcgtc ctcctggtgg acggccacca      60
cctggcctac cgcaccttcc acgccctgaa gggcctcacc accagccggg gggagccggt     120
gcaggcggtc tacggcttcg ccaagagcct cctcaaggcc ctcaaggagg acggggacgc     180
ggtgatcgtg gtctttgacg ccaaggcccc ctcctcccgc acgaggcct acggggggta      240
caaggcgggc cgggccccca cgccggagga ctttccccgg caactcgccc tcatcaagga     300
gctggtggac ctcctggggc tggcgcgcct cgaggtcccg gctacgagg cggacgacgt      360
cctggccagc ctggccaaga aggcggaaaa ggagggctat gaggtccgca tcctcaccgc     420
cgacaaagac ctttaccagc tccttttcga ccgcatccac gtcctccacc ccgaggggta     480
cctcatcacc ccggcctggc tttgggaaaa gtacggcctg aggcccgacc agtgggccga     540
ctaccgggcc ctgaccgggg acgagtccga caaccttccc ggggtcaagg catcgggga      600
gaagacggcg aagaagcttc tggaggagtg ggggagcctg gaagccctcc tcgagaacct     660
ggaccggctg aagcccgcca tccgggagaa gatcctggcc cacatggacg atctgaagct     720
ctcctggac ctggccaagg tgcgcaccga cctgccctg gaggtggact cgccaaaag      780
gcgggagccc gaccgggaga ggcttagggc ctttctggag aggcttgagt tggcagcct      840
cctccacgag ttcggcttc tggaaagcc caaggcctg gaggaggcc ctggccccc      900
gccggaaggg gccttcgtgg gctttgtgct ttcccgcaag gagcccatgt gggccgatct     960
```

-continued

```
tctggccctg gccgccgcca ggggtggccg ggtccaccgg gccccgagc cttataaagc    1020
cctcagggac ttgaaggagg cgcggggggct tctcgccaaa gacctgagcg ttctggccct    1080
aagggaaggc cttggcctcc cgccggcga cgacccatg ctcctcgcct acctcctgga    1140
cccttccaac accaccccg aggggtggc ccggcgctac ggcggggagt ggacggagga    1200
ggcggggag cgggccgccc tttccgagag gctcttcgcc aacctgtggg ggaggcttga    1260
ggggaggag aggctccttt ggctttaccg ggaggtggat aggcccctttt ccgctgtcct    1320
ggcccacatg gaggccacag gggtgcgcct ggacgtggcc tatctcaggg ccttgtccct    1380
ggaggtggcc gaggagatcg cccgcctcga ggccgaggtc ttccgcctgg ccggccaccc    1440
cttcaacctc aactcccggg accagctgga aagggtcctc tttgacgagc tagggcttcc    1500
cgccatcggc aagacggaga agaccggcaa gcgctccacc agcgccgccg tcctggaggc    1560
cctccgcgag gcccacccca tcgtggaaa gatcctgcag taccgggagc tcaccaagct    1620
gaagagcacc tacattgacc ccttgccgga cctcatccac cccaggacgg ccgcctcca    1680
cacccgcttc aaccagacgg ccacggccac gggcaggcta agtagctccg atcccaacct    1740
ccagaacatc cccgtccgca ccccgcttgg gcagaggatc cgccgggcct tcatcgccga    1800
ggaggggtgg ctattggtgg tcctggacta tagccagata gagctcaggg tgctggccca    1860
cctctccggc gacgagaacc tgatccgggt cttccaggag gggcgggaca tccacacgga    1920
aaccgccagc tggatgttcg gcgtcccccg ggaggccgtg gaccccctga tgcgccgggc    1980
ggccaagacc atcaacttcg gggttctcta cggcatgtcg gcccaccgcc tctcccagga    2040
gctagccatc ccttacgagg aggcccaggc cttcattgag cgctactttc agagcttccc    2100
caaggtgcgg gcctggattg agaagaccct ggaggaggggc aggaggcggg ggtacgtgga    2160
gaccctcttc ggccgccgcc gctacgtgcc agaccctagag gcccgggtga agagcgtgcg    2220
ggaggcggcc gagcgcatgg ccttcaacat gccgtccag gcaccgccg ccgacctcat    2280
gaagctggct atggtgaagc tcttccccag gctggaggaa atgggggcca ggatgctcct    2340
tcaggtccac gacgagctgg tcctcgaggc cccaaagag agggcggagg ccgtggcccg    2400
gctggccaag gaggtcatgg aggggtgta tcccctggcc gtgccctgg aggtggaggt    2460
ggggataggg gaggactggc tctccgccaa ggagtgagt            2499
```

<210> SEQ ID NO 20
<211> LENGTH: 827
<212> TYPE: PRT
<213> ORGANISM: Artificial
<220> FEATURE:
<221> NAME/KEY: MISC_FEATURE
<222> LOCATION: (1)..(827)
<223> OTHER INFORMATION: Mutant of Taq polymerase.

<400> SEQUENCE: 20

```
Pro Leu Phe Glu Pro Lys Gly Arg Val Leu Leu Val Asp Gly His His
1               5                   10                  15

Leu Ala Tyr Arg Thr Phe His Ala Leu Lys Gly Leu Thr Thr Ser Arg
                20                  25                  30

Gly Glu Pro Val Gln Ala Val Tyr Gly Phe Ala Lys Ser Leu Leu Lys
            35                  40                  45

Ala Leu Lys Glu Asp Gly Asp Ala Val Ile Val Phe Asp Ala Lys
        50                  55                  60

Ala Pro Ser Ser Arg His Glu Ala Tyr Gly Gly Tyr Lys Ala Gly Arg
65                  70                  75                  80
```

-continued

```
Ala Pro Thr Pro Glu Asp Phe Pro Arg Gln Leu Ala Leu Ile Lys Glu
                85                  90                  95

Leu Val Asp Leu Leu Gly Leu Ala Arg Leu Glu Val Pro Gly Tyr Glu
            100                 105                 110

Ala Asp Asp Val Leu Ala Ser Leu Ala Lys Lys Ala Glu Lys Glu Gly
        115                 120                 125

Tyr Glu Val Arg Ile Leu Thr Ala Asp Lys Asp Leu Tyr Gln Leu Leu
    130                 135                 140

Ser Asp Arg Ile His Val Leu His Pro Glu Gly Tyr Leu Ile Thr Pro
145                 150                 155                 160

Ala Trp Leu Trp Glu Lys Tyr Gly Leu Arg Pro Asp Gln Trp Ala Asp
                165                 170                 175

Tyr Arg Ala Leu Thr Gly Asp Glu Ser Asp Asn Leu Pro Gly Val Lys
            180                 185                 190

Gly Ile Gly Glu Lys Thr Ala Lys Lys Leu Leu Glu Glu Trp Gly Ser
        195                 200                 205

Leu Glu Ala Leu Leu Glu Asn Leu Asp Arg Leu Lys Pro Ala Ile Arg
    210                 215                 220

Glu Lys Ile Leu Ala His Thr Asp Asp Leu Lys Leu Ser Trp Asp Leu
225                 230                 235                 240

Ala Lys Val Arg Thr Asp Leu Pro Leu Glu Val Asp Phe Ala Lys Arg
                245                 250                 255

Arg Glu Pro Asp Arg Glu Arg Leu Arg Ala Phe Leu Glu Arg Leu Glu
            260                 265                 270

Phe Gly Ser Leu Leu His Glu Phe Gly Leu Leu Glu Ser Pro Lys Ala
        275                 280                 285

Leu Glu Glu Ala Pro Trp Pro Pro Glu Gly Ala Phe Val Gly Phe
    290                 295                 300

Val Leu Ser Arg Lys Glu Pro Met Trp Ala Asp Leu Leu Ala Leu Ala
305                 310                 315                 320

Ala Ala Arg Gly Gly Arg Val His Arg Ala Pro Glu Pro Tyr Lys Ala
                325                 330                 335

Leu Arg Asp Leu Lys Glu Ala Arg Gly Leu Leu Ala Lys Asp Leu Ser
            340                 345                 350

Val Leu Ala Leu Arg Glu Gly Leu Gly Leu Pro Pro Gly Asp Asp Pro
        355                 360                 365

Met Leu Leu Ala Tyr Leu Leu Asp Pro Ser Asn Thr Thr Pro Glu Gly
    370                 375                 380

Val Ala Arg Arg Tyr Gly Gly Glu Trp Thr Glu Glu Ala Gly Glu Arg
385                 390                 395                 400

Ala Ala Leu Ser Glu Arg Leu Phe Ala Asn Leu Trp Gly Arg Leu Glu
                405                 410                 415

Gly Glu Glu Arg Leu Leu Trp Leu Tyr Arg Glu Val Asp Arg Pro Leu
            420                 425                 430

Ser Ala Val Leu Ala His Met Glu Ala Thr Gly Val Arg Leu Asp Val
        435                 440                 445

Ala Tyr Leu Arg Ala Leu Ser Leu Glu Val Ala Glu Glu Ile Ala Arg
    450                 455                 460

Leu Glu Ala Glu Val Phe Arg Leu Ala Gly His Pro Phe Asn Leu Asn
465                 470                 475                 480

Ser Arg Asp Gln Leu Glu Arg Val Leu Phe Asp Glu Leu Gly Leu Pro
                485                 490                 495
```

-continued

```
Ala Ile Gly Lys Thr Glu Lys Thr Gly Lys Arg Ser Thr Ser Ala Ala
            500                 505                 510

Val Leu Glu Ala Leu Arg Glu Ala His Pro Ile Val Glu Lys Ile Leu
        515                 520                 525

Gln Tyr Arg Glu Leu Thr Lys Leu Lys Ser Thr Tyr Ile Asp Pro Leu
    530                 535                 540

Pro Asp Leu Ile His Pro Arg Thr Gly Arg Leu His Thr Arg Phe Asn
545                 550                 555                 560

Gln Thr Ala Thr Ala Thr Gly Arg Leu Ser Ser Ser Asp Pro Asn Leu
                565                 570                 575

Gln Asn Ile Pro Val Arg Thr Pro Leu Gly Gln Arg Ile Arg Arg Ala
            580                 585                 590

Phe Ile Ala Glu Glu Gly Trp Leu Leu Val Val Leu Asp Tyr Ser Gln
        595                 600                 605

Ile Glu Leu Arg Val Leu Ala His Leu Ser Gly Asp Glu Asn Leu Ile
    610                 615                 620

Arg Val Phe Gln Glu Gly Arg Asp Ile His Thr Glu Thr Ala Ser Trp
625                 630                 635                 640

Met Phe Gly Val Pro Arg Glu Ala Val Asp Pro Leu Met Arg Arg Ala
                645                 650                 655

Ala Lys Thr Ile Asn Phe Gly Val Leu Tyr Gly Met Ser Ala His Arg
            660                 665                 670

Leu Ser Gln Glu Leu Ala Ile Pro Tyr Glu Glu Ala Gln Ala Phe Ile
        675                 680                 685

Glu Arg Tyr Phe Gln Ser Phe Pro Lys Val Arg Ala Trp Ile Glu Lys
    690                 695                 700

Thr Leu Glu Glu Gly Arg Arg Arg Gly Tyr Val Glu Thr Leu Phe Gly
705                 710                 715                 720

Arg Arg Arg Tyr Val Pro Asp Leu Glu Ala Arg Val Lys Ser Val Arg
                725                 730                 735

Glu Ala Ala Glu Arg Met Ala Phe Asn Met Pro Val Gln Gly Thr Ala
            740                 745                 750

Ala Asp Leu Met Lys Leu Ala Met Val Lys Leu Phe Pro Arg Leu Glu
        755                 760                 765

Glu Met Gly Ala Arg Met Leu Leu Gln Val His Asp Glu Leu Val Leu
    770                 775                 780

Glu Ala Pro Lys Glu Arg Ala Glu Ala Val Ala Arg Leu Ala Lys Glu
785                 790                 795                 800

Val Met Glu Gly Val Tyr Pro Leu Ala Val Pro Leu Glu Val Glu Val
                805                 810                 815

Gly Ile Gly Glu Asp Trp Leu Ser Ala Lys Glu
            820                 825
```

<210> SEQ ID NO 21
<211> LENGTH: 2483
<212> TYPE: DNA
<213> ORGANISM: Artificial
<220> FEATURE:
<221> NAME/KEY: misc_feature
<222> LOCATION: (1)..(2483)
<223> OTHER INFORMATION: Heparin-resistant mutant of Taq polymerase.

<400> SEQUENCE: 21

```
atttttgagc ccaagggccg cgtcctcctg gtggacggcc accacctggc ctaccgcacc      60
ttccacgccc tgaagggcct caccaccagc cggggggagc cggtgcaggc ggtctacggc     120
```

```
ttcgccaaga gcctcctcaa ggccctcaag gaggacgggg acgcggtgat cgtggtcttt      180
gacgccaagg cccctcctt  ccgccacgag gcctacgggg ggtacaaggc gggccgggcc      240
cccacgccgg aggactttcc ccggcaactc gccctcatca aggagctggt ggacctcctg      300
gggctggcgc gcctcgaggt cccgggctac gaggcggacg acgtcctggc cagcctggcc      360
aagaaggcgg aaaaggaggg ctacgaggtc cgcatcctca ccgccgacaa agacctttac      420
cagctccttt ccgaccgcat ccacgtcctc caccccgagg ggtacctcat caccccggcc      480
tggctttggg aaaagtacgg cctgaggccc gaccagtggg ccgactaccg ggccctgacc      540
ggggacgagt ccgacaacct tcccggtgtc aagggcatcg ggagaagac  ggcgaggaag      600 cttctggagg agtggggggag cctggaagcc ctcctcaaga acctggaccg gctggagccc      660
gccatccggg agaagatcct ggcccacatg gacgatctga agctctcctg ggacctggcc      720
aaggtgcgca ccgacctgcc cctggaggtg gacttcgcca aaaggcggga gcccgaccgg      780
gagaggctta gggccttct  ggagaggctt gagtttggca gcctcctcca cgagttcggc      840
cttctggaaa gccccaaggc cccggaggag gcccctggc  cccgccgga  aggggccttc      900 gtgggctttg tgctttcccg caaggagccc atgtgggccg atcttctggc cctgccgcc       960 gccagggggg gccgggtcca ccgggccccc gagccttata aagccctcag ggacctgaag      1020
gaggcgcggg ggcttctcgc caaagacctg agcgttctgg ccctgaggga aggccttggc      1080
ctcccgcccg gcgacgaccc catgctcctc gcctacctcc tggacccttc caacaccacc      1140
cccgaggggg tggcccggcg ctacggcggg gagtggacgg aggaggcggg ggagcgggcc      1200 gcccctttccg agaggctctt cgccaacctg tggggaggc  ttgaggggga ggagaggctc      1260
ctttggcttt accgggaggt ggagaggccc ctttccgctg tcctggccca catggaggcc      1320
acgggggtgc gcctggacgt gtcctatctc agggccttgt cccgggaggt ggccgaggag      1380
atcgcccgcc tcgaggccga ggtcttccgc ctggccggcc acccccttca acctcaactcc      1440 cgggaccagc tggaaagggt cctctttgac gagctagggc ttcccgccat cggcaagacg      1500
gagaagaccg gcaagcgctc caccagcgcc gccgtcctgg aggccctccg cgaggcccac      1560
cccatcgtgg agaagatcct gcagtaccgg gagctcacca agctgaagag cacctacatt      1620 gacccccttgc cggacctcat ccaccccagg acgggccgcc tccacacccg cttcaaccag      1680
acggccacgg ccacgggcag gctaagtagc tccggtccca acctccagag catccccgtc      1740
cgcaccccgc ttgggcagag gatccgccgg gccttcatcg ccgaggaggg gtggctattg      1800
gtggccctgg actatagcca gatagagctc aggggtgctgg cccacctctc cggcgacgag      1860
aacctgatcc gggtcttcca ggaggggcgg gacatccaca cggagaccgc cagctggatg      1920
ttcggcgtcc cccgggaggc cgtggacccc ctgatgcgcc gggcggccaa gaccatcaac      1980
ttcggggtcc tctacggcat gtcggcccac cgcctctccc aggagctagc catcccttac      2040
gaggaggccc aggccttcat tgagcgctac tttcagagct cccccaaggt gcgggcctgg      2100
attgagaaga cctggaggg  gggcaggagg cgggggtacg tggagaccct cttcggccgc      2160
cgccgctacg tgccagacct agaggccggg gtgaagagcg tgcgggaggc ggccgagcgc      2220
atggccttca acatgcccgt ccagggcacc gccgccgacc tcatgaagct ggctatggtg      2280
aagctcttcc ccaggctgga ggaaatgggg gccaggatgc tccttcaggt ccacgacgag      2340
ctggtcctcg aggccccaaa agagagggcg gaggccgtgg cccggctggc caaggaggtc      2400
atggaggggg tgtatcccct ggccgtgccc ctggaggtgg aggtggggat aggggaggac      2460
tggctctccg ccaaggagtg att                                             2483
```

<210> SEQ ID NO 22
<211> LENGTH: 825
<212> TYPE: PRT
<213> ORGANISM: Artificial
<220> FEATURE:
<221> NAME/KEY: MISC_FEATURE
<222> LOCATION: (1)..(825)
<223> OTHER INFORMATION: Heparin-resistant mutant of Taq polymerase.

<400> SEQUENCE: 22

```
Phe Glu Pro Lys Gly Arg Val Leu Leu Val Asp Gly His His Leu Ala
1               5                   10                  15

Tyr Arg Thr Phe His Ala Leu Lys Gly Leu Thr Thr Ser Arg Gly Glu
            20                  25                  30

Pro Val Gln Ala Val Tyr Gly Phe Ala Lys Ser Leu Leu Lys Ala Leu
        35                  40                  45

Lys Glu Asp Gly Asp Ala Val Ile Val Val Phe Asp Ala Lys Ala Pro
    50                  55                  60

Ser Phe Arg His Glu Ala Tyr Gly Gly Tyr Lys Ala Gly Arg Ala Pro
65                  70                  75                  80

Thr Pro Glu Asp Phe Pro Arg Gln Leu Ala Leu Ile Lys Glu Leu Val
                85                  90                  95

Asp Leu Leu Gly Leu Ala Arg Leu Glu Val Pro Gly Tyr Glu Ala Asp
            100                 105                 110

Asp Val Leu Ala Ser Leu Ala Lys Lys Ala Glu Lys Glu Gly Tyr Glu
        115                 120                 125

Val Arg Ile Leu Thr Ala Asp Lys Asp Leu Tyr Gln Leu Leu Ser Asp
    130                 135                 140

Arg Ile His Val Leu His Pro Glu Gly Tyr Leu Ile Thr Pro Ala Trp
145                 150                 155                 160

Leu Trp Glu Lys Tyr Gly Leu Arg Pro Asp Gln Trp Ala Asp Tyr Arg
                165                 170                 175

Ala Leu Thr Gly Asp Glu Ser Asp Asn Leu Pro Gly Val Lys Gly Ile
            180                 185                 190

Gly Glu Lys Thr Ala Arg Lys Leu Leu Glu Glu Trp Gly Ser Leu Glu
        195                 200                 205

Ala Leu Leu Lys Asn Leu Asp Arg Leu Glu Pro Ala Ile Arg Glu Lys
    210                 215                 220

Ile Leu Ala His Met Asp Asp Leu Lys Leu Ser Trp Asp Leu Ala Lys
225                 230                 235                 240

Val Arg Thr Asp Leu Pro Leu Glu Val Asp Phe Ala Lys Arg Arg Glu
                245                 250                 255

Pro Asp Arg Glu Arg Leu Arg Ala Phe Leu Glu Arg Leu Glu Phe Gly
            260                 265                 270

Ser Leu Leu His Glu Phe Gly Leu Leu Glu Ser Pro Lys Ala Pro Glu
        275                 280                 285

Glu Ala Pro Trp Pro Pro Pro Glu Gly Ala Phe Val Gly Phe Val Leu
    290                 295                 300

Ser Arg Lys Glu Pro Met Trp Ala Asp Leu Leu Ala Leu Ala Ala Ala
305                 310                 315                 320

Arg Gly Gly Arg Val His Arg Ala Pro Glu Pro Tyr Lys Ala Leu Arg
                325                 330                 335

Asp Leu Lys Glu Ala Arg Gly Leu Leu Ala Lys Asp Leu Ser Val Leu
            340                 345                 350
```

```
Ala Leu Arg Glu Gly Leu Gly Leu Pro Pro Gly Asp Pro Met Leu
        355                 360                 365

Leu Ala Tyr Leu Leu Asp Pro Ser Asn Thr Thr Pro Glu Gly Val Ala
        370                 375                 380

Arg Arg Tyr Gly Gly Glu Trp Thr Glu Glu Ala Gly Glu Arg Ala Ala
385                 390                 395                 400

Leu Ser Glu Arg Leu Phe Ala Asn Leu Trp Gly Arg Leu Glu Gly Glu
                405                 410                 415

Glu Arg Leu Leu Trp Leu Tyr Arg Glu Val Glu Arg Pro Leu Ser Ala
                420                 425                 430

Val Leu Ala His Met Glu Ala Thr Gly Val Arg Leu Asp Val Ser Tyr
            435                 440                 445

Leu Arg Ala Leu Ser Arg Glu Val Ala Glu Ile Ala Arg Leu Glu
        450                 455                 460

Ala Glu Val Phe Arg Leu Ala Gly His Pro Phe Asn Leu Asn Ser Arg
465                 470                 475                 480

Asp Gln Leu Glu Arg Val Leu Phe Asp Glu Leu Gly Leu Pro Ala Ile
                485                 490                 495

Gly Lys Thr Glu Lys Thr Gly Lys Arg Ser Thr Ser Ala Ala Val Leu
            500                 505                 510

Glu Ala Leu Arg Glu Ala His Pro Ile Val Glu Lys Ile Leu Gln Tyr
        515                 520                 525

Arg Glu Leu Thr Lys Leu Lys Ser Thr Tyr Ile Asp Pro Leu Pro Asp
        530                 535                 540

Leu Ile His Pro Arg Thr Gly Arg Leu His Thr Arg Phe Asn Gln Thr
545                 550                 555                 560

Ala Thr Ala Thr Gly Arg Leu Ser Ser Ser Gly Pro Asn Leu Gln Ser
                565                 570                 575

Ile Pro Val Arg Thr Pro Leu Gly Gln Arg Ile Arg Arg Ala Phe Ile
                580                 585                 590

Ala Glu Glu Gly Trp Leu Leu Val Ala Leu Asp Tyr Ser Gln Ile Glu
            595                 600                 605

Leu Arg Val Leu Ala His Leu Ser Gly Asp Glu Asn Leu Ile Arg Val
        610                 615                 620

Phe Gln Glu Gly Arg Asp Ile His Thr Glu Thr Ala Ser Trp Met Phe
625                 630                 635                 640

Gly Val Pro Arg Glu Ala Val Asp Pro Leu Met Arg Arg Ala Ala Lys
                645                 650                 655

Thr Ile Asn Phe Gly Val Leu Tyr Gly Met Ser Ala His Arg Leu Ser
            660                 665                 670

Gln Glu Leu Ala Ile Pro Tyr Glu Glu Ala Gln Ala Phe Ile Glu Arg
        675                 680                 685

Tyr Phe Gln Ser Phe Pro Lys Val Arg Ala Trp Ile Glu Lys Thr Leu
        690                 695                 700

Glu Glu Gly Arg Arg Arg Gly Tyr Val Glu Thr Leu Phe Gly Arg Arg
705                 710                 715                 720

Arg Tyr Val Pro Asp Leu Glu Ala Arg Val Lys Ser Val Arg Glu Ala
                725                 730                 735

Ala Glu Arg Met Ala Phe Asn Met Pro Val Gln Gly Thr Ala Ala Asp
            740                 745                 750

Leu Met Lys Leu Ala Met Val Lys Leu Phe Pro Arg Leu Glu Glu Met
        755                 760                 765

Gly Ala Arg Met Leu Leu Gln Val His Asp Glu Leu Val Leu Glu Ala
```

```
             770               775               780
Pro Lys Glu Arg Ala Glu Ala Val Ala Arg Leu Ala Lys Glu Val Met
785               790               795               800

Glu Gly Val Tyr Pro Leu Ala Val Pro Leu Glu Val Glu Val Gly Ile
            805               810               815

Gly Glu Asp Trp Leu Ser Ala Lys Glu
            820               825

<210> SEQ ID NO 23
<211> LENGTH: 2481
<212> TYPE: DNA
<213> ORGANISM: Artificial
<220> FEATURE:
<221> NAME/KEY: misc_feature
<222> LOCATION: (1)..(2481)
<223> OTHER INFORMATION: Heparin-resistant mutant of Taq polymerase.

<400> SEQUENCE: 23
tttgagccca agggccgcgt cctcctggtg gacggccacc acctggccta ccgcaccttc      60
cacgccctga agggcctcac caccagccgg ggggagccgg tgcaggcggt ctacggcttc     120
gccaagagcc tcctcaaggc cctcaaggag gacgggacg cggtgatcgt ggtctttgac      180
gccaaggccc cctccttccg ccacgaggcc tacgggggt acaaggcggg ccgggccccc      240
acgccggagg actttccccg gcaactcgcc ctcatcaagg agctggtgga cctcctgggg     300
ctggcgcgcc tcgaggtccc gggctacgag gcggacgacg tcctggccag cctggccaag     360
aaggcggaaa aggagggcta cgaggtccgc atcctcaccg ccgacaaaga cctttaccag     420
ctcctttccg accgcatcca cgtcctccac cccgaggggt acctcatcac cccggcctgg     480 cttttgggaaa agtacggcct gaggcccgac cagtgggccg actaccggc cctgaccggg     540 gacgagtccg acaaccttcc cggtgtcaag ggcatcgggg agaagacggc gaggaagcct     600 tctgaggag tggggggagcc tggaagccct cctcaagaac ctggaccggc tggagcccgc     660
catccgggag aagatcctgg cccacatgga cgatctgaag ctctcctggg acctggccaa     720
ggtgcgcacc gacctgcccc tggaggtgga cttcgccaaa aggcgggagc ccgaccggga     780
gaggcttagg gccttttctgg agaggcttga gtttggcagc ctcctccacg agttcggcct     840
tctggaaagc cccaaggccc tggaggaggc ccctgggccc cgccggaag gggcttcgt      900 gggctttgtg ctttcccgca aggagcccat gtgggccgat cttctggccc tggccgccgc     960 caggggggt cgggtccacc gggccccga gccttataaa gccctcaggg acctgaagga    1020
ggcgcggggg cttctcgcca aagacctgag cgttctggcc ctgagggaag gccttggcct    1080 cccgccggc gacgaccca tgctcctcgc ctacctcctg gacccttcca acaccacccc    1140
cgtgggggtg gccggcgct acggcgggga gtggacggag gaggcggggg agcgggccgc    1200
cctttccgag aggctcttcg ccaacctgtg ggggaggctt gaggggagg agaggctcct    1260 ttggctttac cgggaggtgg agaggcccct ttccgctgtc ctggcccaca tggaggctac    1320
gggggtgcgc ctggacgtgg cctatctcag ggccttgtcc ctggaggtgg ccgaggagat    1380
cgcccgcctc gaggccgagg tcttccgcct ggccggccac cccttcaacc tcaactcccg    1440
ggaccagctg gaaagggtcc tctttgacga gctagggctt cccgccatcg gcaagacgga    1500
gaagaccggc aagcgctcca ccagcgccgc cgtcctggaa gccctccgcg aggcccaccc    1560
catcgtggag aagatcctgc agtacccgga gctcaccagg ctgaagagca cctacattga    1620
ccccttgccg gacctcatcc accccaggac gggccgcctc cacaccgct tcaaccagac    1680
```

-continued

```
ggccacggcc acgggcaggc taagtagctc cggtcccaac ctccagagca tccccgtccg    1740 cacccccgctt gggcagagga tccgccgggc cttcatcgcc gaggaggggt ggctattggt   1800
ggccctggac tatagccaga tagagctcag ggtgctggcc cacctctccg gcgacgagaa    1860
cctgatccgg gtcttccagg aggggcggga catccacacg gagaccgcca gctggatgtt    1920
cggcgtcccc cggaggccg tggaccccct gatgcgccgg gcggccaaga ccatcaactt     1980
cggggtcctc tacggcatgt cggcccaccg cctctcccag gagctagcca tcccttacga    2040
ggaggcccag gccttcattg agcgctactt tcagagcttc cccaaggtgc gggcctggat    2100
tgagaagacc ctggaggagg caggaggcg ggggtacgtg gagaccctct cggccgccg      2160 ccgctacgtg ccagacctag aggcccgggt gaagagcgtg cgggaggcgg ccgagcgcag    2220
ggccttcaac atgcccgtcc agggcaccgc cgccgacctc atgaagctgg ctatggtgaa    2280
gctcttcccc aggctggagg aaatgggggc caggatgctc cttcaggtcc acgacgagct    2340
ggtcctcgag gccccaaaag agagggcgga ggccgtggcc cggctggcca aggaggtcat    2400 ggaggggtg tatcccctgg ccgtgcccct ggaggtggag gtggggatag ggaggactg      2460 gctctccgcc aaggagtgag t                                              2481
```

<210> SEQ ID NO 24
<211> LENGTH: 827
<212> TYPE: PRT
<213> ORGANISM: Artificial
<220> FEATURE:
<221> NAME/KEY: MISC_FEATURE
<222> LOCATION: (1)..(827)
<223> OTHER INFORMATION: Heparin-resistant mutant of Taq polymerase.

<400> SEQUENCE: 24

```
Pro Leu Phe Glu Pro Lys Gly Arg Val Leu Leu Val Asp Gly His His
1               5                   10                  15

Leu Ala Tyr Arg Thr Phe His Ala Leu Lys Gly Leu Thr Thr Ser Arg
            20                  25                  30

Gly Glu Pro Val Gln Ala Val Tyr Gly Phe Ala Lys Ser Leu Leu Lys
        35                  40                  45

Ala Leu Lys Glu Asp Gly Asp Ala Val Ile Val Val Phe Asp Ala Lys
    50                  55                  60

Ala Pro Ser Phe Arg His Glu Ala Tyr Gly Gly Tyr Lys Ala Gly Arg
65                  70                  75                  80

Ala Pro Thr Pro Glu Asp Phe Pro Arg Gln Leu Ala Leu Ile Lys Glu
                85                  90                  95

Leu Val Asp Leu Leu Gly Leu Ala Arg Leu Glu Val Pro Gly Tyr Glu
            100                 105                 110

Ala Asp Asp Val Leu Ala Ser Leu Ala Lys Lys Ala Glu Lys Glu Gly
        115                 120                 125

Tyr Glu Val Arg Ile Leu Thr Ala Asp Lys Asp Leu Tyr Gln Leu Leu
    130                 135                 140

Ser Asp Arg Ile His Val Leu His Pro Glu Gly Tyr Leu Ile Thr Pro
145                 150                 155                 160

Ala Trp Leu Trp Glu Lys Tyr Gly Leu Arg Pro Asp Gln Trp Ala Asp
                165                 170                 175

Tyr Arg Ala Leu Thr Gly Asp Glu Ser Asp Asn Leu Pro Gly Val Lys
            180                 185                 190

Gly Ile Gly Glu Lys Thr Ala Arg Lys Leu Leu Glu Glu Trp Gly Ser
        195                 200                 205
```

```
Leu Glu Ala Leu Leu Lys Asn Leu Asp Arg Leu Pro Ala Ile Arg
    210                 215                 220

Glu Lys Ile Leu Ala His Met Asp Asp Leu Lys Leu Ser Trp Asp Leu
225                 230                 235                 240

Ala Lys Val Arg Thr Asp Leu Pro Leu Glu Val Asp Phe Ala Lys Arg
                245                 250                 255

Arg Glu Pro Asp Arg Glu Arg Leu Arg Ala Phe Leu Glu Arg Leu Glu
            260                 265                 270

Phe Gly Ser Leu Leu His Glu Phe Gly Leu Leu Glu Ser Pro Lys Ala
        275                 280                 285

Leu Glu Glu Ala Pro Trp Pro Pro Glu Gly Ala Phe Val Gly Phe
    290                 295                 300

Val Leu Ser Arg Lys Glu Pro Met Trp Ala Asp Leu Leu Ala Leu Ala
305                 310                 315                 320

Ala Ala Arg Gly Gly Arg Val His Arg Ala Pro Glu Pro Tyr Lys Ala
                325                 330                 335

Leu Arg Asp Leu Lys Glu Ala Arg Gly Leu Leu Ala Lys Asp Leu Ser
            340                 345                 350

Val Leu Ala Leu Arg Glu Gly Leu Gly Leu Pro Pro Gly Asp Asp Pro
        355                 360                 365

Met Leu Leu Ala Tyr Leu Leu Asp Pro Ser Asn Thr Thr Pro Val Gly
    370                 375                 380

Val Ala Arg Arg Tyr Gly Gly Glu Trp Thr Glu Glu Ala Gly Glu Arg
385                 390                 395                 400

Ala Ala Leu Ser Glu Arg Leu Phe Ala Asn Leu Trp Gly Arg Leu Glu
                405                 410                 415

Gly Glu Glu Arg Leu Leu Trp Leu Tyr Arg Glu Val Glu Arg Pro Leu
            420                 425                 430

Ser Ala Val Leu Ala His Met Glu Ala Thr Gly Val Arg Leu Asp Val
        435                 440                 445

Ala Tyr Leu Arg Ala Leu Ser Leu Glu Val Ala Glu Glu Ile Ala Arg
    450                 455                 460

Leu Glu Ala Glu Val Phe Arg Leu Ala Gly His Pro Phe Asn Leu Asn
465                 470                 475                 480

Ser Arg Asp Gln Leu Glu Arg Val Leu Phe Asp Glu Leu Gly Leu Pro
                485                 490                 495

Ala Ile Gly Lys Thr Glu Lys Thr Gly Lys Arg Ser Thr Ser Ala Ala
            500                 505                 510

Val Leu Glu Ala Leu Arg Glu Ala His Pro Ile Val Glu Lys Ile Leu
        515                 520                 525

Gln Tyr Arg Glu Leu Thr Arg Leu Lys Ser Thr Tyr Ile Asp Pro Leu
    530                 535                 540

Pro Asp Leu Ile His Pro Arg Thr Gly Arg Leu His Thr Arg Phe Asn
545                 550                 555                 560

Gln Thr Ala Thr Ala Thr Gly Arg Leu Ser Ser Ser Gly Pro Asn Leu
                565                 570                 575

Gln Ser Ile Pro Val Arg Thr Pro Leu Gly Gln Arg Ile Arg Arg Ala
            580                 585                 590

Phe Ile Ala Glu Glu Gly Trp Leu Leu Val Ala Leu Asp Tyr Ser Gln
        595                 600                 605

Ile Glu Leu Arg Val Leu Ala His Leu Ser Gly Asp Glu Asn Leu Ile
    610                 615                 620

Arg Val Phe Gln Glu Gly Arg Asp Ile His Thr Glu Thr Ala Ser Trp
```

```
                625                 630                 635                 640
Met Phe Gly Val Pro Arg Glu Ala Val Asp Pro Leu Met Arg Arg Ala
                    645                 650                 655
Ala Lys Thr Ile Asn Phe Gly Val Leu Tyr Gly Met Ser Ala His Arg
                660                 665                 670
Leu Ser Gln Glu Leu Ala Ile Pro Tyr Glu Glu Ala Gln Ala Phe Thr
            675                 680                 685
Glu Arg Tyr Phe Gln Ser Phe Pro Lys Val Arg Ala Trp Ile Glu Lys
        690                 695                 700
Thr Leu Glu Glu Gly Arg Arg Arg Gly Tyr Val Glu Thr Leu Phe Gly
705                 710                 715                 720
Arg Arg Arg Tyr Val Pro Asp Leu Glu Ala Arg Val Lys Ser Val Arg
                    725                 730                 735
Glu Ala Ala Glu Arg Arg Ala Phe Asn Met Pro Val Gln Gly Thr Ala
                740                 745                 750
Ala Asp Leu Met Lys Leu Ala Met Val Lys Leu Phe Pro Arg Leu Glu
            755                 760                 765
Glu Met Gly Ala Arg Met Leu Leu Gln Val His Asp Glu Leu Val Leu
        770                 775                 780
Glu Ala Pro Lys Glu Arg Ala Glu Ala Val Ala Arg Leu Ala Lys Glu
785                 790                 795                 800
Val Met Glu Gly Val Tyr Pro Leu Ala Val Pro Leu Glu Val Glu Val
                    805                 810                 815
Gly Ile Gly Glu Asp Trp Leu Ser Ala Lys Glu
                820                 825

<210> SEQ ID NO 25
<211> LENGTH: 2849
<212> TYPE: DNA
<213> ORGANISM: Artificial
<220> FEATURE:
<221> NAME/KEY: misc_feature
<222> LOCATION: (1)..(2849)
<223> OTHER INFORMATION: Mismatch extension mutant of Taq polymerase.

<400> SEQUENCE: 25
ttggaatgct ccctcttttt gagcccaaag gccgcgtcct cctggtggac ggccaccacc        60
tggcctaccg caccttccac gccctgaagg gcctcaccac cagccggggg gagccggtgc       120
aggcggtcta cggcttcgcc aagagcctcc tcaaggccct caaggaggac ggggacgcgg       180
tgatcgtggt ctttgacgcc aaggccccct ccttccgcca cgaggcctac ggggggtaca       240
aggcggcccg gccccccacg ccggaggact tccccggca actcgccctc atcaaggagc        300
tggtggatct cctggggctg gcgcgcctcg aggtccggg ctacgaggcg gacgacgtcc        360
tggccagcct ggccaagaag gcggaaaagg agggctacga ggtccgcatc ctcaccgccg       420 acaaggcct taccagctc ctttccgacc gcatccacgt cctccacccc gagggggtacc       480 tcatcacccc ggcctggctt tgggaaaagt acggcctgag gcccgaccag tgggccgact       540 accgggcccct gaccggggac gagtccgaca accttcccgg ggtcaagggc atcggggaga       600
agacggcgag gaagcttctg gaggagtggg ggagcctgga agccctcctc aagaacctgg       660
accggctgaa gccgccatc ggggagaaga tcctggccca catggacgat ctgaagctct       720
cctgggatct ggccaaggtg cgcaccgacc gccctggag gtggacttcg ccaaaaggcg       780
ggagcccgac cggagaggc ttagggcctt tctggagagg cttgagtttg cagcctcct        840 ccacgagttc ggccttctgg aaagccccaa ggccctggag gaggcccct ggccccgcc        900
```

```
ggaaggggcc ttcgtgggct ttgtcctttc ccgcagggag cccatgtggg ccgatcttct    960
ggccctggcc gccgccaggg ggggccgggt ccaccgggcc cccgagcctt ataaagccct   1020
cagggacctg aaggaggcgc gggggcttct cgccaaagac ctgagcgttc tggccctgag   1080
ggaaggcctt ggcctcccgc ccggcgacga ccccatgctc ctcgcctacc tcctggaccc   1140
ttccaacacc accccgagg gggtggcccg cgctacggc ggggagtgga cggaggaggc     1200
gggggagcgg gccgcccttt ccgagaggct cttcgccaac ctgtggggga ggcttgaggg   1260
ggaggagagg ctcctttggc tttaccggga ggtggagagg cccctttccg ctgtcctggc   1320
ccacatggag gccacggggg tgcgcctgga cgtggcctat ctcagggcct tgtccctgga   1380
ggtggccgag gagatcgccc gcctcgaggc cgaggtcttc cgcctggccg ccacccctt    1440 caacctcaac tcccgggacc agctggaaag ggtcctcttt gacgagctag gcttcccgc    1500 catcggcaag acgagaaga ccggcaagcg ctccaccagc gccgccgtcc tgggggccct    1560
ccgcgaggcc cacccatcg tggagaagat cctgcagtac cgggagctca ccaagctgaa    1620
gagcacctac attgacccct taccggacct catccaccc aggacgggcc gcctccacac    1680
ccgcttcaac cagacggcca cggccacggg caggctaagt agctccgatc ccaacctcca   1740
gaacatcccc gtccgcaccc cgcttgggca gaggatccgc cgggccttca tcgccgagga   1800
ggggtggcta ttggtggtcc tggactatag ccagatagag ctcagggtgc tggcccacct   1860
ctccggcgac gagaacctga tccgggtctt ccaggagggg cgggacatcc acacggagac   1920
cgccagctgg atgttcggcg tccccgga ggccgtggac cccctgatgc gccgggcgg      1980 caagaccatc aacttcgggg tcctctacgg catgtcggcc caccgcctct cccaggagct   2040
agccatccct tacgaggagg cccaggcctt cattgagcgc tactttcaga gcttccccaa   2100
ggtgcgggcc tggattgaga agaccctgga ggagggcagg aggcgggggt acgtggagac   2160
cctcttcggc cgccgccgct acgtgccaga cctagaggcc cgggtgaaga gcgtgcgggg   2220
ggcggccgag cgcatggcct tcaacatgcc cgtccagggc accgccgccg acctcatgaa   2280
gctggctatg gtgaagctct cccccaggct ggaggaaatg ggggcagga tgctccttca    2340 ggtccacgac gagctggtcc tcgaggcccc aaaagagagg gcggaggccg tggcccggct   2400
ggccaaggag gtcatggagg gggtgtatcc cctggccgtg cccctggagg tggaggtggg   2460 gatagggggag gactggctct ccgccaagga gtgagtcgac ctgcaggcag cgcttggcgt  2520
cacccgcagt tcgtggtta ataagcttga cctgtgaagt gaaaaatggc gcacattgtg    2580 cgacatttt tttgtctgcc gtttaccgct actgcgtcac ggatctccac gcgccctgta    2640
gcggcgcatt aagcgcggcg ggtgtggtgg ttacgcgcag cgtgaccgct acacttgcca   2700
gcgccctagc gcccgctcct ttcgctttct tcccttcctt tctcgccacg ttcgccggct   2760
ttccccgtca agctctaaat cggggggctcc ctttagggggt tcccgatttta gtgcttttac  2820 gggacctcga acccaaaaaa ttgattagg                                    2849
```

<210> SEQ ID NO 26
<211> LENGTH: 830
<212> TYPE: PRT
<213> ORGANISM: Artificial
<220> FEATURE:
<221> NAME/KEY: MISC_FEATURE
<222> LOCATION: (1)..(830)
<223> OTHER INFORMATION: Mismatch extension mutant of Taq polymerase.

<400> SEQUENCE: 26

-continued

```
Gly Met Leu Pro Leu Phe Glu Pro Lys Gly Arg Val Leu Leu Val Asp
1               5                   10                  15

Gly His His Leu Ala Tyr Arg Thr Phe His Ala Leu Lys Gly Leu Thr
            20                  25                  30

Thr Ser Arg Gly Glu Pro Val Gln Ala Val Tyr Gly Phe Ala Lys Ser
        35                  40                  45

Leu Leu Lys Ala Leu Lys Glu Asp Gly Asp Ala Val Ile Val Val Phe
    50                  55                  60

Asp Ala Lys Ala Pro Ser Phe Arg His Glu Ala Tyr Gly Gly Tyr Lys
65                  70                  75                  80

Ala Ala Arg Ala Pro Thr Pro Glu Asp Phe Pro Arg Gln Leu Ala Leu
                85                  90                  95

Ile Lys Glu Leu Val Asp Leu Gly Leu Ala Arg Leu Glu Val Pro
                100                 105                 110

Gly Tyr Glu Ala Asp Asp Val Leu Ala Ser Leu Ala Lys Lys Ala Glu
            115                 120                 125

Lys Glu Gly Tyr Glu Val Arg Ile Leu Thr Ala Asp Lys Gly Leu Tyr
    130                 135                 140

Gln Leu Leu Ser Asp Arg Ile His Val Leu His Pro Glu Gly Tyr Leu
145                 150                 155                 160

Ile Thr Pro Ala Trp Leu Trp Glu Lys Tyr Gly Leu Arg Pro Asp Gln
                165                 170                 175

Trp Ala Asp Tyr Arg Ala Leu Thr Gly Asp Glu Ser Asp Asn Leu Pro
            180                 185                 190

Gly Val Lys Gly Ile Gly Glu Lys Thr Ala Arg Lys Leu Leu Glu Glu
        195                 200                 205

Trp Gly Ser Leu Glu Ala Leu Leu Lys Asn Leu Asp Arg Leu Lys Pro
210                 215                 220

Ala Ile Arg Glu Lys Ile Leu Ala His Met Asp Asp Leu Lys Leu Ser
225                 230                 235                 240

Trp Asp Leu Ala Lys Val Arg Thr Asp Leu Pro Leu Glu Val Asp Phe
                245                 250                 255

Ala Lys Arg Arg Glu Pro Asp Arg Glu Arg Leu Arg Ala Phe Leu Glu
            260                 265                 270

Arg Leu Glu Phe Gly Ser Leu Leu His Glu Phe Gly Leu Leu Glu Ser
        275                 280                 285

Pro Lys Ala Leu Glu Glu Ala Pro Trp Pro Pro Glu Gly Ala Phe
    290                 295                 300

Val Gly Phe Val Leu Ser Arg Arg Glu Pro Met Trp Ala Asp Leu Leu
305                 310                 315                 320

Ala Leu Ala Ala Ala Arg Gly Gly Arg Val His Arg Ala Pro Glu Pro
                325                 330                 335

Tyr Lys Ala Leu Arg Asp Leu Lys Glu Ala Arg Gly Leu Leu Ala Lys
            340                 345                 350

Asp Leu Ser Val Leu Ala Leu Arg Glu Gly Leu Gly Leu Pro Pro Gly
        355                 360                 365

Asp Asp Pro Met Leu Leu Ala Tyr Leu Leu Asp Pro Ser Asn Thr Thr
    370                 375                 380

Pro Glu Gly Val Ala Arg Arg Tyr Gly Gly Glu Trp Thr Glu Glu Ala
385                 390                 395                 400

Gly Glu Arg Ala Ala Leu Ser Glu Arg Leu Phe Ala Asn Leu Trp Gly
                405                 410                 415

Arg Leu Glu Gly Glu Glu Arg Leu Leu Trp Leu Tyr Arg Glu Val Glu
```

-continued

```
            420             425             430
Arg Pro Leu Ser Ala Val Leu Ala His Met Glu Ala Thr Gly Val Arg
            435             440             445
Leu Asp Val Ala Tyr Leu Arg Ala Leu Ser Leu Glu Val Ala Glu Glu
            450             455             460
Ile Ala Arg Leu Glu Ala Glu Val Phe Arg Leu Ala Gly His Pro Phe
465             470             475             480
Asn Leu Asn Ser Arg Asp Gln Leu Glu Arg Val Leu Phe Asp Glu Leu
            485             490             495
Gly Leu Pro Ala Ile Gly Lys Thr Glu Lys Thr Gly Lys Arg Ser Thr
            500             505             510
Ser Ala Ala Val Leu Gly Ala Leu Arg Glu Ala His Pro Ile Val Glu
            515             520             525
Lys Ile Leu Gln Tyr Arg Glu Leu Thr Lys Leu Lys Ser Thr Tyr Ile
            530             535             540
Asp Pro Leu Pro Asp Leu Ile His Pro Arg Thr Gly Arg Leu His Thr
545             550             555             560
Arg Phe Asn Gln Thr Ala Thr Ala Thr Gly Arg Leu Ser Ser Ser Asp
            565             570             575
Pro Asn Leu Gln Asn Ile Pro Val Arg Thr Pro Leu Gly Gln Arg Ile
            580             585             590
Arg Arg Ala Phe Ile Ala Glu Glu Gly Trp Leu Leu Val Val Leu Asp
            595             600             605
Tyr Ser Gln Ile Glu Leu Arg Val Leu Ala His Leu Ser Gly Asp Glu
            610             615             620
Asn Leu Ile Arg Val Phe Gln Glu Gly Arg Asp Ile His Thr Glu Thr
625             630             635             640
Ala Ser Trp Met Phe Gly Val Pro Arg Glu Ala Val Asp Pro Leu Met
            645             650             655
Arg Arg Ala Ala Lys Thr Ile Asn Phe Gly Val Leu Tyr Gly Met Ser
            660             665             670
Ala His Arg Leu Ser Gln Glu Leu Ala Ile Pro Tyr Glu Glu Ala Gln
            675             680             685
Ala Phe Ile Glu Arg Tyr Phe Gln Ser Phe Pro Lys Val Arg Ala Trp
            690             695             700
Ile Glu Lys Thr Leu Glu Glu Gly Arg Arg Arg Gly Tyr Val Glu Thr
705             710             715             720
Leu Phe Gly Arg Arg Arg Tyr Val Pro Asp Leu Glu Ala Arg Val Lys
            725             730             735
Ser Val Arg Gly Ala Ala Glu Arg Met Ala Phe Asn Met Pro Val Gln
            740             745             750
Gly Thr Ala Ala Asp Leu Met Lys Leu Ala Met Val Lys Leu Phe Pro
            755             760             765
Arg Leu Glu Glu Met Gly Ala Arg Met Leu Leu Gln Val His Asp Glu
            770             775             780
Leu Val Leu Glu Ala Pro Lys Glu Arg Ala Glu Ala Val Ala Arg Leu
785             790             795             800
Ala Lys Glu Val Met Glu Gly Val Tyr Pro Leu Ala Val Pro Leu Glu
            805             810             815
Val Glu Val Gly Ile Gly Glu Asp Trp Leu Ser Ala Lys Glu
            820             825             830

<210> SEQ ID NO 27
```

<211> LENGTH: 2484
<212> TYPE: DNA
<213> ORGANISM: Artificial
<220> FEATURE:
<221> NAME/KEY: misc_feature
<222> LOCATION: (1)..(2484)
<223> OTHER INFORMATION: Mismatch extension mutant of Taq polymerase.

<400> SEQUENCE: 27

```
tctttatgag cccaagggcc gcgtcctcct ggtggacggc caccacctgg cctaccgcac      60
cttccacgcc ctgaagggcc tcaccaccag ccggggggag ccggtgcagg cggtctacgg     120
cttcgccaag agcctcctca aggccctcaa ggagggcggg gacgcggtga tcgtggtctt     180
tgacgccaag gcccctcct tcccccatga ggcctacggg gggtacaagg cgggccgggc      240
ccccacgccg gaggactttc cccgacaact cgccctcatc aaggagctgg tggacctcct     300
ggggctgacg cgcctcgagg tcccgggcta cgaggcggac gacgtcctgg ccagcctggc     360
caagaaggcg gaaaggagg gctacgaggt ccgcatcctc accgccgaca aagacccttta    420
ccagctcctt tccgaccgca tccacgtcct ccacccccgag gggtacctca tcaccccggc   480
ctggctttgg gaaaagtacg gcctgaggcc cgaccagtgg gccgactacc gggccctgac   540
cggggacgag tccgacaacc ttcccggggt caagggcatc ggggagaaga cggcgaggaa   600
gcttctggag gagtggggga gcctggaagc cctcctcaag aacctggacc ggctgaagcc   660
cgccatccgg gagaagatcc tggcccacat ggacgatctg aagctctcct gggaccgggc   720
caaggtgcgc accgacctgc ccctggaggt ggacttcgcc aaaaggcggg agcccgaccg   780
ggagaggctt agggcctttc tggagaggct tgagtttggc agcctcctcc acgagttcgg   840
ccttctggaa agcccaagg ccctggagga ggcccctgg ccccgccgg aaggggcctt      900
cgtgggcttt gtgctttccc gcaaggagcc catgtgggcc gatcttctag ccctggccgc   960
cgccagggg ggccgggtcc accgggcccc cgagccttat aaagccctcg ggacctgaa    1020
ggaggcgcgg gggcttctcg ccaaagacct gagcgttctg gccctgaggg aaggccttgg  1080
cctcccgccc gacgacgacc ccatgctcct cgcctacctc ctggaccctt ccaacaccac  1140
ccccgagggg gtgcccggc gctacggcgg ggagtggacg gaggagcgag gggagcgggc  1200
cgcccttttcc gagaggctct tcgccaacct gtggggagg cttgaggggg aggaaaggct  1260
cctttggctt taccgggagg tggagaggcc cctttccgct gtcctggccc acatggaggc  1320
cacggggtg cgcctggacg tggcctatct cagggccttg tccctggagg tggccgagga  1380
gatcgcccgc ctcgaggccg aggtcttccg cctggccggc caccccttca acctcaactc  1440
ccgggaccag ctggaaaggg tcctctttga cgagctaggg cttccgcca tcggcaagac   1500
ggagaagacc ggcaagcgct ccaccagcgc cgccgtcctg ggggccctcc gcgaggccca  1560
cccatcgtg gagaagatcc tgcagtaccg ggagctcacc aagctgaaga gcacctacat  1620
tgaccccttg ccggacctca tccaccccag gacgggccgc ctccacaccc gcttcaacca  1680
gacggccacg gccacgggca ggctaagtag ctccgatccc aacctccaga gcatccccgt  1740
ccgcaccccg cttgggcaga ggatccgccg ggccttcatc gccgaggagg ggtggctatt  1800
ggtggccctg gactatagcc agatagagct cagggtgctg gcccacctct ccggcgacga  1860
gaacctgatc cgggtcttcc aggagggcg ggacatccac acggagaccg ccagctggat  1920
gttcggcgtc cccggggagg ccgtggaccc cctgatgcgc cggcggcca agaccatcaa   1980
cttcggggtc ctctacggca tgtcggccca ccgcctctcc caggagctag ccatcccta   2040
cgaggaggcc caggccttca ttaagcgcta ctttcagagc ttccccaagg tgcgggcctg  2100
```

-continued

```
gattgagaag accctggagg agggcaggag gcggggtac gtggagaccc tcttcggccg    2160
ccgccgctac gtgccagacc tagaggcccg ggtgaagagc gtgcgggagc cggccgagcg    2220
catggccttc aacatgcccg tccagggtac cgccgccgac ctcatgaagc tggctatggt    2280
gaagctcttc cccaggctgg aggaaatggg ggccaggatg ctccttcagg tccacgacga    2340
gctggtcctc gaggccccaa agagagggc ggaggccgtg gcccggctgg ccaaggaggt    2400
catggagggg gtgtatcccc tggccgtgcc cctggaggtg gaggtgggga taggggagga    2460
ctggctctcc gccaaggagt gagt                                          2484
```

<210> SEQ ID NO 28
<211> LENGTH: 826
<212> TYPE: PRT
<213> ORGANISM: Artificial
<220> FEATURE:
<221> NAME/KEY: MISC_FEATURE
<222> LOCATION: (1)..(826)
<223> OTHER INFORMATION: Mismatch extension mutant of Taq polymerase.

<400> SEQUENCE: 28

```
Leu Tyr Glu Pro Lys Gly Arg Val Leu Leu Val Asp Gly His His Leu
1               5                   10                  15

Ala Tyr Arg Thr Phe His Ala Leu Lys Gly Leu Thr Thr Ser Arg Gly
            20                  25                  30

Glu Pro Val Gln Ala Val Tyr Gly Phe Ala Lys Ser Leu Leu Lys Ala
        35                  40                  45

Leu Lys Glu Gly Gly Asp Ala Val Ile Val Val Phe Asp Ala Lys Ala
    50                  55                  60

Pro Ser Phe Pro His Glu Ala Tyr Gly Gly Tyr Lys Ala Gly Arg Ala
65                  70                  75                  80

Pro Thr Pro Glu Asp Phe Pro Arg Gln Leu Ala Leu Ile Lys Glu Leu
                85                  90                  95

Val Asp Leu Leu Gly Leu Thr Arg Leu Glu Val Pro Gly Tyr Glu Ala
            100                 105                 110

Asp Asp Val Leu Ala Ser Leu Ala Lys Lys Ala Glu Lys Glu Gly Tyr
        115                 120                 125

Glu Val Arg Ile Leu Thr Ala Asp Lys Asp Leu Tyr Gln Leu Leu Ser
    130                 135                 140

Asp Arg Ile His Val Leu His Pro Glu Gly Tyr Leu Ile Thr Pro Ala
145                 150                 155                 160

Trp Leu Trp Glu Lys Tyr Gly Leu Arg Pro Asp Gln Trp Ala Asp Tyr
                165                 170                 175

Arg Ala Leu Thr Gly Asp Glu Ser Asp Asn Leu Pro Gly Val Lys Gly
            180                 185                 190

Ile Gly Glu Lys Thr Ala Arg Lys Leu Leu Glu Glu Trp Gly Ser Leu
        195                 200                 205

Glu Ala Leu Leu Lys Asn Leu Asp Arg Leu Lys Pro Ala Ile Arg Glu
    210                 215                 220

Lys Ile Leu Ala His Met Asp Asp Leu Lys Leu Ser Trp Asp Arg Ala
225                 230                 235                 240

Lys Phe Arg Thr Asp Leu Pro Leu Glu Val Asp Phe Ala Lys Arg Arg
                245                 250                 255

Glu Pro Asp Arg Glu Arg Leu Arg Ala Phe Leu Glu Arg Leu Glu Phe
            260                 265                 270

Gly Ser Leu Leu His Glu Phe Gly Leu Leu Glu Ser Pro Lys Ala Leu
```

```
                275                 280                 285
Glu Glu Ala Pro Trp Pro Pro Glu Gly Ala Phe Val Gly Phe Val
        290                 295                 300
Leu Ser Arg Lys Glu Pro Met Trp Ala Asp Leu Leu Ala Leu Ala Ala
305                 310                 315                 320
Ala Arg Gly Gly Arg Val His Arg Ala Pro Glu Pro Tyr Lys Ala Leu
                325                 330                 335
Gly Asp Leu Lys Glu Ala Arg Gly Leu Leu Ala Lys Asp Leu Ser Val
                340                 345                 350
Leu Ala Leu Arg Glu Gly Leu Gly Leu Pro Pro Asp Asp Pro Met
            355                 360                 365
Leu Leu Ala Tyr Leu Leu Asp Pro Ser Asn Thr Thr Pro Glu Gly Val
        370                 375                 380
Ala Arg Arg Tyr Gly Gly Glu Trp Thr Glu Glu Ala Gly Glu Arg Ala
385                 390                 395                 400
Ala Leu Ser Glu Arg Leu Phe Ala Asn Leu Trp Gly Arg Leu Glu Gly
                405                 410                 415
Glu Glu Arg Leu Leu Trp Leu Tyr Arg Glu Val Glu Arg Pro Leu Ser
                420                 425                 430
Ala Val Leu Ala His Met Glu Ala Thr Gly Val Arg Leu Asp Val Ala
            435                 440                 445
Tyr Leu Arg Ala Leu Ser Leu Glu Val Ala Glu Glu Ile Ala Arg Leu
        450                 455                 460
Glu Ala Glu Val Phe Arg Leu Ala Gly His Pro Phe Asn Leu Asn Ser
465                 470                 475                 480
Arg Asp Gln Leu Glu Arg Val Leu Phe Asp Glu Leu Gly Leu Pro Ala
                485                 490                 495
Ile Gly Lys Thr Glu Lys Thr Gly Lys Arg Ser Thr Ser Ala Ala Val
                500                 505                 510
Leu Gly Ala Leu Arg Glu Ala His Pro Ile Val Glu Lys Ile Leu Gln
            515                 520                 525
Tyr Arg Glu Leu Thr Lys Leu Lys Ser Thr Tyr Ile Asp Pro Leu Pro
        530                 535                 540
Asp Leu Ile His Pro Arg Thr Gly Arg Leu His Thr Arg Phe Asn Gln
545                 550                 555                 560
Thr Ala Thr Ala Thr Gly Arg Leu Ser Ser Ser Asp Pro Asn Leu Gln
                565                 570                 575
Ser Ile Pro Val Arg Thr Pro Leu Gly Gln Arg Ile Arg Arg Ala Phe
                580                 585                 590
Ile Ala Glu Glu Gly Trp Leu Leu Val Ala Leu Asp Tyr Ser Gln Ile
            595                 600                 605
Glu Leu Arg Val Leu Ala His Leu Ser Gly Asp Glu Asn Leu Ile Arg
        610                 615                 620
Val Phe Gln Glu Gly Arg Asp Ile His Thr Glu Thr Ala Ser Trp Met
625                 630                 635                 640
Phe Gly Val Pro Arg Glu Ala Val Asp Pro Leu Met Arg Arg Ala Ala
                645                 650                 655
Lys Thr Ile Asn Phe Gly Val Leu Tyr Gly Met Ser Ala His Arg Leu
                660                 665                 670
Ser Gln Glu Leu Ala Ile Pro Tyr Glu Glu Ala Gln Ala Phe Ile Lys
            675                 680                 685
Arg Tyr Phe Gln Ser Phe Pro Lys Val Arg Ala Trp Ile Glu Lys Thr
        690                 695                 700
```

-continued

```
Leu Glu Glu Gly Arg Arg Arg Gly Tyr Val Glu Thr Leu Phe Gly Arg
705                 710                 715                 720

Arg Arg Tyr Val Pro Asp Leu Glu Ala Arg Val Lys Ser Val Arg Glu
            725                 730                 735

Pro Ala Glu Arg Met Ala Phe Asn Met Pro Val Gln Gly Thr Ala Ala
            740                 745                 750

Asp Leu Met Lys Leu Ala Met Val Lys Leu Phe Pro Arg Leu Glu Glu
            755                 760                 765

Met Gly Ala Arg Met Leu Leu Gln Val His Asp Glu Leu Val Leu Glu
            770                 775                 780

Ala Pro Lys Glu Arg Ala Glu Ala Val Ala Arg Leu Ala Lys Glu Val
785                 790                 795                 800

Met Glu Gly Val Tyr Pro Leu Ala Val Pro Leu Glu Val Glu Val Gly
                805                 810                 815

Ile Gly Glu Asp Trp Leu Ser Ala Lys Glu
                820                 825
```

COMPARTMENTALISED SELF REPLICATION METHOD FOR IN VITRO EVOLUTION OF MOLECULAR LIBRARIES

This application is a continuation-in-part of international application PCT/GB01/04108, filed Sep. 13, 2001, which claims the priority of each of Great Britain application GB 0022458.4, filed Sep. 13, 2000, U.S. provisional application No. 60/283,771, filed Apr. 13, 2001 and U.S. provisional application No. 60/285,501, filed Apr. 20, 2001. Each of these priority documents is expressly incorporated herein in its entirety, including tables and drawings.

FIELD OF THE INVENTION

The present invention relates to methods for use in in vitro evolution of molecular libraries. In particular, the present invention relates to methods of selecting nucleic acids encoding gene products in which the nucleic acid and the activity of the encoded gene product are linked by compartmentalisation.

BACKGROUND TO THE INVENTION

Evolution requires the generation of genetic diversity (diversity in nucleic acid) followed by the selection of those nucleic acids which encode beneficial characteristics. Because the activity of the nucleic acids and their encoded gene product are physically linked in biological organisms (the nucleic acids encoding the molecular blueprint of the cells in which they are confined), alterations in the genotype resulting in an adaptive change(s) of phenotype produce benefits for the organism resulting in increased survival and offspring. Multiple rounds of mutation and selection can thus result in the progressive enrichment of organisms (and the encoding genotype) with increasing adaptation to a given selection condition. Systems for rapid evolution of nucleic acids or proteins in vitro must mimic this process at the molecular level in that the nucleic acid and the activity of the encoded gene product must be linked and the activity of the gene product must be selectable.

In vitro selection technologies are a rapidly expanding field and often prove more powerful than rational design to obtain biopolymers with desired properties. In the past decade selection experiments, using e.g. phage display or SELEX technologies have yielded many novel polynucleotide and polypeptide ligands. Selection for catalysis has proved harder. Strategies have included binding of transition state analogues, covalent linkage to suicide inhibitors, proximity coupling and covalent product linkage. Although these approaches focus only on a particular part of the enzymatic cycle, there have been some successes. Ultimately however it would be desirable to select directly for catalytic turnover. Indeed, simple screening for catalytic turnover of fairly small mutant libraries has been rather more successful than the various selection approaches and has yielded some catalysts with greatly improved catalytic rates.

While polymerases are a prerequisite for technologies that define molecular biology, i.e. site-directed mutagenesis, cDNA cloning and in particular Sanger sequencing and PCR, they often suffer from serious shortcomings due to the fact that they are made to perform tasks for which nature has not optimized them. Few attempts appear to have been made to improve the properties of polymerases available from nature and to tailor them for specific applications by protein engineering. Technical advances have been largely peripheral, and include the use of polymerases from a wider range of organisms, buffer and additive systems as well as enzyme blends.

Attempts to improve the properties of polymerases have traditionally relied on protein engineering. For example, variants of Taq polymerase (for example, Stoffel fragment and Klentaq) have been generated by full or partial deletion of its 5'-3' exonuclease domain and show improved thermostability and fidelity although at the cost of reduced processivity (Barnes 1992, *Gene* 112, 29-35, Lawyer et al., 1993, *PCR Methods and Applications* 2, 275). In addition, the availability of high-resolution structures for proteins has allowed the rational design of mutants with improved properties (for example, Taq mutants with improved properties of dideoxynucleotide incorporation for cycle sequencing, Li et al., 1999, *Proc. Natl. Acad. Sci. USA* 96, 9491). In vivo genetic approaches have also been used for protein design, for example by complementation of a polA strain to select for active polymerases from repertoires of mutant polymerases (Suzuki et al., 1996 *Proc. Natl. Acad. Sci. USA* 93, 9670). However, the genetic complementation approach is limited in the properties that can be selected for.

Recent advances in molecular biology have allowed some molecules to be co-selected in vitro according to their properties along with the nucleic acids that encode them. The selected nucleic acids can subsequently be cloned for further analysis or use, or subjected to additional rounds of mutation and selection. Common to these methods is the establishment of large libraries of nucleic acids. Molecules having the desired characteristics (activity) can be isolated through selection regimes that select for the desired activity of the encoded gene product, such as a desired biochemical or biological activity, for example binding activity.

WO99/02671 describes a method for isolating one or more genetic elements encoding a gene product having a desired activity. Genetic elements are first compartmentalised into microcapsules, and then transcribed and/or translated to produce their respective gene products (RNA or protein) within the microcapsules. Alternatively, the genetic elements are contained within a host cell in which transcription and/or translation (expression) of the gene product takes place and the host cells are first compartmentalised into microcapsules. Genetic elements which produce gene product having desired activity are subsequently sorted. The method described in WO99/02671 relies on the gene product catalytically modifying the microcapsule or the genetic element (or both), so that enrichment of the modified entity or entities enables selection of the desired activity.

SUMMARY OF THE INVENTION

According to a first aspect of the present invention, we provide a method of selecting a nucleic acid-processing (NAP) enzyme, the method comprising the steps of: (a) providing a pool of nucleic acids comprising members encoding a NAP enzyme or a variant of the NAP enzyme; (b) subdividing the pool of nucleic acids into compartments, such that each compartment comprises a nucleic acid member of the pool together with the NAP enzyme or variant encoded by the nucleic acid member; (c) allowing nucleic acid processing to occur; and (d) detecting processing of the nucleic acid member by the NAP enzyme.

There is provided, according to a second aspect of the present invention, a method of selecting an agent capable of modifying the activity of a NAP enzyme, the method comprising the steps of: (a) providing a NAP enzyme; (b) providing a pool of nucleic acids comprising members encoding one or more candidate agents; (c) subdividing the pool of nucleic acids into compartments, such that each compartment comprises a nucleic acid member of the pool, the agent encoded by the nucleic acid member, and the NAP enzyme; and (d) detecting processing of the nucleic acid member by the NAP enzyme.

Preferably, the agent is a promoter of NAP enzyme activity. The agent may be an enzyme, preferably a kinase or a phosphorylase, which is capable of acting on the NAP enzyme to modify its activity. The agent may be a chaperone involved in the folding or assembly of the NAR enzyme or required for the maintenance of replicase function (e.g. telomerase, HSP 90). Alternatively, the agent may be a polypeptide or polynucleotide involved in a metabolic pathway, the pathway having as an end product a substrate which is involved in a replication reaction. The agent may moreover be any enzyme which is capable of catalysing a reaction that modifies an inhibiting agent (natural or unnatural) of the NAP enzyme in such a way as to reduce or abolish its inhibiting activity. Finally the agent may promote NAP activity in a non-catalytic way, e.g. by association with the NAP enzyme or its substrate etc. (e.g. processivity factors in the case of DNA polymerases, e.g. T7 DNA polymerase & thioredoxin).

We provide, according to a third aspect of the present invention, a method of selecting a pair of polypeptides capable of stable interaction, the method comprising: (a) providing a first nucleic acid and a second nucleic acid, the first nucleic acid encoding a first fusion protein comprising a first subdomain of a NAP enzyme fused to a first polypeptide, the second nucleic acid encoding a second fusion protein comprising a second subdomain of a NAP enzyme fused to a second polypeptide; in which stable interaction of the first and second NAP enzyme subdomains generates NAP enzyme activity, and in which at least one of the first and second nucleic acids is provided in the form of a pool of nucleic acids encoding variants of the respective first and/or second polypeptide(s); (b) subdividing the pool or pools of nucleic acids into compartments, such that each compartment comprises a first nucleic acid and a second nucleic acid together with respective fusion proteins encoded by the first and second nucleic acids; (c) allowing the first polypeptide to bind to the second polypeptide, such that binding of the first and second polypeptides leads to stable interaction of the NAP enzyme subdomains to generate NAP enzyme activity; and (d) detecting processing of at least one of the first and second nucleic acids by the NAP enzyme.

Moreover, the NAP enzyme domains referred to in (a) above may be replaced with domains of a polypeptide capable of modifying the activity of NAP enzymes, as discussed in the second aspect of the present invention, and NAP enzyme activity used to select such modifying polypeptides having desired properties.

Preferably, each of the first and second nucleic acids is provided from a pool of nucleic acids.

Preferably, the first and second nucleic acids are linked either covalently (e.g. as part of the same template molecule) or non-covalently (e.g. by tethering onto beads etc.).

NAP enzymes may for example be polypeptide or ribonucleic acid enzyme molecules. In a highly preferred embodiment, the NAP enzyme according to the invention is a replicase enzyme, i.e. an enzyme, which is capable of amplifying nucleic acid from a template, such as for example a polymerase enzyme (or ligase). The invention is described herein below with specific reference to replicases; however, it will be understood by those skilled in the art that the invention is equally applicable to other NAP enzymes, such as telomerases and helicases, as further set out below, which process nucleic acids in ways not limited to amplification but which are nevertheless selectable by detecting nucleic acid amplification, i.e. which promote replication indirectly.

In a preferred embodiment of the invention, amplification of the nucleic acid results from more than one round of nucleic acid replication. Preferably, the amplification of the nucleic acid is an exponential amplification.

The amplification reaction is preferably selected from the following: a polymerase chain reaction (PCR), a reverse transcriptase-polymerase chain reaction (RT-PCR), a nested PCR, a ligase chain reaction (LCR), a transcription-based amplification system (TAS), a self-sustaining sequence replication (3SR), NASBA, a transcription-mediated amplification reaction (TMA), and a strand-displacement amplification (SDA).

In a highly preferred embodiment, the post-amplification copy number of the nucleic acid member is substantially proportional to the activity of the replicase, the activity of a requisite agent, or the binding affinity and/or binding kinetics of the first and second polypeptides.

Nucleic acid replication may be detected by assaying the copy number of the nucleic acid member. Alternatively, or in addition, nucleic acid replication may be detected by determining the activity of a polypeptide encoded by the nucleic acid member.

In a highly preferred embodiment, the conditions in the compartment are adjusted to select for a replicase or agent active under such conditions, or a pair of polypeptides capable of stable interaction under such conditions.

The replicase preferably has polymerase, reverse transcriptase or ligase activity.

The polypeptide may be provided from the nucleic acid by in vitro transcription and translation. Alternatively, the polypeptide may be provided from the nucleic acid in vivo in an expression host.

In a preferred embodiment, the compartments consist of the encapsulated aqueous component of a water-in-oil emulsion. The water-in-oil emulsion is preferably produced by emulsifying an aqueous phase with an oil phase in the presence of a surfactant comprising 4.5% v/v Span 80, 0.4% v/v Tween 80 and 0.1% v/v Triton X100, or a surfactant comprising Span 80, Tween 80 and Triton X100 in substantially the same proportions. Preferably, the water:oil phase ratio is 1:2, which leads to adequate droplet size. Such emulsions have a higher thermal stability than more oil-rich emulsions.

As a fourth aspect of the present invention, there is provided a replicase enzyme identified by a method according to any preceding claim. Preferably, the replicase enzyme has a greater thermostability than a corresponding unselected enzyme More preferably, the replicase enzyme is a Taq polymerase having more than 10 times increased half-life at 97.5° C. when compared to wild-type Taq polymerase.

The replicase enzyme may have a greater tolerance to heparin than a corresponding unselected enzyme. Preferably, the replicase enzyme is a Taq polymerase active at a concentration of 0.083 units/µl or more of heparin.

The replicase enzyme may be capable of extending a primer having a 3' mismatch. Preferably, the 3' mismatch is a 3 purine-purine mismatch or a 3' pyrimidine-pyrimidine mismatch. More preferably, the 3' mismatch is an A-G mismatch or the 3' mismatch is a C-C mismatch.

We provide, according to a fifth aspect of the present invention, a Taq polymerase mutant comprising the mutations (amino acid substitutions): F73S, R205K, K219E, M236T, E434D and A608V.

The present invention, in a sixth aspect, provides a Taq polymerase mutant comprising the mutations (amino acid substitutions): K225E, E388V, K540R, D578G, N583S and M747R.

The present invention, in a seventh aspect, provides a Taq polymerase mutant comprising the mutations (amino acid substitutions): G84A, D144G, K314R, E520G, A608V, E742G.

The present invention, in a eighth aspect, provides a Taq polymerase mutant comprising the mutations (amino acid substitutions): D58G, R74P, A109T, L245R, R343G, G370D, E520G, N583S, E694K, A743P.

In a ninth aspect of the present invention, there is provided a water-in-oil emulsion obtainable by emulsifying an aqueous phase with an oil phase in the presence of a surfactant comprising 4.5% v/v Span 80, 0.4% v/v Tween 80 and 0.1% v/v Triton X100, or a surfactant comprising Span 80, Tween 80 and Triton X100 in substantially the same proportions. Preferably, the water:oil phase ratio is 1:2. This ratio appears to permit diffusion of dNTPs (and presumably other small molecules) between compartments at higher temperatures, which is beneficial for some applications but not for others. Diffusion can be controlled by increasing water:oil phase ratio to 1:4.

In another aspect, the NAP enzyme is a replicase enzyme that has an enhanced capability to replicate substrates 23 kb in size or greater in the absence of processivity factors or a 3'-5' exonuclease proof-reading domain.

As used herein, the phrase "variant of a nucleic acid processing enzyme" means a NAP enzyme with an amino acid sequence (for polypeptide enzymes) or nucleotide sequence (for ribozymes) differs from a naturally occurring sequence of that NAP enzyme by at least one amino acid (for polypeptide enzymes) or nucleotide (for ribozymes). A variant NAP enzyme catalyzes a reaction catalyzed by the corresponding wild-type NAP enzyme.

As used herein, the phrase "modifying the activity of a NAP enzyme" means causing the activity of a NAP enzyme to increase or decrease, or changing another aspect of the enzyme's activity, such as substrate identity or substrate specificity, the reaction catalyzed, cofactor dependence, optimal salt, buffer or temperature conditions, temperature stability, proofreading capacity, interaction with other proteins or enzymes, or sensitivity to inhibition.

As used herein, the phrase "enhancing the activity of a NAP enzyme" or "increasing the activity of a NAP enzyme" means increasing the amount of a product of a reaction catalyzed by a NAP enzyme in the presence of an enhancing stimulus under a particular set of conditions by at least 10% relative to the amount formed under similar conditions in the absence of the enhancing stimulus.

As used herein, the phrase "promoter of NAP enzyme activity" refers to an agent that increases the activity of a given NAP enzyme.

As used herein, the phrase "polypeptide that produces a substrate in a nucleic acid processing reaction" means a polypeptide enzyme that catalyzes a reaction resulting in the production of a substrate for a NAP enzyme. A non-limiting example of a polypeptide that produces a substrate in a nucleic acid processing reaction is a nucleoside diphosphate kinase, which catalyzes the phosphorylation of deoxynucleoside diphosphates to deoxynucleoside triphosphates, which are substrates for NAP enzymes such as DNA polymerases.

As used herein, the phrase "polypeptide that consumes an inhibitor in a nucleic acid processing reaction" means a polypeptide enzyme that catalyzes a reaction resulting in the inactivation of an inhibitor of a NAP enzyme reaction. A non-limiting example of a polypeptide that consumes an inhibitor in a nucleic acid processing reaction is a heparinase. Heparin is an inhibitor of polymerase activity, and heparinase enzymes break down heparin, thereby consuming the inhibitor molecule.

As used herein, the phrase "polypeptide that modifies a nucleotide primer or nucleoside triphosphate substrate used in a nucleic acid processing reaction" means a polypeptide enzyme that catalyzes a chemical modification of a nucleotide primer or a nucleoside triphosphate substrate for a NAP enzyme, the modification permitting the nucleotide primer or nucleoside triphosphate to participate in a reaction catalyzed by the NAP enzyme.

As used herein, the phrase "substrate appendage added to a nucleotide primer or nucleoside triphosphate" means a chemical moiety, added to a nucleotide primer or nucleoside triphosphate, that is acted upon by an enzyme that "modifies a nucleotide primer or nucleoside triphosphate" as that term is defined herein above. Most often, such a "substrate portion" is inhibitory to the activity of a NAP enzyme on that primer or nucleoside triphosphate.

As used herein, the phrase "stable interaction" means a physical interaction between two polypeptides. As the term is used herein, a "stable interaction" between two polypeptide sequences fused to respective, separate NAP enzyme subdomain polypeptides is an interaction that permits the respective NAP enzyme subdomains that do not alone catalyze a reaction catalyzed by the intact NAP enzyme to together catalyze a reaction that is catalyzed by the intact NAP enzyme.

As used herein, the phrase "subdomain of a NAP enzyme" means a portion of a NAP enzyme polypeptide, which portion, separate and on its own does not have catalytic activity, but which, when brought into physical contact with another polypeptide comprising another portion of that NAP enzyme, reconstitutes a functional NAP enzyme capable of catalyzing a reaction catalyzed by the intact NAP enzyme that is not catalyzed by either portion of the NAP enzyme on its own. Non-limiting examples of subdomains of a NAP enzyme are described by Vainshtein et al., 1996, Protein Science 5: 1785.

As used herein, the phrase "stable interaction of first and second NAP subdomains generates processing activity" means that the physical interaction of two separate subdomains of a NAP enzyme, as the term is defined herein, reconstitutes a catalytic activity of the intact NAP enzyme that is not possessed by either the first or second NAP subdomains on their own.

As used herein, the phrase "subdomain of a polypeptide that enhances the activity of a NAP enzyme" means a portion of a polypeptide that, when intact, enhances the activity of a NAP enzyme. As it is used herein, the "subdomain" of such a polypeptide is a portion that does not, on its own, enhance the activity of a NAP enzyme, but when in physical contact with another portion of that enhancing polypeptide, reconstitutes NAP activity enhancement.

As used herein, the phrase "stable folding" means that a polypeptide assumes a tertiary structure that exhibits a sigmoidal thermal denaturation curve. A "a non-folded or improperly folded polypeptide" is non-functional relative to a properly folded polypeptide and tends to aggregate and precipitate.

As used herein, the phrase "poorly folding polypeptide" means a polypeptide that tends to aggregate and precipitate unless it is permitted to fold in the presence of a chaperone. Fusion of a "poorly folding polypeptide" will inhibit the activity of a NAP enzyme unless the fusion polypeptide is folded in the presence of a chaperone.

As used herein, the phrase "replication of a nucleic acid member" means the template-directed addition of at least one nucleotide to a nucleic acid substrate of a NAP enzyme. That is, "replication" as the term is used herein encompasses template-directed replication of an entire nucleic acid molecule, as well template-directed replication of less than an entire nucleic acid molecule.

As used herein, the term "proportional" refers to a direct numerical relationship between two measurable quantities, such as the activity of an enzyme and the amount of product of the reaction catalyzed by that enzyme. The phrase "substantially proportional" encompasses a proportional relationship between two measurable quantities as well as a relationship that varies from direct proportion by 20% or less. For example, where a doubling of the rate of enzyme activity would result in a doubling of the amount of product produced per unit time in a directly proportional relationship (100% increase in each of enzyme activity and product produced), an increase of 80% to 120% would be considered "substantially proportional."

As used herein, the phrase "tagging of the nucleic acid member" means covalently or non-covalently appending a detectable moiety to a nucleic acid. Non-limiting examples of tags include radiolabels, fluorescent moieties, antibodies and stretches of nucleotide sequence that permit detection with a nucleic acid probe, antibody, specific binding partner or enzyme.

As used herein, the phrase "unnatural 3' base" means a nitrogenous base structure, comprised by the 3' nucleotide of a nucleic acid, that does not occur on a nucleotide in nature.

As used herein, the phrase "enhanced capability to replicate substrates 23 kb in size" means that a mutated replicase enzyme replicates a substrate 23 kb in size at least 10% more efficiently than the non-mutated version of that replicase enzyme.

As used herein, the term "processivity factor" means a polypeptide that increases the amount of polymerization catalyzed by a polymerase each time the polymerase initiates. Processivity factors are well known in the art. Non-limiting examples of processivity factors include thioredoxin (increases processivity of bacteriophage T7 polymerase), PCNA (increases processivity of eukaryotic Pol δ) and the β subunit of DNA Pol III (DnaN; increases the processivity of bacterial Pol III).

Figure 1A:
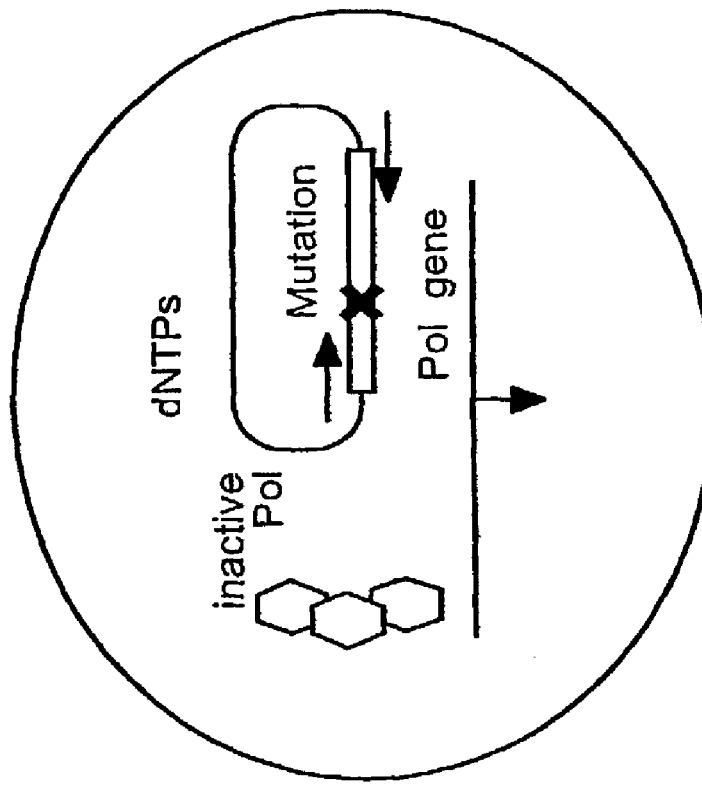
FIG. 1A is a diagram showing an embodiment of a method according to the present invention as applied to selection of a self-evolving polymerase, in which gene copy number is linked to enzymatic turnover.
Figure 1A:
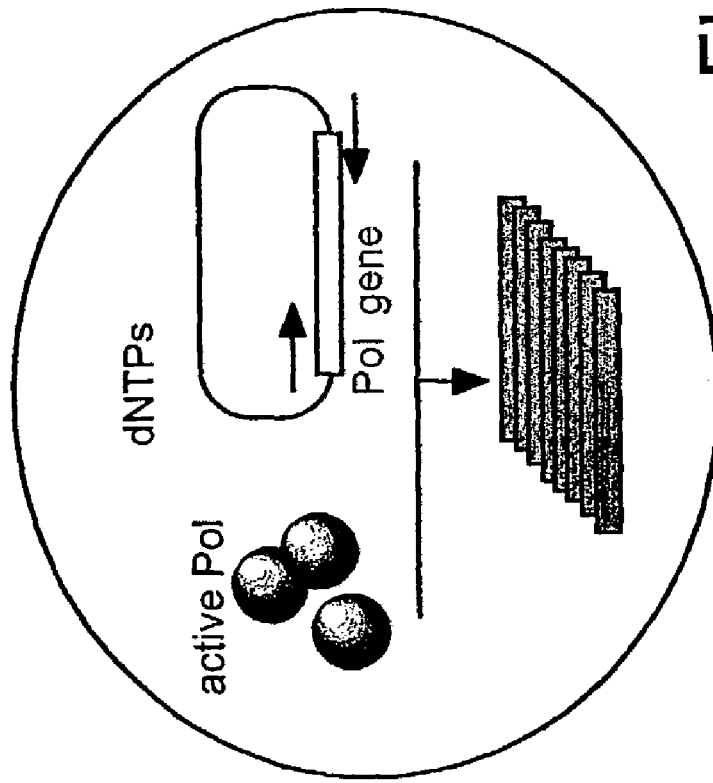

Nucleoside diphosphate kinase (ndk) is expressed from a plasmid and converts deoxinucleoside diphosphates which are not substrates for Taq polymerase into deoxinucleoside triphosphates which are. As soon as ndk has produced sufficient amounts of substrate, Taq can replicate the ndk gene.

B: Bacterial cells expressing wild-type ndk (0.8 kb) or an inactive truncated fragment (0.5 kb) are mixed 1:1 prior to emulsification. In solution, the shorter truncated fragment is amplified preferentially. In emulsion, there is predominantly amplification of the wt ndk gene and only weak amplification of the truncated fragment (arrow) indicating that in emulsion only active ndk genes producing substrate are amplified. M: HaeIII φX174 marker.

DETAILED DESCRIPTION OF THE INVENTION

The practice of the present invention will employ, unless otherwise indicated, conventional techniques of chemistry, molecular biology, microbiology, recombinant DNA and immunology, which are within the capabilities of a person of ordinary skill in the art. Such techniques are explained in the literature. See, e.g., J. Sambrook, E. F. Fritsch, and T. Maniatis, 1989, Molecular Cloning: A Laboratory Manual, Second Edition, Books 1-3, Cold Spring Harbor Laboratory Press; B. Roe, J. Crabtree, and A. Kahn, 1996, DNA Isolation and Sequencing: Essential Techniques, John Wiley & Sons; J. M. Polak and James O'D. McGee, 1990, In situ Hybridization: Principles and Practice; Oxford University Press; M. J. Gait (Editor), 1984, Oligonucleotide Synthesis: A Practical Approach, Irl Press; and, D. M. J. Lilley and J. E. Dahlberg, 1992, Methods of Enzymology: DNA Structure Part A: Syn- Compartmentalised Self Replication Our invention describes a novel selection technology, which we call CSR (compartmentalised self-replication). It has the potential to be expanded into a generic selection system for catalysis as well as macromolecular interactions.

In its simplest form CSR involves the segregation of genes coding for and directing the production of DNA polymerases within discrete, spatially separated, aqueous compartments of a novel heat-stable water-in-oil emulsion. Provided with nucleotide triphosphates and appropriate flanking primers, polymerases replicate only their own genes. Consequently, only genes encoding active polymerases are replicated, while inactive variants that cannot copy their genes disappear from the gene pool. By analogy to biological systems, among differentially adapted variants, the most active (the fittest) produce the most "offspring", hence directly correlating post-selection copy number with enzymatic turnover.

CSR is not limited to polymerases but can be applied to a wide variety of enzymatic transformations, built around the "replicase engine". For example, an enzyme "feeding" a polymerase which in turn replicates its gene may be selected. More complicated coupled cooperative reaction schemes can be envisioned in which several enzymes either produce replicase substrates or consume replicase inhibitors.

Polymerases occupy a central role in genome maintenance, transmission and expression of genetic information. Polymerases are also at the heart of modern biology, enabling core technologies such as mutagenesis, cDNA libraries, sequencing and the polymerase chain reaction (PCR). However, commonly used polymerases frequently suffer from serious shortcomings as they are used to perform tasks for which nature had not optimized them. Indeed, most advances have been peripheral, including the use of polymerases from different organisms, improved buffer and additive systems as well as enzyme blends. CSR is a novel selection system ideally suited for the isolation of "designer" polymerases for specific applications. Many features of polymerase function are open to "improvement" (e.g. processivity, substrate selection etc.). Furthermore, CSR is a tool to study polymerase function, e.g. to probe immutable regions, study components of the replisome etc. Moreover, CSR may be used for shotgun functional cloning of polymerases, straight from diverse, uncultured microbial populations.

CSR represents a novel principle of repertoire selection of polypeptides. Previous approaches have featured various "display" methods in which phenotype and genotype (polypeptide and encoding gene) are linked as part of a "genetic package" containing the encoding gene and displaying the polypeptide on the "outside". Selection occurs via a step of affinity purification after which surviving clones are grown (amplified) in cells for further rounds of selection (with resulting biases in growth distorting selections). Further distortions result from differences in the display efficiencies between different polypeptides.

In another set of methods both polypeptide and encoding gene(s) are "packaged" within a cell. Selection occurs in vivo through the polypeptide modifying the cell in such a way that it acquires a novel phenotype, e.g. growth in presence of an antibiotic. As the selection pressure is applied on whole cells, such approaches tend to be prone to the generation of false positives. Furthermore, in vivo complementation strategies are limited in that selection conditions, and hence selectable phenotypes, cannot be freely chosen and are further constrained by limits of host viability.

In CSR, there is no direct physical linkage (covalent or non-covalent) between polypeptide and encoding gene. More copies of successful genes are "grown" directly and in vitro as part of the selection process.

CSR is applicable to a broad spectrum of DNA and RNA polymerases, indeed to all polypeptides (or polynucleotides) involved in replication or gene expression. CSR can also be applied to DNA and RNA ligases assembling their genes from oligonucleotide fragments.

CSR is the only selection system in which the turnover rate of an enzyme is directly linked to the post-selection copy-number of its encoding gene.

There is great interest in polynucleotide polymers with altered bases, altered sugars or even backbone chemistries. However, solid-phase synthesis can usually only provide relatively short polymers and naturally occurring polymerases unsurprisingly incorporate most analogues poorly. CSR is ideally suited for the selection of polymerases more tolerant of unnatural substrates in order to prepare polynucleotide polymers with novel properties for chemistry, biology and nanotechnology (e.g. DNA wires).

Finally, the heat-stable emulsion developed for CSR has applications on its own. With >$10^9$ microcompartments/ml, emulsion PCR (ePCR) offers the possibility of parallel PCR multiplexing on a unprecedented scale with potential applications from gene linkage analysis to genomic repertoire construction directly from single cells. It may also have applications for large-scale diagnostic PCR applications like "Digital PCR" (Vogelstein and Kinzler, 1999, PNAS 96, 9236-9241). Compartmentalizing individual reactions can also even out competition among different gene segments that are amplified in either multiplex or random primed PCR and leads to a less biased distribution of amplification products. ePCR may thus provide an alternative to whole genome DOP-PCR (and related methodologies) or indeed be used to make DOP-PCR (and related methodologies) more effective.

The selection system according to our invention is based on self-replication in a compartmentalised system. Our invention relies on the fact that active replicases are able to replicate nucleic acids (in particular their coding sequences), while inactive replicases cannot. Thus, in the methods of our invention, we provide a compartmentalised system where a replicase in a compartment is substantially unable to act on any template other than the templates within that compartment; in particular, it cannot act to replicate a template within any other compartment. In highly preferred embodiments, the template nucleic acid within the compartment encodes the replicase. Thus, the replicase cannot replicate anything other than its coding sequence; the replicase is therefore "linked" to its coding sequence. As a result, in highly preferred embodiments of our invention, the final concentration of the coding sequence (i.e. copy number) is dependent on the activity of the enzyme encoded by it.

Our selection system as applied to selection of replicases has the advantage in that it links catalytic turnover ($k_{cat}/K_m$) to the post-selection copy-number of the gene encoding the catalyst. Thus, compartmentalisation offers the possibility of linking genotype and phenotype of a replicase enzyme, as described in further detail below, by a coupled enzymatic reaction involving the replication of the gene or genes of the enzyme(s) as one of its steps.

The methods of our invention preferably make use of nucleic acid libraries, the nature and construction of which will be explained in greater detail below. The nucleic acid library comprises a pool of different nucleic acids, members of that encode variants of a particular entity (the entity to be selected). Thus, for example, as used to select for replicases, the methods of our invention employ a nucleic acid library or pool having members, which encode the replicase or variants of the replicase. Each of the entities encoded by the various members of the library will have different properties, e.g., varying tolerance to heat or to the presence of inhibitory small molecules, or tolerance for base pair mismatches (as explained in further detail below). The population of nucleic acid variants therefore provides a starting material for selection, and is in many ways analogous to variation in a natural population of organisms caused by mutation.

According to our invention, the different members of the nucleic acid library or pool are sorted or compartmentalised into many compartments or microcapsules. In preferred embodiments, each compartment contains substantially one nucleic acid member of the pool (in one or several copies). In addition, the compartment also comprises the polypeptide or polynucleotide (in one or preferably several copies) encoded by that nucleic acid member (whether it is a replicase, an agent, a polypeptide, etc. as discussed below). The nature of these compartments is such that minimal or substantially no interchange of macromolecules (such as nucleic acids and polypeptides) occurs between different compartments. As explained in further detail below, highly preferred embodiments of our invention make use of aqueous compartments within water-in-oil emulsions. As explained above, any replicase activity present in the compartment (whether exhibited by the replicase, modified by an agent, or exhibited by the polypeptide acting in conjunction with another polypeptide) can only act on the template within the compartment.

The conditions within the compartments may be varied in order to select for polypeptides active under these conditions. For example, where replicases are selected, the compartments may have an increased temperature to select for replicases with higher thermal stability. Furthermore, using the selection methods described here on fusion proteins comprising thermostable replicase and a protein of interest will allow the selection of thermally stable proteins.

A method for the incorporation of thermal stability into otherwise labile proteins of commercial importance is desirable with regards to their large-scale production and distribution. A reporter system has been described to improve protein folding by expressing proteins as fusions with green fluorescent protein (GFP) (Waldo et al., 1999, *Nat. Biotechnol.* 17, 691-695). The function of the latter is related to the productive folding of the fused protein influencing folding and/or functionality of the GFP, enabling the directed evolution of variants with improved folding and expression. According to this aspect of our invention, proteins are fused to a thermostable replicase (or an agent promoting replicase activity) and selecting for active fusions in emulsion as a method for evolving proteins with increased thermostability and/or solubility. Unstable variants of the fusion partner are expected to aggregate and precipitate prior to or during thermal cycling, thus compromising replicase activity within respective compartments. Viable fusions will allow for self-amplification in emulsion, with the turnover rate being linked to the stability of the fusion partner.

In a related approach, novel or increased chaperonin activity may be evolved by coexpression of a library of chaperones together with a polymerase-polypeptide fusion protein, in which the protein moiety misfolds (under the selection conditions). Replication of the gene(s) encoding the chaperonin can only proceed after chaperonin activity has rescued polymerase activity in the polymerase-polypeptide fusion protein.

Thermostability of an enzyme may be measured by conventional means as known in the art. For example, the catalytic activity of the native enzyme may be assayed at a certain temperature as a benchmark. Enzyme assays are well known in the art, and standard assays have been established over the years. For example, incorporation of nucleotides by a polymerase is measured, by for example, use of radiolabeled dNTPs such as dATP and filter binding assays as known in the art. The enzyme whose thermostability is to be assayed is preincubated at an elevated temperature and then its activity retained (for example, polymerase activity in the case of polymerases) is measured at a lower, optimum temperature and compared to the benchmark. In the case of Taq polymerase, the elevated temperature is 97.5° C.; the optimum temperature is 72° C. Thermostability may be expressed in the form of half-life at the elevated temperature (i.e. time of incubation at higher temperature over which polymerase loses 50% of its activity). For example, the thermostable replicases, fusion proteins or agents selected by our invention may have a half-life that is 2×, 3×, 4×, 5×, 6×, 7×, 8×, 9×, 10× or more than the native enzyme. Most preferably, the thermostable replicases etc. have a half-life that is 11× or more when compared this way. Preferably, selected polymerases are preincubated at 95° C. or more, 97.5° C. or more, 100° C. or more, 105° C. or more, or 110° C. or more. Thus, in a highly preferred embodiment of our invention, we provide polymerases with increased thermostability which display a half life at 97.5° C. that is 11× or more than the corresponding wild-type (native) enzyme.

Resistance to an inhibitory agent, such as heparin in the case of polymerases, may also be assayed and measured as above. Resistance to inhibition may be expressed in terms of the concentration of the inhibitory factor. For example, in preferred embodiments of the invention, we provide heparin resistant polymerases that are active in up to a concentration of heparin between 0.083 units/μl to 0.33 units/μl. For comparison, our assays indicate that the concentration of heparin which inhibits native (wild-type) Taq polymerase is in the region of between 0.0005 to 0.0026 units/μl.

Resistance is conveniently expressed in terms of the inhibitor concentration, which is found to inhibit the activity of the selected replicase, fusion protein or agent, compared to the concentration, which is found to inhibit the native enzyme. Thus, the resistant replicases, fusion proteins, or agents selected by our invention may have 10×, 20×, 30×, 40×, 50×, 60×, 70×, 80×, 90×, 100×, 110×, 120×, 130×, 140×, 150×, 160×, 170×, 180×, 190×, 200×, or more resistance compared to the native enzyme. Most preferably, the resistant replicases etc. have 130× or more fold increased resistance when compared this way. The selected replicases etc. preferably have 50% or more, 60% or more, 70% or more, 80% or more, 90% or more, or even 100% activity at the concentration of the inhibitory factor. Furthermore, the compartments may contain amounts of an inhibitory agent such as heparin to select for replicases having activity under such conditions.

As explained below, the methods of our invention may be used to select for a pair of interacting polypeptides, and the conditions within the compartments may be altered to choose polypeptides capable of acting under these conditions (for example, high salt, or elevated temperature, etc.). The methods of our invention may also be used to select for the folding, stability and/or solubility of a fused polypeptide acting under these conditions (for example, high salt, or elevated temperature, chaotropic agents etc.).

The method of selection of our present invention may be used to select for various replicative activities, for example, for polymerase activity. Here, the replicase is a polymerase, and the catalytic reaction is the replication by the polymerase of its own gene. Thus, defective polymerases or polymerases which are inactive under the conditions under which the reaction is carried out (the selection conditions) are unable to amplify their own genes. Similarly, polymerases which are less active will replicate their coding sequences within their compartments more slowly. Accordingly, these genes will be under-represented, or even disappear from the gene pool.

Active polymerases, on the other hand, are able to replicate their own genes, and the resulting copy number of these genes will be increased. In a preferred embodiment of the invention, the copy number of a gene within the pool will be bear a direct relation to the activity of the encoded polypeptide under the conditions under which the reaction is carried out. In this preferred embodiment, the most active polymerase will be most represented in the final pool (i.e., its copy number within the pool will be highest). As will be appreciated, this enables easy cloning of active polymerases over inactive ones. The method of our invention therefore is able to directly link the turnover rate of the enzyme to the resulting copy-number of the gene encoding it.

As an example, the method may be applied to the isolation of active polymerases (DNA-, RNA-polymerases and reverse transcriptases) from thermophilic organisms. Briefly, a thermostable polymerase is expressed intracellularily in bacterial cells and these are compartmentalised (e.g. in a water-oil emulsion) in appropriate buffer together with appropriate amounts of the four dNTPs and oligonucleotides priming at either end of the polymerase gene or on plasmid sequences flanking the polymerase gene. The polymerase and its gene are released from the cells by a temperature step that lyses the cells and destroys enzymatic activities associated with the host cell. Polymerases from mesophilic organisms (or less thermostable polymerases) may be expressed in an analogous way except cell lysis should either proceed at ambient temperature (e.g. by expression of a lytic protein (e.g. derived from lytic bacteriophages, by detergent mediated lysis (e.g. Bugbuster™, commercially available) or lysis may proceed at elevated temperature in the presence of a polymerase stabilizing agent (e.g. high concentrations of proline (see example 27) in the case of Klenow or trehalose in the case of RT). In such cases background polymerase activity of the host strain may interfere with selections and it may be preferable to make use of mutant strains (e.g. polA⁻).

Alternatively, polymerase genes (either as plasmids or linear fragments) may be compartmentalised as above and the polymerase expressed in situ within the compartments using in vitro transcription translation (ivt), followed by a temperature step to destroy enzymatic activities associated with the in vitro translation extract. Polymerases from mesophilic organisms (or less thermostable polymerases) may be expressed in situ in an analogous way except in order to avoid enzymatic activities associated with the in vitro translation extract it may be preferable to use a translation extract reconstituted from defined purified components like the PURE system (Shimizu et al., 2001, *Nat. Biotech.* 19, 751).

Figure 1B:
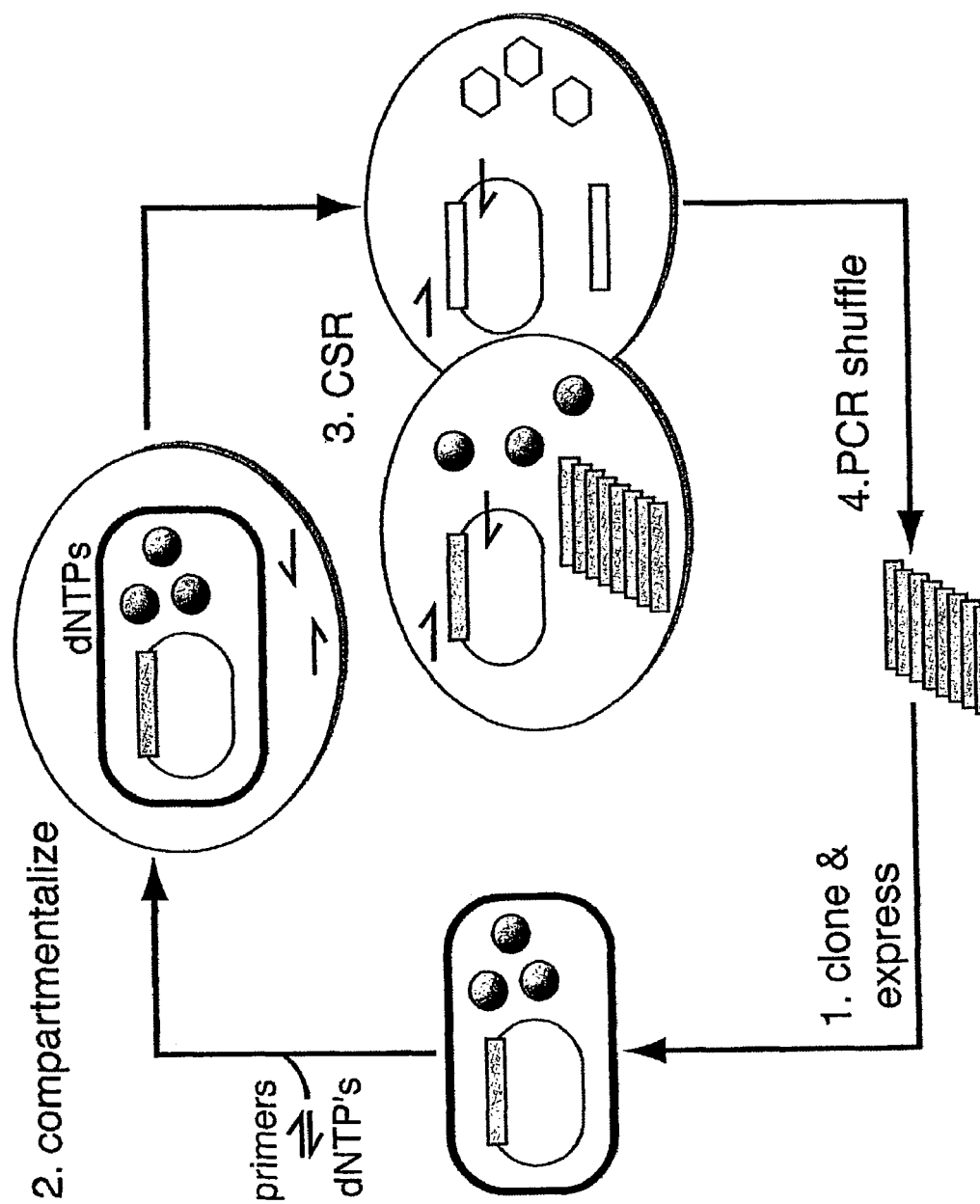
FIG. 1B is a diagram showing a general scheme of compartmentalised self-replication (CSR): 1) A repertoire of diversified polymerase genes is cloned and expressed in E. coli. Spheres represent active polymerase molecules. 2) Bacterial cells containing the polymerase and encoding gene are suspended in reaction buffer containing flanking primers and nucleotide triphosphates (dNTPs) and segregated into aqueous compartments. 3) The polymerase enzyme and encoding gene are released from the cell allowing self-replication to proceed. Poorly active polymerases (white hexagon) fail to replicate their encoding gene. 4) The "offspring" polymerase genes are released, rediversified and recloned for another cycle of CSR.

PCR thermocycling then leads to the amplification of the polymerase genes by the polypeptides they encode, i.e. only genes encoding active polymerases, or polymerases active under the chosen conditions will be amplified. Furthermore, the copy number of a polymerase gene X after self-amplification will be directly proportional to the catalytic activity of the polymerase X it encodes. (see FIGS. 1A and 1B).

Figure 3:
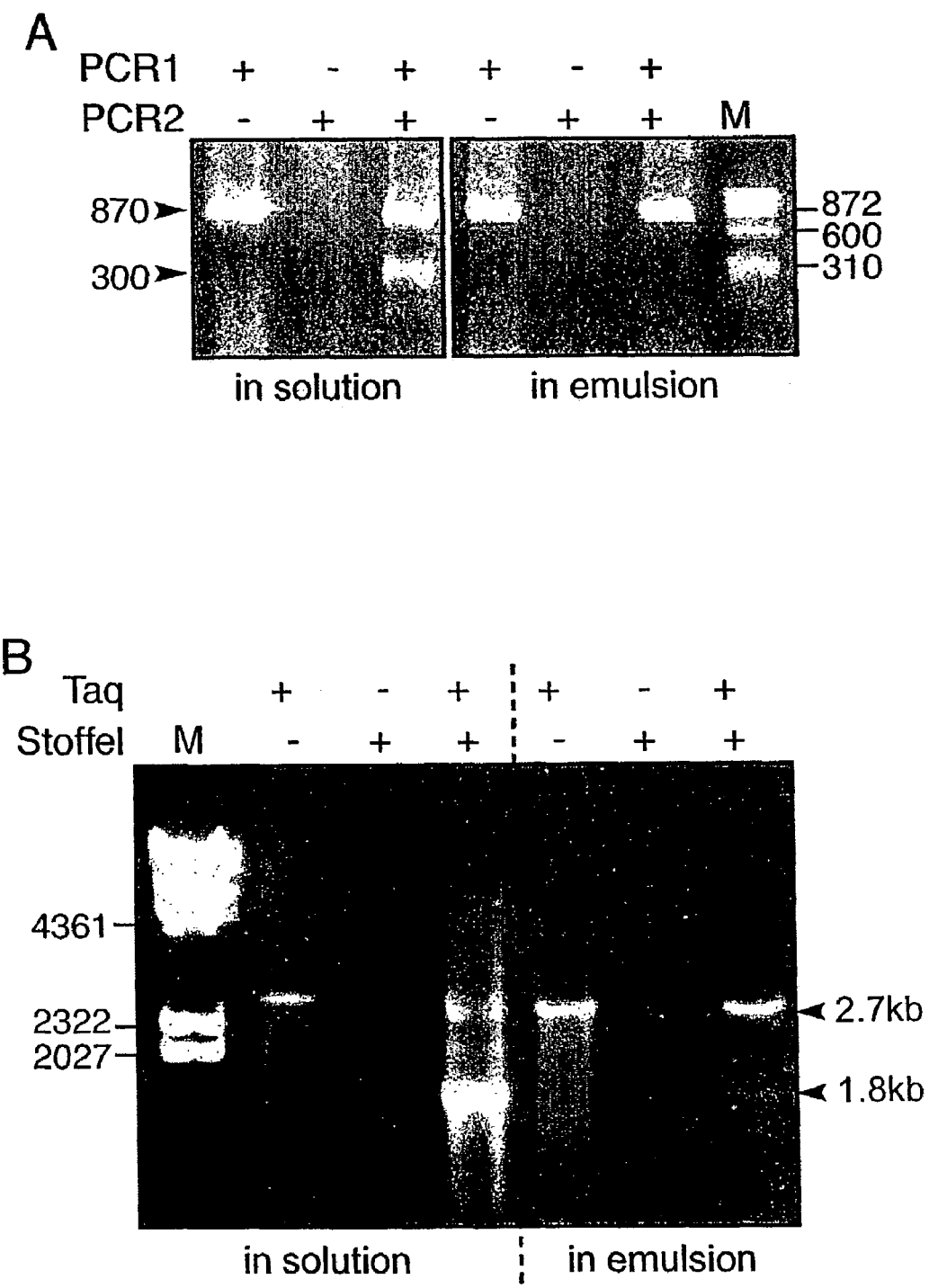
FIG. 3A is a diagram showing crossover between emulsion compartments. Two standard PCR reactions, differing in template size (PCR1 (0.9 kb), PCR2 (0.3 kb)) and presence of Taq (PCR1: +Taq, PCR 2: no enzyme), are amplified individually or combined. When combined in solution, both templates are amplified. When emulsified separately, prior to mixing, only PCR1 is amplified. M: φX174 HaeIII marker.
FIG. 3B is a diagram showing crossover between emulsion compartments. Bacterial cells expressing wild-type Taq polymerase (2.7 kb) or the Taq polymerase Stoffel fragment (poorly active under the buffer conditions) (1.8 kb) are mixed 1:1 prior to emulsification. In solution, the shorter Stoffel fragment is amplified preferentially. In emulsion, there is predominantly amplification of the wt Taq gene and only weak amplification of the Stoffel fragment (arrow). M: λHindIII marker.
Figure 4:
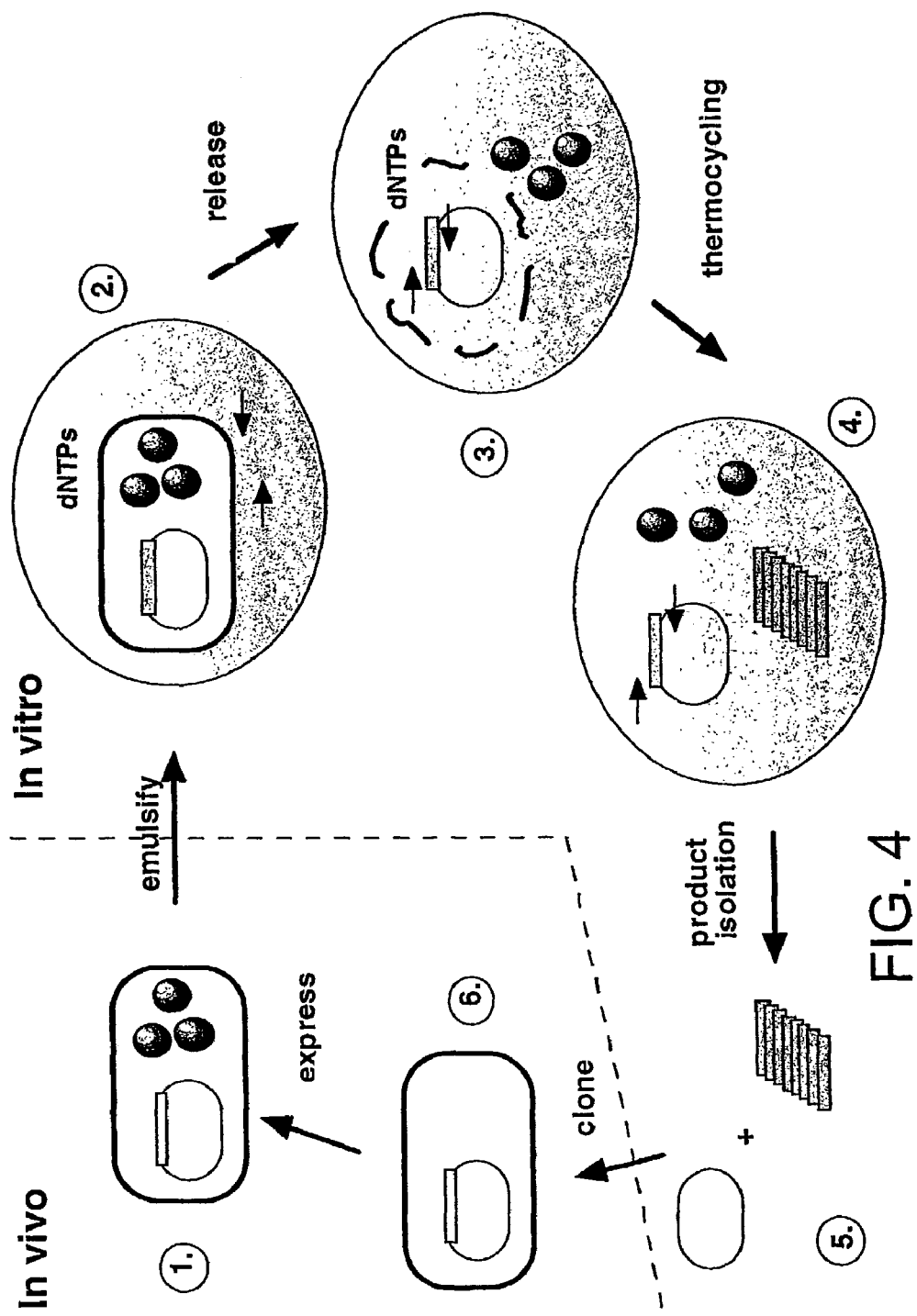
FIG. 4 is a diagram showing details of an embodiment of a method according to the present invention as applied to selection of a self-evolving polymerase.
Figure 5:
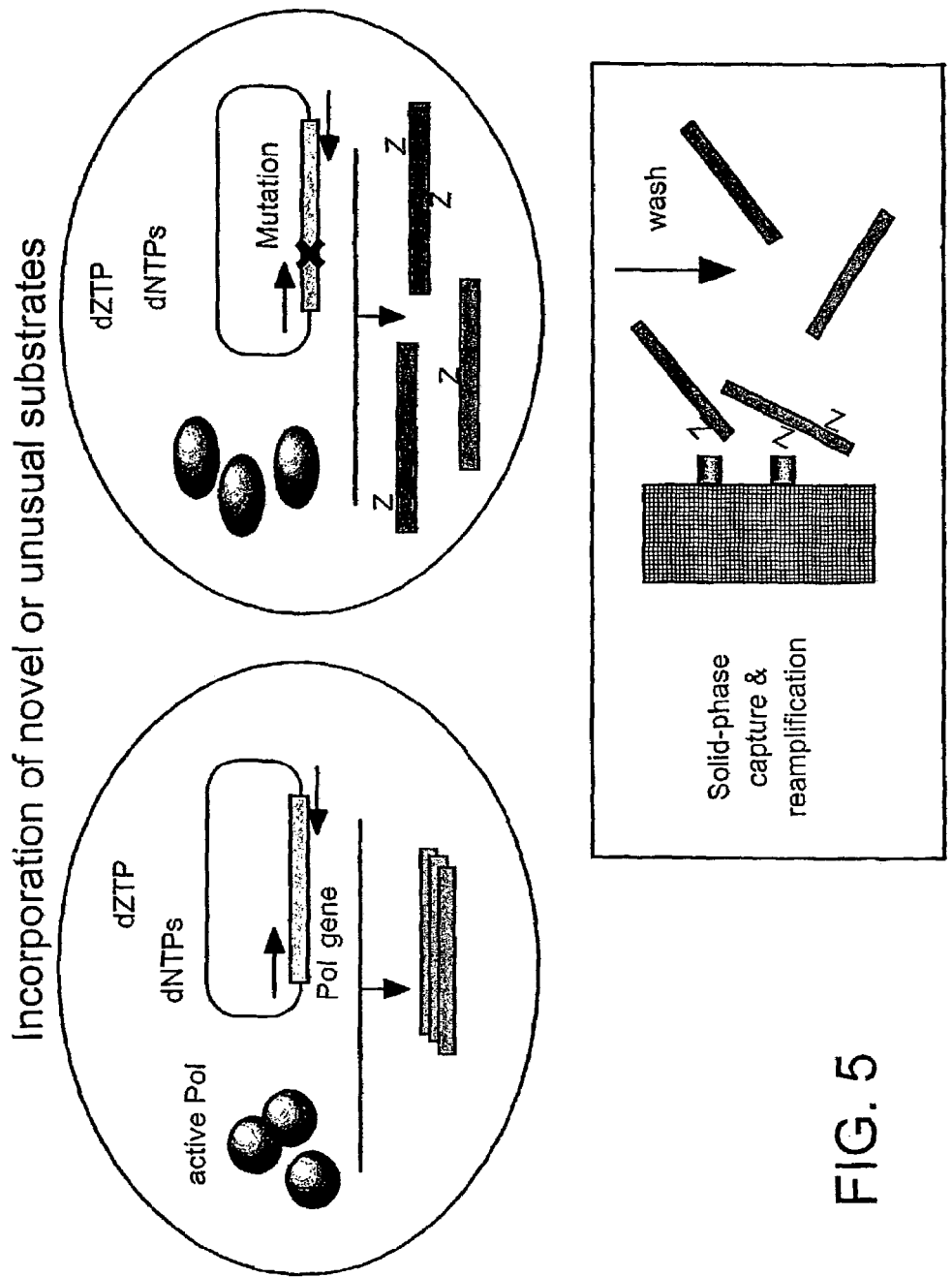
FIG. 5 is a diagram showing details of an embodiment of a method according to the present invention to select for incorporation of novel or unusual substrates.

By varying the selection conditions within the compartment, polymerases or other replicases with desired properties may be selected using the methods of our invention. Thus, by exposing repertoires of polymerase genes (diversified through targeted or random mutation) to self-amplification and by altering the conditions under which self-amplification can occur, the system can be used for the isolation and engineering of polymerases with altered, enhanced or novel properties. Such enhanced properties may include increased thermostability, increased processivity, increased accuracy (better proofreading), increased incorporation of unfavorable substrates (e.g., ribonucleotides, dye-modified, general bases such as 5-nitroindole, or other unusual substrates such as pyrene nucleotides (Matray and Kool, 1999, *Nature* 399, 704-708) (FIG. 3) or resistance to inhibitors (e.g. Heparin in clinical samples). Novel properties may be the incorporation of unnatural substrates (e.g. ribonucleotides), bypass reading of damaged sites (e.g. abasic sites (Paz-Elizur T. et al., 1997, *Biochemistry* 36, 1766), thymidine-dimers (Wood R. D., 1999, *Nature* 399, 639), hydantoin-bases (Duarte V. et al., 199, *Nucleic Acids Res.* 27, 496) and possibly even novel chemistries (e.g. novel backbones such as PNA (Nielsen P. E., 1999, *Curr. Opin. Biotechnol.* 10(1), 71-5) or sulfone (Benner S. A. et al., 1998 Feb., *Pure Appl. Chem.* 70(2), 263-6) or altered sugar chemistries (A. Eschenmoser, 1999, *Science* 284, 2118-24)). It may also be used to isolate or evolve factors that enhance or modify polymerase function such as processivity factors (like thioredoxin in the case of T7 DNA polymerase (Doublie S. et al., 1998, *Nature* 391, 251).

However, other enzymes besides replicases, such as telomerases, helicases etc. may also be selected according to our invention. Thus, telomerase is expressed in situ (in compartments) by for example in vitro translation together with Telomerase-RNA (either added or transcribed in situ as well; e.g. Bachand et al., 2000, *RNA* 6, 778-784).

Compartments also contain Taq Pol and dNTPs and telomere specific primers. At low temperature Taq is inactive but active telomerase will append telomeres to its own encoding gene (a linear DNA fragment with appropriate ends). After the telomerase reaction, thermocycling only amplifies active telomerase encoding genes. Diversity can be introduced in telomerase gene or RNA (or both) and could be targeted or random. As applied to selection of helicases, the selection method is essentially the same as described for telomerases, but helicase is used to unwind strands rather than heat denaturation.

The methods of our invention may also be used to select for DNA repair enzymes or translesion polymerases such as *E. coli* Pol IV and Pol V. Here, damage is introduced into primers (targeted chemistry) or randomly by mutagen treatment (e.g. UV, mutagenic chemicals etc.). This allows for selection for enzymes able to repair primers required for replication or own gene sequence (information retrieval) or, resulting in improved "repairases" for gene therapy etc.

The methods of our invention may also be used in its various embodiments for selecting agents capable of directly or indirectly modulating replicase activity. In addition, the invention may be used to select for a pair of polypeptides capable of interacting, or for selection of catalytic nucleic acids such as catalytic RNA (ribozymes). These and other embodiments will be explained in further detail below.

Nucleic Acid Processing Enzymes

As referred to herein, a nucleic acid processing enzyme is any enzyme, which may be a protein enzyme or a nucleic acid enzyme, which is capable of modifying, extending (such as by at least one nucleotide), amplifying or otherwise influencing nucleic acids such as to render the nucleic acid selectable by amplification in accordance with the present invention. Such enzymes therefore possess an activity which results in, for example, amplification, stabilisation, destabilisation, hybridisation or denaturation, replication, protection or deprotection of nucleic acids, or any other activity on the basis of which a nucleic acid can be selected by amplification. Examples include helicases, telomerases, ligases, recombinases, integrases and replicases. Replicases are preferred.

Replicase/Replication

As used here, the term "replication" refers to the template-dependent copying of a nucleic acid sequence. Nucleic acids are discussed and exemplified below. In general, the product of the replication is another nucleic acid, whether of the same species, or of a different species. Thus, included are the replication of DNA to produce DNA, replication of DNA to produce RNA, replication of RNA to produce DNA and replication of RNA to produce RNA. "Replication" is therefore intended to encompass processes such as DNA replication, polymerisation, ligation of oligonucleotides or polynucleotides (e.g. tri-nucleotide (triplet) 5'triphosphates) to form longer sequences, transcription, reverse transcription, etc.

The term "replicase" is intended to mean an enzyme having catalytic activity, which is capable of joining nucleotide, building blocks together to form nucleic acid sequences. Such nucleotide building blocks include, but are not limited to, nucleosides, nucleoside triphosphates, deoxynucleosides, deoxynucleoside triphosphates, nucleotides (comprising a nitrogen-containing base such as adenine, guanine, cytosine, uracil, thymine, etc., a 5-carbon sugar and one or more phosphate groups), nucleotide triphosphates, deoxynucleotides such as deoxyadenosine, deoxythymidine, deoxycytidine, deoxyuridine, deoxyguanidine, deoxynucleotides triphosphates (dNTPs), and synthetic or artificial analogues of these. Building blocks also include oligomers or polymers of any of the above, for example, trinucleotides (triplets), oligonucleotides and polynucleotides.

Thus, a replicase may extend a pre-existing nucleic acid sequence (primer) by incorporating nucleotides or deoxynucleotides. Such an activity is known in the art as "polymerisation", and the enzymes, which carry this out, are known as "polymerases". An example of such a polymerase replicase is DNA polymerase, which is capable of replicating DNA. The primer may be the same chemically, or different from, the extended sequence (for example, mammalian DNA polymerase is known to extend a DNA sequence from an RNA primer). The term replicase also includes those enzymes which join together nucleic acid sequences, whether polymers or oligomers to form longer nucleic acid sequences. Such an activity is exhibited by the ligases, which ligate pieces of DNA or RNA.

The replicase may consist entirely of replicase sequence, or it may comprise a replicase sequence linked to a heterologous polypeptide or other molecule such as an agent by chemical means or in the form of a fusion protein or be assembled from two or more constituent parts.

Preferably, the replicase according to the invention is a DNA polymerase, RNA polymerase, reverse transcriptase, DNA ligase, or RNA ligase.

Preferably, the replicase is a thermostable replicase. A "thermostable" replicase as used here is a replicase, which demonstrates significant resistance to thermal denaturation at elevated temperatures, typically above body temperature (37° C.). Preferably, such a temperature is in the range 42° C. to 160° C., more preferably, between 60 to 100° C., most preferably, above 90° C. Compared to a non-thermostable replicase, the thermostable replicase displays a significantly increased half-life (time of incubation at elevated temperature that results in 50% loss of activity). Preferably, the thermostable replicase retains 30% or more of its activity after incubation at the elevated temperature, more preferably, 40%, 50%, 60%, 70% or 80% or more of its activity. Yet more preferably, the replicase retains 80% activity. Most preferably, the activity retained is 90%, 95% or more, even 100%. Non-thermostable replicases would exhibit little or no retention of activity after similar incubations at the elevated temperature.

Polymerase

An example of a replicase is DNA polymerase. DNA polymerase enzymes are naturally occurring intracellular enzymes, and are used by a cell to replicate a nucleic acid strand using a template molecule to manufacture a complementary nucleic acid strand. Enzymes having DNA polymerase activity catalyze the formation of a bond between the 3' hydroxyl group at the growing end of a nucleic acid primer and the 5' phosphate group of a nucleotide triphosphate. These nucleotide triphosphates are usually selected from deoxyadenosine triphosphate (A), deoxythymidine triphosphate (T), deoxycytidine triphosphate (C) and deoxyguanosine triphosphate (G). However, DNA polymerases may incorporate modified or altered versions of these nucleotides. The order in which the nucleotides are added is dictated by base pairing to a DNA template strand; such base pairing is accomplished through "canonical" hydrogen-bonding (hydrogen-bonding between A and T nucleotides and G and C nucleotides of opposing DNA strands), although non-canonical base pairing, such as G:U base pairing, is known in the art. See e.g., Adams et al., The Biochemistry of the Nucleic Acids 14-32 (11th ed. 1992). The in-vitro use of enzymes having DNA polymerase activity has in recent years become more common in a variety of biochemical applications including cDNA synthesis and DNA sequencing reactions (see Sambrook et al., (2nd ed. Cold Spring Harbor Laboratory Press, 1989) hereby incorporated by reference herein), and amplification of nucleic acids by methods such as the polymerase chain reaction (PCR) (Mullis et al., U.S. Pat. Nos. 4,683,195, 4,683,202, and 4,800,159, hereby incorporated by reference herein) and RNA transcription-mediated amplification methods (e.a., Kacian et al., PCT Publication No. WO91/01384).

Methods such as PCR make use of cycles of primer extension through the use of a DNA polymerase activity, followed by thermal denaturation of the resulting double-stranded nucleic acid in order to provide a new template for another round of primer annealing and extension. Because the high temperatures necessary for strand denaturation result in the irreversible inactivations of many DNA polymerases, the discovery and use of DNA polymerases able to remain active at temperatures above about 37° C. to 42° C. (thermostable DNA polymerase enzymes) provides an advantage in cost and labor efficiency. Thermostable DNA polymerases have been discovered in a number of thermophilic organisms including, but not limited to *Thermus aquaticus, Thermus thermophilus*, and species of the *Bacillus, Thermococcus, Sulfolobus, Pyrococcus* genera. DNA polymerases can be purified directly from these thermophilic organisms. However, substantial increases in the yield of DNA polymerase can be obtained by first cloning the gene encoding the enzyme in a multicopy expression vector by recombinant DNA technology methods, inserting the vector into a host cell strain capable of expressing the enzyme, culturing the vector-containing host cells, then extracting the DNA polymerase from a host cell strain which has expressed the enzyme.

The bacterial DNA polymerases that have been characterized to date have certain patterns of similarities and differences which has led some to divide these enzymes into two groups: those whose genes contain introns/inteins (Class B DNA polymerases), and those whose DNA polymerase genes are roughly similar to that of *E. coli* DNA polymerase I and do not contain introns (Class A DNA polymerases).

Several Class A and Class B thermostable DNA polymerases derived from thermophilic organisms have been cloned and expressed. Among the class A enzymes: Lawyer et al., 1989, *J. Biol. Chem.* 264, 6427-6437, and Gelfund et al., U.S. Pat. No. 5,079,352, report the cloning and expression of a full length thermostable DNA polymerase derived from *Thermus aquaticus* (Taq). Lawyer et al., 1993, *PCR Methods and Applications* 2, 275-287, and Barnes, PCT Publication No. WO92/06188 (1992), disclose the cloning and expression of truncated versions of the same DNA polymerase, while Sullivan, EPO Publication No. 0482714A1 (1992), reports cloning a mutated version of the Taq DNA polymerase. Asakura et al., 1993, *J. Ferment. Bioeng.* (Japan) 74, 265-269, have reportedly cloned and expressed a DNA polymerase from *Thermus thermophilus*. Gelfund et al., PCT Publication No. WO92/06202 (1992), have disclosed a purified thermostable DNA polymerase from *Thermosipho africanus*. A thermostable DNA polymerase from *Thermus flavus* is reported by Akhmetzjanov and Vakhitov, 1992, *Nucleic Acids Res.* 20, 5839. Uemori et al., 1993, *J. Biochem.* 113, 401-410 and EPO Publication No. 0517418A2 (1992) have reported cloning and expressing a DNA polymerase from the thermophilic bacterium *Bacillus caldotenax*. Ishino et al., Japanese Patent Application No. HEI 4[1992]-1 31400 (publication date Nov. 19, 1993) report cloning a DNA polymerase from *Bacillus stearothermophilus*. Among the Class B enzymes: A recombinant thermostable DNA polymerase from *Thermococcus litoralis* is reported by Comb et al., EPO Publication No. 0 455 430 A3 (1991), Comb et al., EPO Publication No. 0547920A2 (1993), and Perler et al., 1992, *Proc. Natl. Acad. Sci. USA* 89, 5577-5581. A cloned thermostable DNA polymerase from *Sulfolobus solofatarius* is disclosed in Pisani et al., 1992, *Nucleic Acids Res.* 20, 2711-2716 and in PCT Publication WO93/25691 (1993). The thermostable enzyme of *Pyrococcus furiosus* is disclosed in Uemori et al., 1993, *Nucleic Acids Res.* 21, 259-265, while a recombinant DNA polymerase is derived from Pyrococcus sp. as disclosed in Comb et al., EPO Publication No. 0547359A1 (1993).

Many thermostable DNA polymerases possess activities additional to a DNA polymerase activity; these may include a 5'-3' exonuclease activity and/or a 3'-5' exonuclease activity. The activities of 5'-3' and 3'-5' exonucleases are well known to those of ordinary skill in the art. The 3'-5' exonuclease activity improves the accuracy of the newly-synthesized strand by removing incorrect bases that may have been incorporated; DNA polymerases in which such activity is low or absent, reportedly including Taq DNA polymerase (see Lawyer et al., *J. Biol. Chem.* 264, 6427-6437), have elevated error rates in the incorporation of nucleotide residues into the primer extension strand. In applications such as nucleic acid amplification procedures in which the replication of DNA is often geometric in relation to the number of primer extension cycles, such errors can lead to serious artifactual problems such as sequence heterogeneity of the nucleic acid amplification product (amplicon). Thus, a 3'-5' exonuclease activity is a desired characteristic of a thermostable DNA polymerase used for such purposes.

By contrast, the 5'-3' exonuclease activity often present in DNA polymerase enzymes is often undesired in a particular application since it may digest nucleic acids, including primers, that have an unprotected 5' end. Thus, a thermostable DNA polymerase with an attenuated 5'-3' exonuclease activity, or in which such activity is absent, is also a desired characteristic of an enzyme for biochemical applications.

Various DNA polymerase enzymes have been described where a modification has been introduced in a DNA polymerase, which accomplishes this object. For example, the Klenow fragment of *E. coli* DNA polymerase I can be produced as a proteolytic fragment of the holoenzyme in which the domain of the protein controlling the 5'-3' exonuclease activity has been removed. The Klenow fragment still retains the polymerase activity and the 3'-5' exonuclease activity. Barnes, supra, and Gelfund et al., U.S. Pat. No. 5,079,352 have produced 5'-3' exonuclease-deficient recombinant Taq DNA polymerases. Ishino et al., EPO Publication No. 0517418A2, have produced a 5'-3' exonuclease-deficient DNA polymerase derived from *Bacillus caldotenax*. On the other hand, polymerases lacking the 5'-3' exonuclease domain often have reduced processivity.

Ligase

DNA strand breaks and gaps are generated transiently during replication, repair and recombination. In mammalian cell nuclei, rejoining of such strand breaks depends on several different DNA polymerases and DNA ligase enzymes. The mechanism for joining of DNA strand interruptions by DNA ligase enzymes has been widely described. The reaction is initiated by the formation of a covalent enzyme-adenylate complex. Mammalian and viral DNA ligase enzymes employ ATP as cofactor, whereas bacterial DNA ligase enzymes use NAD to generate the adenylyl group. In the case of ATP-utilising ligases, the ATP is cleaved to AMP and pyrophosphate with the adenylyl residue linked by a phosphoramidate bond to the $\epsilon$-amino group of a specific lysine residue at the active site of the protein (Gumport, R. I. et al., 1971, *PNAS* 68, 2559-63). Reactivated AMP residue of the DNA ligase-adenylate intermediate is transferred to the 5' phosphate terminus of a single strand break in double stranded DNA to generate a covalent DNA-AMP complex with a 5'-5' phosphoanhydride bond. his reaction intermediate has also been isolated for microbial and mammalian DNA ligase enzymes, but is shorter lived than the adenylylated enzyme. In the final step of DNA ligation, unadenylylated DNA ligase enzymes required for the generation of a phosphodiester bond catalyze displacement of the AMP residue through attack by the adjacent 3'-hydroxyl group on the adenylylated site.

The occurrence of three different DNA ligase enzymes, DNA Ligase I, II and III, is established previously by biochemical and immunological characterization of purified enzymes (Tonikinson, A. E. et al., 1991, *J. Biol. Chem.* 266, 21728-21735, and Roberts, E. et al., 1994, *J. Biol. Chem.* 269, 3789-3792).

Amplification

The methods of our invention involve the templated amplification of desired nucleic acids. "Amplification" refers to the increase in the number of copies of a particular nucleic acid fragment (or a portion of this) resulting either from an enzymatic chain reaction (such as a polymerase chain reaction, a ligase chain reaction, or a self-sustained sequence replication) or from the replication of all or part of the vector into which it has been cloned. Preferably, the amplification according to our invention is an exponential amplification, as exhibited by for example the polymerase chain reaction.

Many target and signal amplification methods have been described in the literature, for example, general reviews of these methods in Landegren, U. et al., 1988, *Science* 242, 229-237, and Lewis, R., 1990, *Genetic Engineering News* 10:1, 54-55. These amplification methods may be used in the methods of our invention, and include polymerase chain reaction (PCR), PCR in situ, ligase amplification reaction (LAR), ligase hybridization, Q bacteriophage replicase, transcription-based amplification system (TAS), genomic amplification with transcript sequencing (GAWTS), nucleic acid sequence-based amplification (NASBA) and in situ hybridization.

Polymerase Chain Reaction (PCR)

PCR is a nucleic acid amplification method described inter alia in U.S. Pat. Nos. 4,683,195 and 4,683,202. PCR consists of repeated cycles of DNA polymerase generated primer extension reactions. The target DNA is heat denatured and two oligonucleotides, which bracket the target sequence on opposite strands of the DNA to be amplified, are hybridized. These oligonucleotides become primers for use with DNA polymerase. The DNA is copied by primer extension to make a second copy of both strands. By repeating the cycle of heat denaturation, primer hybridization and extension, the target DNA can be amplified a million fold or more in about two to four hours. PCR is a molecular biology tool, which must be used in conjunction with a detection technique to determine the results of amplification. An advantage of PCR is that it increases sensitivity by amplifying the amount of target DNA by 1 million to 1 billion fold in approximately 4 hours.

The polymerase chain reaction may be used in the selection methods of our invention as follows. For example, PCR may be used to select for variants of Taq polymerase having polymerase activity. As described in further detail above, a library of nucleic acids each encoding a replicase or a variant of the replicase, for example, Taq polymerase, is generated and subdivided into compartments. Each compartment comprises substantially one member of the library together with the replicase or variant encoded by that member.

The polymerase or variant may be expressed in vivo within a transformed bacterium or any other suitable expression host, for example yeast or insect or mammalian cells, and the expression host encapsulated within a compartment. Heat or other suitable means is applied to disrupt the host and to release the polymerase variant and its encoding nucleic acid within the compartment. In the case of a bacterial host, timed expression of a lytic protein, for example protein E from ΦX174, or use of an inducible λ lysogen, may be employed for disrupting the bacterium.

It will be clear that the polymerase or other enzyme need not be a heterologous protein expressed in that host (e.g., a plasmid), but maybe expressed from a gene forming part of the host genome. Thus, the polymerase may be for example an endogenous or native bacterial polymerase. We have shown that in the case of nucleotide diphosphate kinase (ndk), endogenous (uninduced) expression of ndk is sufficient to generate dNTPs for its own replication. Thus, the methods of selection according to our invention may be employed for the direct functional cloning of polymerases and other enzymes from diverse (and uncultured) microbial populations.

Alternatively, the nucleic acid library may be compartmentalised together with components of an in vitro transcription/translation system (as described in further detail in this document), and the polymerase variant expressed in vitro within the compartment.

Each compartment also comprises components for a PCR reaction, for example, nucleotide triphosphates (dNTPs), buffer, magnesium, and oligonucleotide primers. The oligonucleotide primers may have sequences corresponding to sequences flanking the polymerase gene (i.e., within the genomic or vector DNA) or to sequences within the polymerase gene. PCR thermal cycling is then initiated to allow any polymerase variant having polymerase activity to amplify the nucleic acid sequence.

Active polymerases will amplify their corresponding nucleic acid sequences, while nucleic acid sequences encoding weakly active or inactive polymerases will be weakly replicated or not be replicated at all. In general, the final copy number of each member of the nucleic acid library will be expected to be proportional to the level of activity of the polymerase variant encoded by it. Nucleic acids encoding active polymerases will be over-represented, and nucleic acids encoding inactive or weakly active polymerases will be under-represented. The resulting amplified sequences may then be cloned and sequenced, etc., and replication ability of each member assayed.

As described in further detail elsewhere, the conditions within each compartment may be altered to select for polymerases active under these conditions. For example, heparin may be added to the reaction mix to choose polymerases, which are resistant to heparin. The temperature at which PCR takes place may be elevated to select for heat resistant variants of polymerase. Furthermore, polymerases may be selected which are capable of extending DNA sequences such as primers with altered 3' ends or altered parts of the primer sequence. The altered 3' ends or other alterations can include unnatural bases (altered sugar or base moieties), modified bases (e.g. blocked 3' ends) or even primers with altered backbone chemistries (e.g. PNA primers).

Reverse Transcriptase-PCR

RT-PCR is used to amplify RNA targets. In this process, the reverse transcriptase enzyme is used to convert RNA to complementary DNA (cDNA), which can then be amplified using PCR. This method has proven useful for the detection of RNA viruses.

The methods of our invention may employ RT-PCR. Thus, the pool of nucleic acids encoding the replicase or its variants may be provided in the form of an RNA library. This library could be generated in vivo in bacteria, mammalian cells, yeast etc., which are compartmentalised, or by in-vitro transcription of compartmentalised DNA. The RNA could encode a co-compartmentalised replicase (e.g. reverse transcriptase or polymerase) that has been expressed in vivo (and released in emulsion along with the RNA by means disclosed below) or in vitro. Other components necessary for amplification (polymerase and/or reverse transcriptase, dNTPs, primers) are also compartmentalised. Under given selection pressure(s), the cDNA product of the reverse transcription reaction serves as a template for PCR amplification. As with other replication reactions (in particular ndk in the Examples) the RNA may encode a range of enzymes feeding the reaction.

Self-Sustained Sequence Replication (3SR)

Self-sustained sequence replication (3SR) is a variation of TAS, which involves the isothermal amplification of a nucleic acid template via sequential rounds of reverse transcriptase (RT), polymerase and nuclease activities that are mediated by an enzyme cocktail and appropriate oligonucleotide primers (Guatelli et al., 1990, *Proc. Natl. Acad. Sci. USA* 87, 1874). Enzymatic degradation of the RNA of the RNA/DNA heteroduplex is used instead of heat denaturation. RNAse H and all other enzymes are added to the reaction and all steps occur at the same temperature and without further reagent additions. Following this process, amplifications of $10^6$ to $10^9$ have been achieved in one hour at 42° C.

The methods of our invention may therefore be extended to select polymerases or replicases from mesophilic organisms using 3SR isothermal amplification (Guatelli et al., 1990, *Proc. Natl. Acad. Sci. USA* 87, 7797; Compton, 1991, *Nature* 7:350, 91-92) instead of PCR thermocycling. As described above, 3SR involves the concerted action of two enzymes: an RNA polymerases as well as a reverse transcriptase cooperate in a coupled reaction of transcription and reverse transcription, leading to the simultaneous amplification of both RNA and DNA. Clearly, in this system self-amplification may be applied to either of the two enzymes involved or to both simultaneously. It may also include the evolution of the RNAse H activity either as part of the reverse transcriptase enzyme (e.g. HIV-1 RT) or on its own.

The various enzymatic activities that define 3SR and related methods are all targets for selection using the methods of our invention. Variants of either T7 RNA polymerase, reverse transcriptase (RT), or RNAse H can be provided within the aqueous compartments of the emulsions, and selected for under otherwise limiting conditions. These variants can be introduced via E. coli "gene pellets" (i.e., bacteria express the polypeptide), or other means as described elsewhere in this document. Initial release in emulsion may be mediated by enzymatic (for example, lambda lysogen) or thermal lysis, or other methods as disclosed here. The latter may necessitate the use of agents that stabilize enzymatic activity at transiently elevated temperatures. For example, it may be necessary to include amounts of proline, glycerol, trehalose or other stabilising agents as known in the art to effect stabilisation of thermosensitive enzymes such as reverse transcriptase. Furthermore, stepwise removal of the agent may be undertaken to select for increased stability of the thermosensitive enzyme.

Alternatively, and as disclosed elsewhere, variants may be produced via coupled transcription translation, with the expressed products feeding into the 3SR cycle.

It will also be appreciated that it is possible to replace reverse transcriptase with the thermostable Tth DNA polymerase. Tth DNA polymerase is known to have reverse transcriptase activity and the RNA template is effectively reverse-transcribed into template DNA using this enzyme. It is therefore possible to select for useful variants of this enzyme, by for example, introducing bacterially expressed T7 RNA polymerase variants into emulsion and preincubation at an otherwise non-permissive temperature.

Example 18 below is an example showing one way in which the methods of our invention may be applied to selection of replicases using self-sustained sequence replication (3SR).

Ligation Amplification (LAR/LAS)

Ligation amplification reaction or ligation amplification system uses DNA ligase and four oligonucleotides, two per target strand. This technique is described by Wu, D. Y. and Wallace, R. B., 1989, *Genomics* 4, 560. The oligonucleotides hybridize to adjacent sequences on the target DNA and are joined by the ligase. The reaction is heat denatured and the cycle repeated.

By analogy to the application to polymerases, our method may be applied to ligases in particular from thermophilic organisms. Oligonucleotides complementary to one strand of the ligase gene sequence are synthesized (either as perfect match or comprising targeted or random diversity). The two end oligos overlap into the vector or untranslated regions of the ligase gene. The ligase gene is either cloned for expression in an appropriate host and compartmentalized together with the oligonucleotides and an appropriate energy source (usually ATP (or NADPH)). If necessary, the ligase expressed as above in bacteria is released from the cells by thermal lysis. Compartments contain appropriate buffer together with appropriate amounts of an appropriate energy source (ATP or NADH) and oligonucleotides encoding the whole of the ligase gene as well as flanking sequences required for cloning. Ligation of oligonucleotides leads to assembly of a full-length ligase gene (templated by the ligase gene on the expression plasmid) by an active ligase. In compartments containing an inactive ligase, no assembly will take place. As with polymerases, the copy number of a ligase gene X after self-ligation will preferably be proportional to the catalytic activity under the selection conditions of the ligase X it encodes.

After lysis of the cell, thermocycling leads to annealing of the oligonucleotides to the ligase gene. However, ligation of the oligos and thus assembly of the full-length ligase gene depends on the presence of an active ligase in the same compartment. Thus only genes encoding active ligases will assemble their own encoding genes from the present oligonucleotides. Assembled genes can then be amplified, diversified and recloned for another round of selection if necessary. The methods of our invention are therefore suitable for the selection of ligases, which are faster or more efficient at ligation.

As noted elsewhere, the ligase can be produced either in situ by expression from a suitable bacterial or other host, or by in vitro translation. The ligase may be an oligonucleotide (e.g. ribo or deoxiribozyme) ligase assembling its own sequence from available fragments, or the ligase may be a conventional (polypeptide) ligase. The length of the oligonucleotides will depend on the particular reaction, but if necessary, they can be very short (e.g. triplets). As noted elsewhere, the method of our invention may be used to select for an agent capable of modulating ligase activity, either directly or indirectly. For example, the gene to be evolved may be another enzyme or enzymes that generates a substrate for the ligase (e.g. NADH) or consumes an inhibitor. In this case the oligonucleotides encode parts of the other enzyme or enzymes etc.

The ligation reaction between oligonucleotides may incorporate alternative chemistries e.g. amide linkages. As long as the chemical linkages do not interfere with templated copying of the opposite strand by any replicase (e.g. reverse transcriptase), a wide variety of linkage chemistries and ligases that catalyse it may be evolved.

Qβ Replicase

In this technique, RNA replicase for the bacteriophage Qβ, which replicates single-stranded RNA, is used to amplify the target DNA, as described by Lizardi et al., 1988, *Bio. Technology* 6, 1197. First, the target DNA is hybridized to a primer including a T7 promoter and a Qβ 5' sequence region. Using this primer, reverse transcriptase generates a cDNA connecting the primer to its 5' end in the process. These two steps are similar to the TAS protocol. The resulting heteroduplex is heat denatured. Next, a second primer containing a Qβ 3' sequence region is used to initiate a second round of cDNA synthesis. This results in a double stranded DNA containing both 5' and 3' ends of the Qβ bacteriophage as well as an active T7 RNA polymerase binding site. T7 RNA polymerase then transcribes the double-stranded DNA into new RNA, which mimics the Qβ. After extensive washing to remove any unhybridized probe, the new RNA is eluted from the target and replicated by Qβ replicase. The latter reaction creates $10^7$ fold amplification in approximately 20 minutes. Significant background may be formed due to minute amounts of probe RNA that is non-specifically retained during the reaction.

A reaction employing Qβ replicase as described above may be used to build a continuous selection reaction in an alternative embodiment according to our invention.

For example, the gene for Qβ replicase (with appropriate 5' and 3' regions) is added to an in vitro translation reaction and compartmentalised. In compartments, the replicase is expressed and immediately starts to replicate its own gene. Only genes encoding an active replicase replicate themselves. Replication proceeds until NTPs are exhausted. However, as NTPs can be made to diffuse through the emulsion (see the description of ndk in the Examples), the replication reaction may be "fed" from the outside and proceed much longer, essentially until there is no room left within the compartments for further replication. It is possible to propagate the reaction further by serial dilution of the emulsion mix into a fresh oil-phase and re-emulsification after addition of a fresh water-phase containing NIPs. Qβ replicase is known to be very error-prone, so replication alone will introduce lots of random diversity (which may be desirable). The methods described here allow the evolution of more specific (e.g. primer dependent) forms of Qβ-replicase. As with other replication reactions (in particular ndk in the Examples) a range of enzymes feeding the reaction may be evolved.

Other Amplification Techniques

Alternative amplification technology may be exploited in the present invention. For example, rolling circle amplification (Lizardi et al., 1998, *Nat. Genet.* 19, 225) is an amplification technology available commercially (RCAT™) which is driven by DNA polymerase and can replicate circular oligonucleotide probes with either linear or geometric kinetics under isothermal conditions.

In the presence of two suitably designed primers, a geometric amplification occurs via DNA strand displacement and hyperbranching to generate $10^{12}$ or more copies of each circle in 1 hour.

If a single primer is used, RCAT generates in a few minutes a linear chain of thousands of tandemly linked DNA copies of a target covalently linked to that target.

A further technique, strand displacement amplification (SDA; Walker et al., 1992 PNAS (USA) 80, 392) begins with a specifically defined sequence unique to a specific target. But unlike other techniques which rely on thermal cycling, SDA is an isothermal process that utilizes a series of primers, DNA polymerase and a restriction enzyme to exponentially amplify the unique nucleic acid sequence.

SDA comprises both a target generation phase and an exponential amplification phase.

In target generation, double-stranded DNA is heat denatured creating two single-stranded copies. A series of specially manufactured primers combine with DNA polymerase (amplification primers for copying the base sequence and bumper primers for displacing the newly created strands) to form altered targets capable of exponential amplification.

The exponential amplification process begins with altered targets (single-stranded partial DNA strands with restricted enzyme recognition sites) from the target generation phase.

An amplification primer is bound to each strand at its complimentary DNA sequence. DNA polymerase then uses the primer to identify a location to extend the primer from its 3' end, using the altered target as a template for adding individual nucleotides. The extended primer thus forms a double-stranded DNA segment containing a complete restriction enzyme recognition site at each end.

A restriction enzyme is then bound to the double stranded DNA segment at its recognition site. The restriction enzyme dissociates from the recognition site after having cleaved only one strand of the double-sided segment, forming a nick. DNA polymerase recognizes the nick and extends the strand from the site, displacing the previously created strand. The recognition site is thus repeatedly nicked and restored by the restriction enzyme and DNA polymerase with continuous displacement of DNA strands containing the target segment.

Each displaced strand is then available to anneal with amplification primers as above. The process continues with repeated nicking, extension and displacement of new DNA strands, resulting in exponential amplification of the original DNA target.

Selection of Catalytic RNA

Known methods of in-vitro evolution have been used to generate catalytically active RNA molecules (ribozymes) with a diverse range of activities. However, these have involved selection by self-modification, which inherently isolates variants that rely on proximity catalysis and which display reduced activities in trans.

Compartmentalisation affords a means to select for truly trans-acting ribozymes capable of multiple turnover, without the need to tether substrate to the ribozyme by covalent linkage or hydrogen-bonding (i.e., base-pairing) interactions.

In its simplest case, a gene encoding a ribozyme can be introduced into emulsion and readily transcribed as demonstrated by the transcription and the 3SR amplification of the RNA encoding Taq polymerase in situ as follows: The Taq polymerase gene is first transcribed in emulsion. 100 µl of a reaction mix comprising 80 mM HEPES-KOH (pH 7.5), 24 mM $MgCl_2$, 2 mM spermidine, 40 mM DTT, rNTPs (30 mM), 50 ng T7-Taq template (see Example 18. Selection Using Self-Sustained Sequence Replication (3SR)), 60 units T7 RNA polymerase (USB), 40 units RNAsin (Promega) is emulsified using the standard protocol. Emulsions are incubated at 37° C. for up to 6 hours and analysis of reaction products by gel electrophoresis showed levels of RNA production to be comparable to those of the non-emulsified control.

Figure 6:
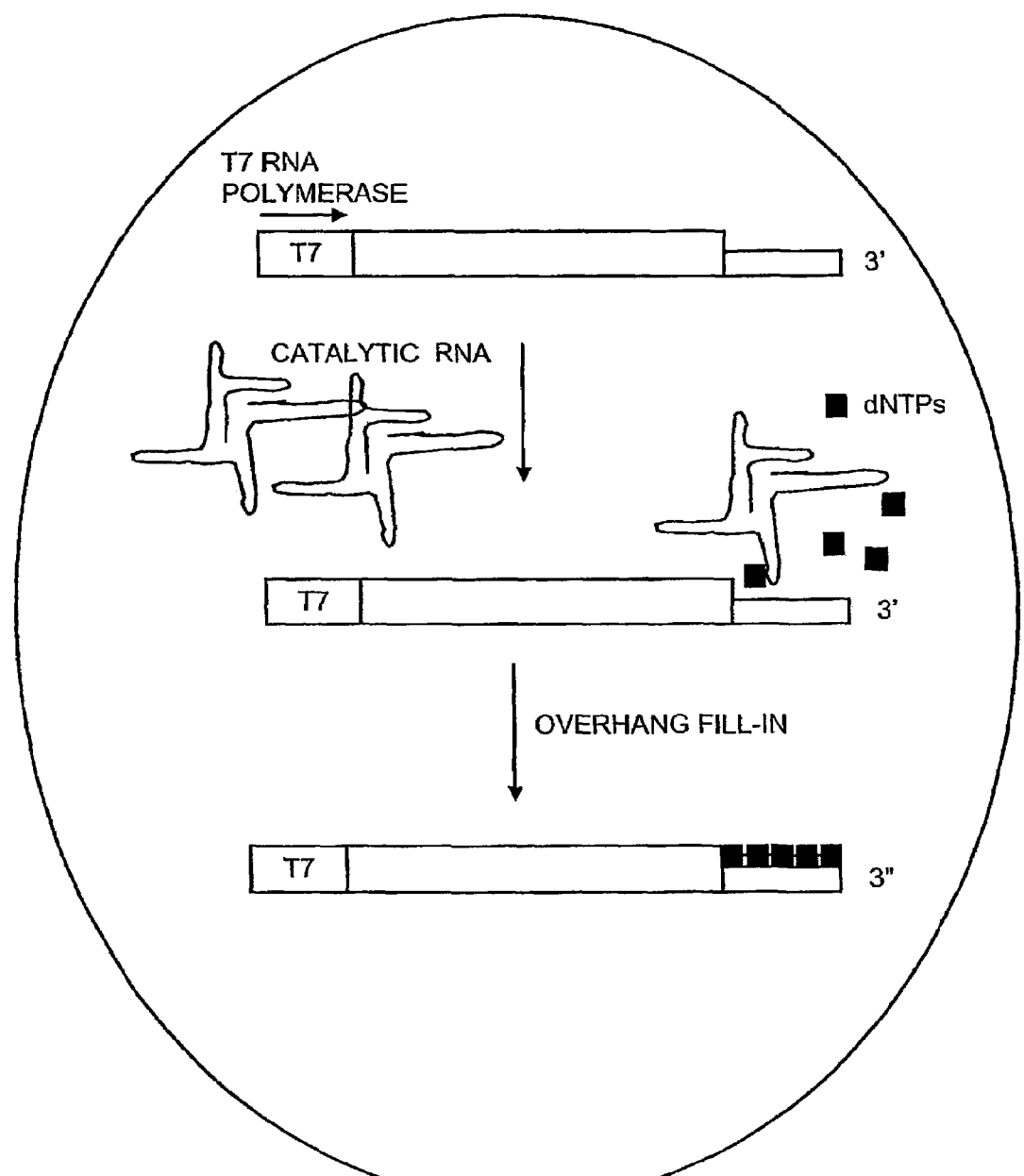
FIG. 6 is a diagram showing selection of RNA having (intermolecular) catalytic activity using the methods of our invention.

By creating a 5' overhang (e.g. by ligation of either DNA or RNA adaptors) in the emulsified gene, RNA variants are selected for with the ability of carrying out the template directed addition of successive dNTPs in trans (i.e. polymerase activity, see FIG. 6). Genes that have been "filled-in" may be rescued by PCR using primers complimentary to the single-stranded region of the gene (i.e., the region, which is single stranded prior to ribozyme fill-in) or by capture of biotin (or otherwise) modified nucleotides that are incorporated followed by PCR. In compartments without catalytic RNA activity, this region remains single stranded, and PCR will fail to amplify the template (alternatively no nucleotides are incorporated and the template is not captured but washed away).

A coupling approach can also be used to further extend the range of enzymatic activities that could be selected for. For example, co-emulsification of a DNA polymerase with the gene described above (5' overhang) can be used to select for ribozymes that convert an otherwise unsuitable NTP substrate into one that can be utilised by the polymerase. As before, the "filled-in" gene can then be rescued by PCR. The above approach can also be used to select for protein polymerase enzyme produced in-situ from a similar template (i.e. with 3' overhang). A diagram showing the selection of RNA having catalytic activity is shown as FIG. 6.

Selection of Agents Capable of Modifying Replicase Activity

In another embodiment, our invention is used to select for an agent capable of modifying the activity of a replicase. In this embodiment, a pool of nucleic acids is generated comprising members encoding one or more candidate agents. Members of the nucleic acid library are compartmentalised together with a replicase (which, as explained above, is able only to act on the nucleic acid encoding the agent).

The candidate agents may be functionally or chemically distinct from each other, or they may be variants of an agent known or suspected to be capable of modulating replicase activity. Members of the pool are then segregated into compartments together with the polypeptides or polynucleotides encoded by them, so that preferably each compartment comprises a single member of the pool together with its cognate encoded polypeptide. Each compartment also comprises one or more molecules of the replicase. Thus, the encoded polypeptide agent is able to modulate the activity of the replicase, to prevent or enhance replication of the compartmentalised nucleic acid (i.e., the nucleic acid encoding the agent). In this way, the polypeptide agent is able to act via the replicase to increase or decrease the number of molecules of its encoding nucleic acid. In a highly preferred embodiment of the invention, the agent is capable of enhancing replicase activity, to enable detection or selection of the agent by detecting the encoding nucleic acid.

The modulating agent may act directly or indirectly on the replicase. For example, the modulating agent may be an enzyme comprising an activity, which acts on the replicase molecule, for example, by a post-translational modification of replicase, to activate or inactivate the replicase. The agent may act by taking off or putting on a ligand from the replicase molecule. It is known that many replicases such as polymerases and ligases are regulated by phosphorylation, so that in preferred embodiments the agent according to the invention is a kinase or a phosphorylase. The modulating agent may also directly interact with the replicase and modify its properties (e.g. Thioredoxin & T7-DNA polymerase, members of the replisome e.g. clamp, helicase etc. with DNA polymerase III).

Alternatively, the modulating agent may exert its effects on the replicase in an indirect manner. For example, modulation of replicase activity may take place via a third body, which third body is modified by the modulating agent, for example as described above.

Furthermore, the modulating agent may be an enzyme, which forms part of a pathway, which produces as an end product a substrate for the replicase. In this embodiment, the modulating agent is involved in the synthesis of an intermediate (or the end product) of the pathway. Accordingly, the rate of replication (and hence the amount of nucleic acid encoding the agent) is dependent on the activity of the modulating agent.

For example, the modulating agent may be a kinase that is involved in the biosynthesis of bases, deoxyribonucleosides, deoxyribonucleotides such as dAMP, dCMP, dGMP and dTMP, deoxyribonucleoside diphosphates (such as dADP, dCDP, dCTP and dTDP), deoxyribonucleoside triphosphates such as dATP, dCTP, dGTP or dTTP, or nucleosides, nucleotides such as AMP, CMP, GMP and UMP, nucleoside diphosphates (such as ADP, CDP, CTP and UDP), nucleoside triphosphates such as ATP, CTP, GTP or UTP, etc. The modulating agent may be involved in the synthesis of other intermediates in the biosynthesis of nucleotides (as described and well known from biochemical textbooks such as Stryer or Lehninger), such as IMP, 5-phospho-α-D-ribose-1-pyrophosphoric acid, 5-phospho-β-D-ribossylamine, 5-phosphoribosyl-glycinamide, 5-phosphoribosyl-N-formylglycinamide, etc. Thus, the agent may comprise an enzyme such as ribosephosphate pyrophosphokinase, phosphoribosylglycinamide synthetase, etc. Other examples of such agents will be apparent to those skilled in the art. The methods of our invention allow the selection of such agents with improved catalytic activity.

In yet another embodiment, the modulator functions to "unblock" a constituent of the replication cocktail (primers, dNTP, replicase etc.). An example of a blocked constituent would be a primer or dNTP with a chemical moiety attached that inhibits the replicase used in the CSR cycle. Alternatively, the pair of primers used could be covalently tethered by a linking agent, with cleavage of the agent by the modulator allowing both primers to amplify its gene in the presence of supplemented replicase. An example of a linking agent would be a peptide nucleic acid (PNA). Additionally, by designing a large oligonucleotide that encodes a pair of primer sequences interspersed by target nucleotide sequence, novel site-specific restriction enzymes could be evolved. As before, the rate of replication (and hence the amount of nucleic acid encoding the agent) is dependent on the activity of the modulating agent. Alternatively the modulator can modify the 5' end a primer such that amplification products incorporating the primer can be captured by a suitable agent (e.g. antibody) and thus enriched and reamplified.

In a further embodiment, the scope of CSR may be further broadened to select for agents that are not necessarily thermostable. Delivery vehicles (e.g. $E.\ coli$) containing expression constructs that encode a secretable form of a modulator/replicase of interest are compartmentalised. Inclusion of an inducing agent in the aqueous phase and incubation at permissive temperature (e.g. 37° C.) allows for expression and secretion of the modulator/replicase into the compartment. Sufficient time is then allowed for the modulator to act in any of the aforementioned ways to facilitate subsequent amplification of the gene encoding it (e.g. consume an inhibitor of replication). The ensuing temperature change during the amplification process serves to rid the compartment of host cell enzymatic activities (that have up to this point been segregated from the aqueous phase) and release the encoding gene for amplification.

Thus, according to an embodiment of our invention, we provide a method of selecting a polypeptide involved in a pathway which has as an end product a substrate which is involved in a replication reaction ("a pathway polypeptide"), the method comprising the steps of: (a) providing a replicase; (b) providing a pool of nucleic acids comprising members each encoding a pathway polypeptide or a variant of the pathway polypeptide; (c) subdividing the pool of nucleic acids into compartments, such that each compartment comprises a nucleic acid member of the pool, the pathway polypeptide or variant encoded by the nucleic acid member, the replicase, and other components of the pathway; and (d) detecting amplification of the nucleic acid member by the replicase.

The Examples (in particular Example 19 and following Examples) show the use of our invention in the selection of nucleoside diphosphate kinase (NDP Kinase), which catalyses the transfer of a phosphate group from ATP to a deoxynucleoside diphosphate to produce a deoxynucleoside triphosphate.

In yet another embodiment, the modulating agent is such that it consumes an inhibitor of replicase activity. For example, it is known that heparin is an inhibitor of replicase (polymerase) activity. Our method allows the selection of a heparinase with enhanced activity, by compartmentalisation of a library of nucleic acids encoding heparinase or variants of this enzyme, in the presence of heparin and polymerase. Heparinase variants with enhanced activity are able to break down heparin to a greater extent or more rapidly, thus removing the inhibition of replicase activity within the compartment and allowing the replication of the nucleic acid within the compartment (i.e., the nucleic acid encoding that heparinase variant).

Selection of Interacting Polypeptides

The most important systems for the selection of protein-protein interactions are in vivo methods, with the most important and best developed being the yeast two-hybrid system (Fields and Song, 1989, *Nature* 340, 245-246). In this system and related approaches two hybrid proteins are generated: a bait-hybrid comprising protein X fused to a DNA-binding domain and a prey-hybrid comprising protein Y fused to a transcription activation domain with cognate interaction of X and Y reconstituting the transcriptional activator. Two other in vivo systems have been put forward in which the polypeptide chain of an enzyme is expressed in two parts fused to two proteins X and Y and in which cognate X-Y interaction reconstitutes function of the enzyme (Karimova, 1998, *Proc. Natl. Acad. Sci. USA* 95, 5752-6; Pelletier, 1999, *Nat. Biotechnol.* 17, 683-690) conferring a selectable phenotype on the cell.

It has recently been shown that Taq polymerase can be split in a similar way (Vainshtein et al., 1996, *Protein Science* 5, 1785). According to our invention, therefore, we provide a method of selecting a pair of polypeptides capable of stable interaction by splitting Taq polymerase or any enzyme or factor auxiliary to the polymerase reaction.

The method comprises several steps. The first step consists of providing a first nucleic acid and a second nucleic acid. The first nucleic acid encodes a first fusion protein comprising a first subdomain of a replicase (or other see above) enzyme fused to a first polypeptide, while the second nucleic acid encodes a second fusion protein comprising a second subdomain of a replicase (or other see above) enzyme fused to a second polypeptide. The two fusion proteins are such that stable interaction of the first and second replicase (or other see above) subdomains generates replicase activity (either directly or indirectly). At least one of the first and second nucleic acids (preferably both) is provided in the form of a pool of nucleic acids encoding variants of the respective first and/or second polypeptide(s).

The pool or pools of nucleic acids are then subdivided into compartments, such that each compartment comprises a first nucleic acid and a second nucleic acid together with respective fusion proteins encoded by the first and second nucleic acids. The first polypeptide is then allowed to bind to the second polypeptide, such that binding of the first and second polypeptides leads to stable interaction of the replicase subdomains to generate replicase activity. Finally, amplification of at least one of the first and second nucleic acids by the replicase is detected.

Our invention therefore encompasses an in vitro selection system whereby reconstitution of replicase function through the cognate association of two polypeptide ligands drives amplification and linkage of the genes of the two ligands. Such an in vitro two-hybrid system is particularly suited for the investigation of protein-protein interactions at high temperatures, e.g. for the investigation of the protenomes of thermophilic organisms or the engineering of highly stable interactions.

The system can also be applied to the screening and isolation of molecular compounds that promote cognate interactions. For example, compounds can be chemically linked to either primers or dNTPs and thus would only be incorporated into amplicons if promoting association. In order to prevent cross-over, such compounds would have to be released only after compartmentalisation has taken place, e.g. by coupling to microbeads or by inclusion into dissolvable microspheres.

Single Step and Multiple Step Selections

The selection of suitable encapsulation conditions is desirable. Depending on the complexity and size of the library to be screened, it may be beneficial to set up the encapsulation procedure such that 1 or less than 1 nucleic acids is encapsulated per microcapsule or compartment. This will provide the greatest power of resolution. Where the library is larger and/or more complex, however, this may be impracticable; it may be preferable to encapsulate or compartmentalise several nucleic acids together and rely on repeated application of the method of the invention to achieve sorting of the desired activity. A combination of encapsulation procedures may be used to obtain the desired enrichment.

Theoretical studies indicate that the larger the number of nucleic acids variants created the more likely it is that a molecule will be created with the properties desired (see Perelson and Oster, 1979, *J. Theor. Biol.* 81, 64570 for a description of how this applies to repertoires of antibodies). Recently it has also been confirmed practically that larger phage-antibody repertoires do indeed give rise to more antibodies with better binding affinities than smaller repertoires (Griffiths et al., 1994, *Embo. J.* 13, 3245-60). To ensure that rare variants are generated and thus are capable of being selected, a large library size is desirable. Thus, the use of optimally small microcapsules is beneficial.

In addition to the nucleic acids described above, the microcapsules or compartments according to the invention may comprise further components required for the replication reaction to take place. Other components of the system may for example comprise those necessary for transcription and/or translation of the nucleic acid. These are selected for the requirements of a specific system from the following: a suitable buffer, an in vitro transcription/replication system and/or an in vitro translation system containing all the necessary ingredients, enzymes and cofactors, RNA polymerase, nucleotides, nucleic acids (natural or synthetic), transfer RNAs, ribosomes and amino acids, and the substrates of the reaction of interest in order to allow selection of the modified gene product.

Buffer

A suitable buffer will be one in which all of the desired components of the biological system are active and will therefore depend upon the requirements of each specific reaction system. Buffers suitable for biological and/or chemical reactions are known in the art and recipes provided in various laboratory texts (Sambrook et al., 1989, Molecular cloning: a laboratory manual. Cold Spring Harbor Laboratory Press, New York).

In Vitro Translation

The replicase may be provided by expression from a suitable host as described elsewhere, or it may be produced by in vitro transcription/translation in a suitable system as known in the art.

The in vitro translation system will usually comprise a cell extract, typically from bacteria (Zubay, 1973, *Annu. Rev. Genet.* 7, 267-87; Zubay, 1980, *Methods Enzymol.* 65, 856-77; Lesley et al., 1991, *J. Biol. Chem.* 266(4), 2632-8; Lesley, 1995, *Methods Mol. Biol.* 37, 265-78), rabbit reticulocytes (Pelham and Jackson, 1976, *Eur. J. Biochem.* 67, 247-56), or wheat germ (Anderson et al., 1983, *Methods Enzymol.* 101, 635-44). Many suitable systems are commercially available (for example from Promega) including some which will allow coupled transcription/translation (all the bacterial systems and the reticulocyte and wheat germ TNT™ extract systems from Promega). The mixture of amino acids used may include synthetic amino acids if desired, to increase the possible number or variety of proteins produced in the library. This can be accomplished by charging tRNAs with artificial amino acids and using these tRNAs for the in vitro translation of the proteins to be selected (Ellman et al., 1991, *Methods Enzymol.* 202, 301-36; Beimer, 1994, *Trends Biotechnol.* 12, 158-63; Mendel et al., 1995, *Annu. Rev. Biophys. Biomol Struc.* 24,435-62). Particularly desirable may be the use of in vitro translation systems reconstituted from purified components like the PURE system (Shimizu et al., 2001, *Nat. Biotech.* 19, 751).

After each round of selection the enrichment of the pool of nucleic acids for those encoding the molecules of interest can be assayed by non-compartmentalised in vitro transcription/replication or coupled transcription-translation reactions. The selected pool is cloned into a suitable plasmid vector and RNA or recombinant protein is produced from the individual clones for further purification and assay.

The invention moreover relates to a method for producing a gene product, once a nucleic acid encoding the gene product has been selected by the method of the invention. Clearly, the nucleic acid itself may be directly expressed by conventional means to produce the gene product. However, alternative techniques may be employed, as will be apparent to those skilled in the art. For example, the genetic information incorporated in the gene product may be incorporated into a suitable expression vector, and expressed therefrom.

Compartments

As used here, the term "compartment" is synonymous with "microcapsule" and the terms are used interchangeably. The function of the compartment is to enable co-localisation of the nucleic acid and the corresponding polypeptide encoded by the nucleic acid. This is preferably achieved by the ability of the compartment to substantially restrict diffusion of template and product strands to other compartments. Any replicase activity of the polypeptide is therefore restricted to being exercised on a nucleic acid within the confines of a compartment, and not other nucleic acids in other compartments. Another function of compartments is to restrict diffusion of molecules generated in a chemical or enzymatic reaction that feed or unblock a replication reaction.

The compartments of the present invention therefore require appropriate physical properties to allow the working of the invention.

First, to ensure that the nucleic acids and polypeptides do not diffuse between compartments, the contents of each compartment must be isolated from the contents of the surrounding compartments, so that there is no or little exchange of the nucleic acids and polypeptides between the compartments over a significant timescale.

Second, the method of the present invention requires that there are only a limited number of nucleic acids per compartment, or that all members within a single compartment are clonal (i.e. identical). This ensures that the polypeptide encoded by and corresponding to an individual nucleic acid will be isolated from other different nucleic acids. Thus, coupling between nucleic acid and its corresponding polypeptide will be highly specific. The enrichment factor is greatest with on average one or fewer nucleic acid clonal species per compartment, the linkage between nucleic acid and the activity of the encoded polypeptide being as tight as is possible, since the polypeptide encoded by an individual nucleic acid will be isolated from the products of all other nucleic acids. However, even if the theoretically optimal situation of, on average, a single nucleic acid or less per compartment is not used, a ratio of 5, 10, 50, 100 or 1000 or more nucleic acids per compartment may prove beneficial in selecting from a large library. Subsequent rounds of selection, including renewed compartmentalisation with differing nucleic acid distribution, will permit more stringent selection of the nucleic acids. Preferably, on average there is a single nucleic acid clonal species, or fewer, per compartment.

Moreover, each compartment contains a nucleic acid; this means that whilst some compartments may remain empty, the conditions are adjusted such that, statistically, each compartment will contain at least one, and preferably only one, nucleic acid.

Third, the formation and the composition of the compartments must not abolish the function of the machinery for the expression of the nucleic acids and the activity of the polypeptides.

Consequently, any compartmentalisation system used must fulfil these three requirements. The appropriate system(s) may vary depending on the precise nature of the requirements in each application of the invention, as will be apparent to the skilled person.

Various technologies are available for compartmentalisation, for example, gas aphrons (Juaregi and Varley, 1998, *Biotechnol Bioeng.* 59, 471) and prefabricated nanowells (Huang and Schreiber, 1997, *Proc. Natl. Acad. Sci USA* 94, 25). For different applications, different compartment sizes and surface chemistries, as discussed in further detail below, may be desirable. For example, it may be sufficient to utilise diffusion limiting porous materials like gels or alginate (Draget et al., 1997, *Int. J. Macromol.* 21, 47) or zeolithe-type materials. Furthermore, where in-situ PCR or in-cell PCR is carried out, cells may be treated with a cross-linking fixative to form porous compartments allowing diffusion of dNTPs, enzymes and primers.

A wide variety of compartmentalisation or microencapsulation procedures are available (Benita, S., Ed. (1996). Microencapsulation: methods and industrial applications. Drugs and pharmaceutical sciences. Edited by Swarbrick, J. New York: Marcel Dekker) and may be used to create the compartments used in accordance with the present invention. Indeed, more than 200 microencapsulation or compartmentalisation methods have been identified in the literature (Finch, C. A., 1993, Encapsulation and controlled release. *Spec. Publ-R. Soc. Chem.* 138, 35).

These include membrane enveloped aqueous vesicles such as lipid vesicles (liposomes) (New, R. R. C., Ed. (1990). Liposomes: a practical approach. The practical approach series. Edited by Rickwood, D. & Hames, B. D. Oxford: Oxford University Press) and non-ionic surfactant vesicles (van Hal, D. A., Bouwstra, J. A. & Junginger, H. E. (1996). Nonionic surfactant vesicles containing estradiol for topical application. In Microencapsulation: methods and industrial applications (Benita, S., ed.), pp. 329-347. Marcel Dekker, New York.). These are closed-membranous capsules of single or multiple bilayers of non-covalently assembled molecules, with each bilayer separated from its neighbour by an aqueous compartment. In the case of liposomes the membrane is composed of lipid molecules; these are usually phospholipids but sterols such as cholesterol may also be incorporated into the membranes (New, R. R. C., Ed. (1990). Liposomes: a practical approach. The practical approach series. Edited by Rickwood, D. & Hames, B. D. Oxford: Oxford University Press). A variety of enzyme-catalysed biochemical reactions, including RNA and DNA polymerisation, can be performed within liposomes (Chakrabarti, 1994, *J. Mol. Evol.* 39, 555-9; Oberholzer, 1995, *Biochem. Biophys. Res. Commun.* 207, 250-7; Oberholzer, 1995, *Chem. Biol.* 2, 677-82; Walde, 1998, *Biotechnol. Bioeng.* 57, 216-219; Wick and Luisi, 1996, *Chem. Biol.* 3, 277-85).

With a membrane-enveloped vesicle system much of the aqueous phase is outside the vesicles and is therefore non-compartmentalised. This continuous, aqueous phase should be removed or the biological systems in it inhibited or destroyed (for example, by digestion of nucleic acids with DNase or RNase) in order that the reactions are limited to the compartmentalised microcapsules (Luisi et al., 1987, *Methods Enzymol.* 136, 188-216).

Enzyme-catalysed biochemical reactions have also been demonstrated in microcapsule compartments generated by a variety of other methods. Many enzymes are active in reverse micellar solutions (Bru and Walde, 1991, *Eur. J. Biochem.* 199, 95-103; Bru and Walde, 1993, *Biochem. Mol. Biol. Int.* 31, 685-92; Creagh et al., 1993, *Enzyme Microb. Technol.* 15, 383-92; Haber et al., 1993 UNABLE TO FIND; Kumar et al., 1989, *Biophys. J.* 55, 789-792; Luisi, P. L. and B., S.-H., 1987, Activity and conformation of enzymes in reverse micellar solutions. *Methods Enzymol.* 136(188), 188-216; Mao and Walde, 1991, *Biochem. Biophys. Res. Commun.* 178, 1105-1112; Mao, Q. and Walde, P., 1991, Substrate effects on the enzymatic activity of alpha-chymotrypsin in reverse micelles. *Biochem. Biophys. Res. Commun.* 178(3), 1105-12; Mao, 1992, *Eur. J. Biochem.* 208, 165-70; Perez, G. M., Sanchez, F. A. and Garcia, C. F., 1992, Application of active-phase plot to the kinetic analysis of lipoxygenase in reverse micelles. *Biochem. J*; Walde, P., Goto, A., Monnard, P.-A., Wessicken, M. and Luisi, P. L., 1994, Oparin's reactions revisited: enzymatic synthesis of poly(adenylic acid) in micelles and self-reproducing vesicles. *J. Am. Chem. Soc.* 116, 7541-7547; Walde, P., Han, D. and Luisi, P. L., 1993, Spectroscopic and kinetic studies of lipases solubilized in reverse micelles. Biochemistry 32, 4029-34; Walde, 1988, *Eur. J. Biochem.* 173, 401-9) such as the AOT-isooctane-water system (Menger, F. M. and Yamada, K., 1979, *J. Am. Chem. Soc.* 101, 6731-6734).

Compartments can also be generated by interfacial polymerisation and interfacial complexation (Whateley, T. L., 1996, Microcapsules: preparation by interfacial polymerisation and interfacial complexation and their applications. In Microencapsulation: methods and industrial applications (Benita, S., ed.), pp. 349-375. Marcel Dekker, New York). Microcapsule compartments of this sort can have rigid, non-permeable membranes, or semipermeable membranes. Semipermeable microcapsules bordered by cellulose nitrate membranes, polyamide membranes and lipid-polyamide membranes can all support biochemical reactions, including multienzyme systems (Chang, 1987, *Methods Enzymol.* 136, 67-82; Chang, 1992, *Artif. Organs* 16, 71-4; Lim, 1984, *Appl. Biochem. Biotechnol.* 10, 81-5). Alginate/polylysine compartments (Lim and Sun, 1980, *Science* 210, 908-10), which can be formed under very mild conditions, have also proven to be very biocompatible, providing, for example, an effective method of encapsulating living cells and tissues (Chang, 1992, *Artif. Organs* 16, 71-4; Sun, 1992, *ASAIO J.* 38, 125-7).

Non-membranous compartmentalisation systems based on phase partitioning of an aqueous environment in a colloidal system, such as an emulsion, may also be used.

Preferably, the compartments of the present invention are formed from emulsions; heterogeneous systems of two immiscible liquid phases with one of the phases dispersed in the other as droplets of microscopic or colloidal size (Becher, P. (1957) Emulsions: theory and practice. Reinhold, N.Y.; Sherman, P. (1968) Emulsion science. Academic Press, London; Lissant, K. J., ed. Emulsions and emulsion technology. Surfactant Science New York: Marcel Dekker, 1974; Lissant, K. J., ed. Emulsions and emulsion technology. Surfactant Science New York: Marcel Dekker, 1984).

Emulsions may be produced from any suitable combination of immiscible liquids. Preferably the emulsion of the present invention has water (containing the biochemical components) as the phase present in the form of finely divided droplets (the disperse, internal or discontinuous phase) and a hydrophobic, immiscible liquid (an "oil") as the matrix in which these droplets are suspended (the nondisperse, continuous or external phase). Such emulsions are termed "water-in-oil" (W/O). This has the advantage that the entire aqueous phase containing the biochemical components is compartmentalised in discrete droplets (the internal phase). The external phase, being a hydrophobic oil, generally contains none of the biochemical components and hence is inert.

The emulsion may be stabilised by addition of one or more surface-active agents (surfactants). These surfactants are termed emulsifying agents and act at the water/oil interface to prevent (or at least delay) separation of the phases. Many oils and many emulsifiers can be used for the generation of water-in-oil emulsions; a recent compilation listed over 16,000 surfactants, many of which are used as emulsifying agents (Ash, M. and Ash, I. (1993) Handbook of industrial surfactants. Gower, Aldershot). Suitable oils include light white mineral oil and non-ionic surfactants (Schick, 1966 not found) such as sorbitan monooleate (Span™ 80; ICI) and polyoxyethylene-sorbitan monooleate (Tween™ 80; ICI) or t-Octylphenoxy-polyethoxy-ethanol (Triton X-100).

The use of anionic surfactants may also be beneficial. suitable surfactants include sodium cholate and sodium taurocholate. Particularly preferred is sodium deoxycholate, preferably at a concentration of 0.5% w/v, or below. Inclusion of such surfactants can in some cases increase the expression of the nucleic acids and/or the activity of the polypeptides. Addition of some anionic surfactants to a non-emulsified reaction mixture completely abolishes translation. During emulsification, however, the surfactant is transferred from the aqueous phase into the interface and activity is restored. Addition of an anionic surfactant to the mixtures to be emulsified ensures that reactions proceed only after compartmentalisation.

Creation of an emulsion generally requires the application of mechanical energy to force the phases together. There are a variety of ways of doing this which utilise a variety of mechanical devices, including stirrers (such as magnetic stir-bars, propeller and turbine stirrers, paddle devices and whisks), homogenisers (including rotor-stator homogenisers, high-pressure valve homogenisers and jet homogenisers), colloid mills, ultrasound and "membrane emulsification" devices (Becher, P. (1957) Emulsions: theory and practice. Reinhold, N.Y.; Dickinson, E. (1994) In Wedlock, D. J. (ed.), Emulsions and droplet size control. Butterworth-Heinemann, Oxford, Vol. pp. 191-257).

Aqueous compartments formed in water-in-oil emulsions are generally stable with little if any exchange of polypeptides or nucleic acids between compartments. Additionally, it is known that several biochemical reactions proceed in emulsion compartments. Moreover, complicated biochemical processes, notably gene transcription and translation are also active in emulsion microcapsules. The technology exists to create emulsions with volumes all the way up to industrial scales of thousands of litres (Becher, P. (1957) Emulsions: theory and practice. Reinhold, N.Y.; Sherman, P. (1968) Emulsion science. Academic Press, London; Lissant, K. J., ed. Emulsions and emulsion technology. Surfactant Science New York: Marcel Dekker, 1974; Lissant, K. J., ed. Emulsions and emulsion technology. Surfactant Science New York; Marcel Dekker, 1984).

The preferred compartment size will vary depending upon the precise requirements of any individual selection process that is to be performed according to the present invention. In all cases, there will be an optimal balance between gene library size, the required enrichment and the required concentration of components in the individual compartments to achieve efficient expression and reactivity of the polypeptides.

The processes of expression may occur either in situ within each individual microcapsule or exogenously within cells (e.g. bacteria) or other suitable forms of subcompartmentalization. Both in vitro transcription and coupled transcription-translation become less efficient at sub-nanomolar DNA concentrations. Because of the requirement for only a limited number of DNA molecules to be present in each compartment, this therefore sets a practical upper limit on the possible compartment size where in vitro transcription is used. Preferably, for expression in situ using in vitro transcription and/or translation the mean volume of the compartments is less that $5.2\times10^{-16}$ m$^3$, (corresponding to a spherical compartment of diameter less than 1 μm).

An alternative is the separation of expression and compartmentalisation, e.g. using a cellular host. For inclusion of cells (in particular eucaryotic cells) mean compartment diameters of larger than 10 μM may be preferred.

Figure 2:
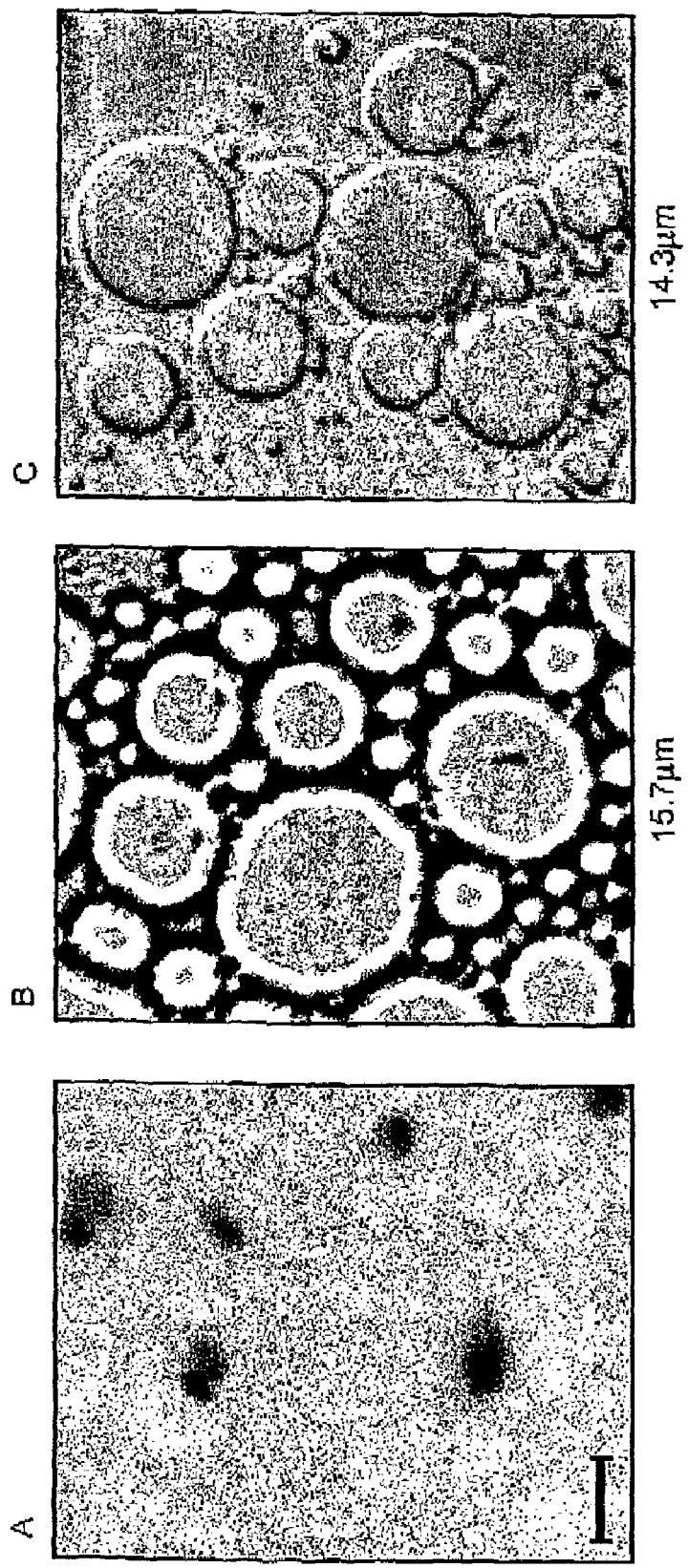
FIG. 2 is a diagram showing aqueous compartments of the heat-stable emulsion containing E. coli cells expressing green fluorescent protein (GFP) prior to (A, B), and after thermocycling (C), as imaged by light microscopy. (A, B) represent the same frame. (A) is imaged at 535 nm for GFP fluorescence and (B) in visible light to visualize bacterial cells within compartments. Smudging of the fluorescent bacteria in (A) is due to Brownian motion during exposure. Average compartment dimensions as determined by laser diffraction are given below.

As shown in the Examples, to colocalize the polymerase gene and encoded protein within the same emulsion compartment, we used bacteria (*E. coli*) overexpressing Taq polymerase as "delivery vehicles". *E. coli* cells (diameter 1-5 μM) fit readily into our emulsion compartments while leaving room for sufficient amounts of PCR reagents like nucleotide triphosphates and primers (as shown in FIG. 2). The denaturation step of the first PCR cycle ruptures the bacterial cell and releases the expressed polymerase and its encoding gene into the compartment allowing self-replication to proceed while simultaneously destroying background bacterial enzymatic activities. Furthermore, by analogy to hot-start strategies, this cellular "subcompartmentalization" prevents release of polymerase activity at ambient temperatures and the resulting non-specific amplification products.

The effective DNA or RNA concentration in the compartments may be artificially increased by various methods that will be well-known to those versed in the art. These include, for example, the addition of volume excluding chemicals such as polyethylene glycols (PEG) and a variety of gene amplification techniques, including transcription using RNA polymerases including those from bacteria such as *E. coli* (Roberts, 1969, *Nature* 224, 1168-74; Blattner and Dahlberg, 1972, *Nat. New. Biol.* 237, 227-32; Roberts et al., 1975, *J. Biol. Chem.* 250, 5530-41; Rosenberg et al., 1975, *J. Biol. Chem.* 250, 4755-4764), eukaryotes e.g. (Weil et al., 1979, *J. Biol. Chem.* 254, 6163-6173; Manley et al., 1983, *Methods Enzymol.* 101, 568-82) and bacteriophage such as T7, T3 and SP6 (Melton et al., 1984, *Nucleic Acids Res.* 12, 7035-56); the polymerase chain reaction (PCR) (Saiki et al., 1988, *Science* 239, 487-91); Qβ replicase amplification (Miele et al., 1983, *J. Mol. Biol.* 171, 281-95; Cahill et al., 1991, *Clin. Chem.* 37, 1482-5; Chetverin and Spirin, 1995, *Frog Nucleic Acid Res. Mol. Biol.* 51, 225-70; Katanaev et al., 1995, *FEBS Lett.* 359, 89-92); the ligase chain reaction (LCR) (Landegren et al., 1988, *Science* 241, 1077-80; Barany, 1991, *PCR Methods Appl.* 1, 5-16); and self-sustained sequence replication system (Fahy et al., 1991, *PCR Methods Appl.* 1, 25-33) and strand displacement amplification (Walker et al., 1992, *Nucleic Acids Res.* 20, 1691-6). Gene amplification techniques requiring thermal cycling such as PCR and LCR may also be used if the emulsions and the in vitro transcription or coupled transcription-translation systems are thermostable (for example, the coupled transcription-translation systems could be made from a thermostable organism such as *Thermus aquaticus*).

Increasing the effective local nucleic acid concentration enables larger compartments to be used effectively.

The compartment size must be sufficiently large to accommodate all of the required components of the biochemical reactions that are needed to occur within the compartment. For example, in vitro, both transcription reactions and coupled transcription-translation reactions require a total nucleoside triphosphate concentration of about 2 mM.

For example, in order to transcribe a gene to a single short RNA molecule of 500 bases in length, this would require a minimum of 500 molecules of nucleoside triphosphate per compartment ($8.33\times10^{-22}$ moles). In order to constitute a 2 mM solution, this number of molecules must be contained within a compartment of volume $4.17\times10^{-19}$ litres ($4.17\times10^{-22}$ m$^3$) which if spherical would have a diameter of 93 nm. Hence, the preferred lower limit for microcapsules is a diameter of approximately 0.1 μm (100 nm).

When using expression hosts as delivery vehicles, there are much less strict requirements on the compartment size. Basically, the compartment has to be of sufficient size to contain the expression host as well as sufficient amounts of reagents to carry out the required reactions. Thus, in such cases larger compartment sizes >10 μM are preferred. By an appropriate choice of vector used for expression in the host, the template concentration within compartments can be controlled via the vector origin and resulting copy number (e.g. *E. coli*: colE (pUC)>100, p15: 30-50, pSC101:1-4). Likewise the concentration of the gene product can be controlled by the amount by choice of expression promoter and expression protocol (e.g. full induction of expression versus promoter leakage). Preferably, gene product concentration is as high as possible.

Furthermore, the use of feeder compartments allows feeding of substrates from the outside (see Ghadessy et al., 2001, *PNAS* 98, 4552; 01). Feeding emulsion reactions from the outside may allow compartment dimensions <0.1 μM for ribozyme selections, as reagents do not need to be contained in their entirety within the compartment.

The size of emulsion microcapsules or compartments may be varied simply by tailoring the emulsion conditions used to form the emulsion according to requirements of the selection system. The larger the compartment size, the larger is the volume that will be required to encapsulate a given nucleic acid library, since the ultimately limiting factor will be the size of the compartment and thus the number of microcapsule compartments possible per unit volume.

The size of the compartments is selected not only having regard to the requirements of the replication system, but also those of the selection system employed for the nucleic acid.

Thus, the components of the selection system, such as a chemical modification system, may require reaction volumes and/or reagent concentrations, which are not optimal for replication. As set forth herein, such requirements may be accommodated by a secondary re-encapsulation step; moreover, they may be accommodated by selecting the compartment size in order to maximise replication and selection as a whole. Empirical determination of optimal compartment volume and reagent concentration, for example, as set forth herein, is preferred.

In a highly preferred embodiment of the present invention, the emulsion is a water-in-oil emulsion. The water-in-oil emulsion is made by adding an aqueous phase dropwise to an oil phase in the presence of a surfactant comprising 4.5% (v/v) Span 80, about 0.4% (v/v) Tween 80 and about 0.05-0.1% (v/v) Triton X100 in mineral oil preferably at a ratio of oil:water phase of 2:1 or 3:1. It appears that the ratio of the three surfactants is important for the advantageous properties of the emulsion, and accordingly, our invention also encompasses a water-in-oil emulsion having increased amounts of surfactant but with substantially the same ratio of Span 80, Tween 80 and Triton X100. In a preferred embodiment, the surfactant comprises 4.5% (v/v) Span 80, 0.4% (v/v) Tween 80 and 0.05% (v/v) Triton X100.

The water-in-oil emulsion is preferably formed under constant stirring in 2 ml round bottom biofreeze vials with continued stirring at 1000 rpm for a further 4 or 5 minutes after complete addition of the aqueous phase. The rate of addition may be up to 12 drops/mm (ca. 10 µl each). The aqueous phase may include just water, or it may comprise a buffered solution having additional components such as nucleic acids, nucleotide triphosphates, etc. In a preferred embodiment, the aqueous phase comprises a PCR reaction mix as disclosed elsewhere in this document, as well as nucleic acid, and polymerase. The water-in-oil emulsion may be formed from 200 µl of aqueous phase (for example PCR reaction mix) and 400 µl oil phase as described above.

The water-in-oil emulsion according to the invention has advantageous properties of increased thermal stability. Thus, no changes in compartment size or evidence of coalescence is observed after 20 cycles of PCR as judged by laser diffraction and light microscopy. This is shown in FIG. 2. In addition, polymerase chain reaction proceeded efficiently within the compartments of this water-in-oil composition, to approach the rates observed in solution PCR. Average aqueous compartment dimensions in the water-in-oil emulsion according to our invention are on average 15 µm in size. Once formed, the compartments of the emulsion according to our invention do not permit the exchange of macromolecules like DNA and proteins to any significant degree (as shown in FIG. 3A). This is presumably because the large molecular weight and charged nature of the macromolecules precludes diffusion across the hydrophobic surfactant shell, even at elevated temperatures.

Nucleic Acids

A nucleic acid in accordance with the present invention is as described above. Preferably, the nucleic acid is a molecule or construct selected from the group consisting of a DNA molecule, an RNA molecule, a partially or wholly artificial nucleic acid molecule consisting of exclusively synthetic or a mixture of naturally-occurring and synthetic bases, any one of the foregoing linked to a polypeptide, and any one of the foregoing linked to any other molecular group or construct. Advantageously, the other molecular group or construct may be selected from the group consisting of nucleic acids, polymeric substances, particularly beads, for example polystyrene beads, magnetic substances such as magnetic beads, labels, such as fluorophores or isotopic labels, chemical reagents, binding agents such as macrocycles and the like.

The nucleic acid may comprise suitable regulatory sequences, such as those required for efficient expression of the gene product, for example promoters, enhancers, translational initiation sequences, polyadenylation sequences, splice sites and the like.

The terms "isolating", "sorting" and "selecting", as well as variations thereof, are used herein. Isolation, according to the present invention, refers to the process of separating an entity from a heterogeneous population, for example a mixture, such that it is free of at least one substance with which it is associated before the isolation process. In a preferred embodiment, isolation refers to purification of an entity essentially to homogeneity. Sorting of an entity refers to the process of preferentially isolating desired entities over undesired entities. In as far as this relates to isolation of the desired entities, the terms "isolating" and "sorting" are equivalent. The method of the present invention permits the sorting of desired nucleic acids from pools (libraries or repertoires) of nucleic acids which contain the desired nucleic acid. Selecting is used to refer to the process (including the sorting process) of isolating an entity according to a particular property thereof.

"Oligonucleotide" refers to a molecule comprised of two or more deoxyribonucleotides or ribonucleotides, preferably more than three. The exact size of the oligonucleotide will depend on the ultimate function or use of the oligonucleotide. The oligonucleotide may be derived synthetically or by cloning.

The nucleic acids selected according to our invention may be further manipulated. For example, nucleic acid encoding selected replicase or interacting polypeptides are incorporated into a vector, and introduced into suitable host cells to produce transformed cell lines that express the gene product. The resulting cell lines can then be propagated for reproducible qualitative and/or quantitative analysis of the effect(s) of potential drugs affecting gene product function. Thus gene product expressing cells may be employed for the identification of compounds, particularly small molecular weight compounds, which modulate the function of gene product. Thus host cells expressing gene product are useful for drug screening and it is a further object of the present invention to provide a method for identifying compounds which modulate the activity of the gene product, said method comprising exposing cells containing heterologous DNA encoding gene product, wherein said cells produce functional gene product, to at least one compound or mixture of compounds or signal whose ability to modulate the activity of said gene product is sought to be determined, and thereafter monitoring said cells for changes caused by said modulation. Such an assay enables the identification of modulators, such as agonists, antagonists and allosteric modulators, of the gene product. As used herein, a compound or signal that modulates the activity of gene product refers to a compound that alters the activity of gene product in such a way that the activity of gene product is different in the presence of the compound or signal (as compared to the absence of said compound or signal).

Cell-based screening assays can be designed by constructing cell lines in which the expression of a reporter protein, i.e. an easily assayable protein, such as β galactosidase, chloramphenicol acetyltransferase (CAT) or luciferase, is dependent on gene product. Such an assay enables the detection of compounds that directly modulate gene product function, such as compounds that antagonise gene product, or compounds that inhibit or potentiate other cellular functions required for the activity of gene product.

The present invention also provides a method to exogenously affect gene product dependent processes occurring in cells. Recombinant gene product producing host cells, e.g. mammalian cells, can be contacted with a test compound, and the modulating effect(s) thereof can then be evaluated by comparing the gene product-mediated response in the presence and absence of test compound, or relating the gene product-mediated response of test cells, or control cells (i.e., cells that do not express gene product), to the presence of the compound.

Nucleic Acid Libraries

The method of the present invention is useful for sorting libraries of nucleic acids. Herein, the terms "library", "repertoire" and "pool" are used according to their ordinary signification in the art, such that a library of nucleic acids encodes a repertoire of gene products. In general, libraries are constructed from pools of nucleic acids and have properties, which facilitate sorting. Initial selection of a nucleic acid from a library of nucleic acids using the present invention will in most cases require the screening of a large number of variant nucleic acids. Libraries of nucleic acids can be created in a variety of different ways, including the following.

Pools of naturally occurring nucleic acids can be cloned from genomic DNA or cDNA (Sambrook et al., 1989, Molecular cloning: a laboratory manual. Cold Spring Harbor Laboratory Press, New York.); for example, phage antibody libraries, made by PCR amplification repertoires of antibody genes from immunised or unimmunised donors have proved very effective sources of functional antibody fragments (Winter et al., 1994, *Annu. Rev. Immunol.* 12, 433-55; Hoogenboom, H. R., 1997, *Trends Biotechnol.* 15, 62-70). Designing and optimizing library selection strategies for generating high-affinity antibodies. *Trends Biotechnol.* 15, 62-70; Hoogenboom, H. R., 1997, *Trends Biotechnol.* 15, 62-70). Libraries of genes can also be made by encoding all (see for example Smith, G. P., 1985, *Science* 228, 1315-7; Parmley, S. F. and Smith, G. P., 1988, *Gene* 73, 305-18) or part of genes (see for example Lowman et al., 1991, *Biochemistry* 30, 10832-8) or pools of genes (see for example Nissim, A., Hoogenboom et al., 1994, *Embo J.* 13, 692-8) by a randomised or doped synthetic oligonucleotide. Libraries can also be made by introducing mutations into a nucleic acids or pools of nucleic acids "randomly" by a variety of techniques in vivo, including: using "mutator strains" of bacteria such as *E. coli* mutD5 (Liao et al., 1986, *Proc. Natl. Acad. Sci. USA* 83, 576-80; Yamagishi et al., 1990, *Protein Eng.* 3, 713-9; Low et al., 1996, *J. Mol. Biol.* 260, 359-68); using the antibody hypermutation system of B-lymphocytes (Yelamos et al., 1995, *Nature* 376, 225-9). Random mutations can also be introduced both in vivo and in vitro by chemical mutagens, and ionising or UV irradiation (see Friedberg et al., 1995, DNA repair and mutagenesis. ASM Press, Washington D.C.), or incorporation of mutagenic base analogues (Freese, 1959, *J. Mol. Biol.* 1, 87; Zaccolo et al., 1996, *J. Mol. Biol.* 255, 589-603). "Random" mutations can also be introduced into genes in vitro during polymerisation for example by using error-prone polymerases (Leung et al., 1989, *Technique* 1, 11-15).

Further diversification can be introduced by using homologous recombination either in vivo (Kowalczykowski et al., 1994, *Microbiol. Rev.* 58, 401-65 or in vitro (Stemmer, 1994, *Nature* 370, 389-9.; Stemmer, 1994, *Proc. Natl. Acad. Sci. USA* 91, 10747-51).

Agent

As used herein, the term "agent" includes but is not limited to an atom or molecule, wherein a molecule may be inorganic or organic, a biological effector molecule and/or a nucleic acid encoding an agent such as a biological effector molecule, a protein, a polypeptide, a peptide, a nucleic acid, a peptide nucleic acid (PNA), a virus, a virus-like particle, a nucleotide, a ribonucleotide, a synthetic analogue of a nucleotide, a synthetic analogue of a ribonucleotide, a modified nucleotide, a modified ribonucleotide, an amino acid, an amino acid analogue, a modified amino acid, a modified amino acid analogue, a steroid, a proteoglycan, a lipid, a fatty acid and a carbohydrate. An agent may be in solution or in suspension (e.g., in crystalline, colloidal or other particulate form). The agent may be in the form of a monomer, dimer, oligomer, etc., or otherwise in a complex.

Polypeptide

As used herein, the terms "peptide", "polypeptide" and "protein" refer to a polymer in which the monomers are amino acids and are joined together through peptide or disulfide bonds. "Polypeptide" refers to either a full-length naturally-occurring amino acid chain or a "fragment thereof" or "peptide", such as a selected region of the polypeptide that binds to another protein, peptide or polypeptide in a manner modulatable by a ligand, or to an amino acid polymer, or a fragment or peptide thereof, which is partially or wholly non-natural. "Fragment thereof" thus refers to an amino acid sequence that is a portion of a full-length polypeptide, between about 8 and about 500 amino acids in length, preferably about 8 to about 300, more preferably about 8 to about 200 amino acids, and even more preferably about 10 to about 50 or 100 amino acids in length. "Peptide" refers to a short amino acid sequence that is 10-40 amino acids long, preferably 10-35 amino acids. Additionally, unnatural amino acids, for example, β-alanine, phenyl glycine and homoarginine may be included. Commonly encountered amino acids, which are not gene-encoded, may also be used in the present invention. All of the amino acids used in the present invention may be either the D- or L-optical isomer. The L-isomers are preferred. In addition, other peptidomimetics are also useful, e.g. in linker sequences of polypeptides of the present invention (see Spatola, 1983, in Chemistry and Biochemistry of Amino Acids, Peptides and Proteins, Weinstein, ed., Marcel Dekker, New York, p. 267). A "polypeptide binding molecule" is a molecule, preferably a polypeptide, protein or peptide, which has the ability to bind to another polypeptide, protein or peptide. Preferably, this binding ability is modulatable by a ligand.

The term "synthetic", as used herein, means that the process or substance described does not ordinarily occur in nature. Preferably, a synthetic substance is defined as a substance which is produced by in vitro synthesis or manipulation.

The term "molecule" is used herein to refer to any atom, ion, molecule, macromolecule (for example polypeptide), or combination of such entities. The term "ligand" may be used interchangeably with the term "molecule". Molecules according to the invention may be free in solution, or may be partially or fully immobilised. They may be present as discrete entities, or may be complexed with other molecules. Preferably, molecules according to the invention include polypeptides displayed on the surface of bacteriophage particles. More preferably, molecules according to the invention include libraries of polypeptides presented as integral parts of the envelope proteins on the outer surface of bacteriophage particles. Methods for the production of libraries encoding randomised polypeptides are known in the art and may be applied in the present invention. Randomisation may be total, or partial; in the case of partial randomisation, the selected codons preferably encode options for amino acids, and not for stop codons.

EXAMPLES

Example 1

Construction of Taq Polymerase Expression Plasmids

The Taq polymerase open reading frame is amplified by PCR from *Thermus aquaticus* genomic DNA using primers 1 & 2, cut with XhaI & SalI and ligated into pASK75 (Skerra A., 1994, *Gene* 151, 131) cut with XbaI & SalI. pASK75 is an expression vector which directs the synthesis of foreign proteins in *E. coli* under transcriptional control of the tetA promoter/operator.

Clones are screened for inserts using primers 3, 4 and assayed for expression of active Taq polymerase (Taq pol) (see below). The inactive Taq pol mutant D785H/E786V is constructed using Quickchange mutagenesis (Stratagene). The mutated residues are critical for activity (Doublie S. et al., 1998, *Nature* 391, 251; Kiefer J. R. et al., 1998, *Nature* 391, 304). Resulting clones are screened for mutation using PCR screening with primers 3, 5 and diagnostic digestion of the products with PmlI. Mutant clones are assayed for expression of active Taq pol (see below).

Example 2

Protein Expression and Activity Assay

Transformed TG1 cells are grown in 2×TY 0.1 mg/ml ampicillin. For expression, overnight cultures are diluted 1/100 into fresh 2×TY medium and grown to OD600=0.5 at 37° C. Protein expression is induced by addition of anhydro tetracycline to a final concentration of 0.2 µg/ml. After 4 hours further incubation at 37° C., cells are spun down, washed once, and re-suspended in an equal volume of 1× SuperTaq polymerase buffer (50 mM KCl, 10 mM Tris-HCl (pH 9.0), 0.1% Triton X-100, 1.5 mM MgCl$_2$) (HT Biotechnology Ltd, Cambridge UK).

Washed cells are added directly to a PCR reaction mix (2 µl per 30 µl reaction volume) comprising template plasmid (20 ng), primers 4 and 5 (1 µM each), dNTPs (0.25 mM), 1× SuperTaq polymerase buffer, and overlaid with mineral oil. Reactions are incubated for 10 min at 94° C. to release Taq pol from the cells and then thermocycled with 30 cycles of the profile 94° C. (1 min), 55° C. (1 min), 72° C. (2 min).

Example 3

Emulsification of Amplification Reactions

Emulsification of reactions is carried out as follows. 200 µl of PCR reaction mix (Taq expression plasmid (200 ng), primers 3 and 4 (1 µM each), dNTPs (0.25 mM), Taq polymerase (10 units) is added dropwise (12 drops/min) to the oil phase (mineral oil (Sigma)) in the presence of 4.5% (v/v) Span 80 (Fluka), 0.4% (v/v) Tween 80 (Sigma) and 0.05% (v/v) Triton X100 (Sigma) under constant stirring (1000 rpm) in 2 ml round bottom biofreeze vials (Costar, Cambridge Mass.). After complete addition of the aqueous phase, stirring is continued for a further 4 minutes. Emulsified mixtures are then transferred to 0.5 ml thin-walled PCR tubes (100 µl/tube) and PCR carried out using 25 cycles of the profile 94° C. (1 min), 60° C. (1 min), 72° C. (3 min) after an initial 5 min incubation at 94° C. Reaction mixtures are recovered by the addition of a double volume of ether, vortexing and centrifugation for 2 minutes prior to removal of the ether phase. Amplified product is visualised on by gel electrophoresis on agarose gels using standard methods (see for example J. Sambrook, E. F. Fritsch, and T. Maniatis, 1989, Molecular Cloning: A Laboratory Manual, Second Edition, Books 1-3, Cold Spring Harbor Laboratory Press).

For emulsification of whole cells expressing Taq polymerase, the protocol is modified in the following way: Taq expression plasmid and Taq polymerase in the reaction cocktail are omitted and instead 5×10$^8$ induced *E. coli* TG1 cells (harbouring the expressed Taq polymerase as well as the expression plasmid) are added together with the additive tetramethyl ammonium chloride (50 µM), and RNAse (0.05% w/v, Roche, UK). The number of PCR cycles is also reduced to 20.

Example 4

Self-Replication of the Full-Length wt Taq Gene

In order to test genotype-phenotype linkage during self-replication, we mixed cells expressing either wild-type Taq polymerase (wt Taq) or the poorly active (under the buffer conditions) Stoffel fragment (sf Taq) (F. C. Lawyer, et al., 1993, *PCR Methods Appl.* 2, 275-87) at a 1:1 ratio and subjected them to CSR either in solution or in emulsion. In solution the smaller sf Taq is amplified preferentially. However, in emulsion there is almost exclusive self-replication of the full-length wt Taq gene (FIG. 3B). The number of bacterial cells is adjusted such that the majority of emulsion compartments contain only a single cell. However, because cells are distributed randomly among compartments, it is unavoidable that a minor fraction will contain two or more cells. As compartments do not appear to exchange template DNA (FIG. 3A), the small amount of sf Taq amplification in emulsion is likely to originate from these compartments. Clearly, their abundance is low and, as such, unlikely to affect selections. Indeed, in a test selection, a single round of CSR is sufficient to isolate wt Taq clones from a 10$^6$-fold excess of an inactive Taq mutant.

Using error-prone PCR, we prepared two repertoires of random Taq mutants (L1 (J. P. Vartanian, M. Henry, S. Wain-Hobson, 1996, *Nucleic Acid Res.* 24, 2627-2631 (1996)) and L2 (M. Zaccolo, E. Gherardi, 1999, *J. Mol. Biol.* 285, 775-83)). Only 1-5% of L1 or L2 clones are active, as judged by PCR, but a single round of CSR selection for polymerase activity under standard PCR conditions increased the proportion of active clones to 81% (L1*) and 77% (L2*).

Example 5

Mutagenic PCR

Taq polymerase gene variants are constructed using two different methods of error-prone PCR.

The first utilises the nucleoside analogues dPTP and dLTP (Zaccolo et al., 1996, *J. Mol. Biol.* 255, 589-603). Briefly, a 3-cycle PCR reaction comprising 50 mM KCl, 10 mM Tris HCl (pH 9.0), 0.1% Triton X-100, 2 mM MgCl2, dNTPS (500 µM), dPTP (500 µM), dLTP (500 µM), 1 pM template DNA, primers 8 and 9 (1 µM each), Taq polymerase (2.5 units) in a total volume of 50 µl is carried out with the thermal profile 94° C. (1 min), 55° C. (1 min), 72° C. (5 min). A 2 µl aliquot is then transferred to a 100 µl standard PCR reaction comprising 50 mM KCl, 10 mM Tris-HCl (pH 9.0), 0.1% Triton X-100, 1.5 mM MgCl2, dNTPS (250 µM), primers 6 and 7 (1 µM each), Taq polymerase (2.5 units). This reaction is cycled 30× with the profile 94° C. (30 seconds), 55° C. (30 seconds), 72° C. (4 minutes). Amplified product is gel-purified, and cloned into pASK75 as above to create library L2.

The second method utilises a combination of biased dNTPs and MnCl$_2$ to introduce errors during PCR. The reaction mix comprises 50 mM KCl, 10 mM Tris-HCl (pH 9.0), 0.1% Triton X-100, 2.5 mM MgCl$_2$, 0.3 mM MnCl$_2$, 1 pM template DNA, dTTP, dCTP, dGTP (all 1 mM), dATP (100 µM) primers 8 and 9 (1 µM each) and Taq polymerase (2.5 units). This reaction is cycled 30× with the profile 94° C. (30 seconds), 55° C. (30 seconds), 72° C. (4 minutes), and amplified products cloned as above to create library L1.

Example 6

Selection Protocol

For selection of active polymerases, PCR reactions within emulsions are carried out as described above but using primers 8, 9. For selection of variants with increased thermostability, emulsions are preincubated at 99° C. for up to 7 minutes prior to cycling as above. For selection of variants with increased activity in the presence of the inhibitor heparin, the latter is added to concentrations of 0.08 and 0.16 units/µl and cycling carried out as above. Detailed protocols are set out in further Examples below.

Amplification products resulting from compartments containing an active polymerase are extracted from emulsion with ether as before and then purified by standard phenolchlofororm extraction. 0.5 volumes of PEG/MgCl$_2$ solution (30% v/v PEG 800, 30 mM MgCl$_2$) is next added, and after mixing centrifugation carried out at 13,000 RPM for 10 minutes at room temperature. The supernatant (containing unincorporated primers and dNTPs) is discarded and the pellet re-suspended in TE. Amplified products are then further purified on spin-columns (Qiagen) to ensure complete removal of primers. These products are then re-amplified using primers 6, 7 (which are externally nested to primers 8 and 9) in a standard PCR reaction, with the exception that only 20 cycles are used. Re-amplified products are gel-purified and re-cloned into pASK75 as above. Transformants are plated and colonies screened as below. The remainder are scraped into 2×TY/0.1 mg/ml ampicillin, diluted down to $OD_{600}=0.1$ and grown/induced as above for repetition of the selection protocol.

Example 7

Colony Screening Protocol

Colonies are picked into a 96 well culture dish (Costar), grown and induced for expression as above. For screening, 2 µl of cells are used in a 30 µl PCR reaction to test for activity as above in a 96 well PCR plate (Costar) using primers 4 and 5. A temperature gradient block is used for the screening of selectants with increased thermostability. Reactions are pre-incubated for 5 minutes at temperatures ranging from 94.5 to 99° C. prior to standard cycling as above with primers 4 and 5 or 3 and 4. For screening of heparin-compatible polymerases, heparin is added to 0.1 units/30 µl during the 96-well format colony PCR screen. Active polymerases are then assayed in a range of heparin concentrations ranging from 0.007 to 3.75 units/30 µl and compared to wild-type.

Example 8

Assay for Catalytic Activity of Polymerases $K_{cat}$ and $K_m$ (dTTP) are determined using a homopolymeric substrate (Polesky et al., 1990, *J. Biol. Chem.* 265: 14579-91). The final reaction mix (25 µl) comprises 1× SuperTaq buffer (HT Biotech), poly(dA).oligo(dT)(500 nM, Pharmacia), and variable concentrations of [$\alpha$-$^{32}$P]dTTP (approx. 0.01 Ci/mmole). The reaction is initiated by addition of 5 µl enzyme in 1× SuperTaq buffer to give a final enzyme concentrations between 1-5 nM. Reactions are incubated for 4 minutes at 72° C., quenched with EDTA as in example 14, and applied to 24 mm DE-81 filters. Filters are washed and activity measured as in example 14. Kinetic parameters are determined using the standard Lineweaver-Burke plot. Experiments using 50% reduced homopolymer substrate show no gross difference in incorporation of dTTP by polymerase, indicating it is present in sufficient excess to validate the kinetic analysis protocol used.

Example 9

Standard PCR in Aqueous Compartments Within an Emulsion

To establish whether conditions in the aqueous compartments present in an emulsion are permissive for catalysis, a standard reaction mix is emulsified and PCR carried out. This leads to amplification of the correct sized Taq polymerase gene present in the plasmid template, with yields sufficient yields to allow visualisation using standard agarose gel electrophoresis.

Example 10

Emulsification of *E. coli* expressing Taq Polymerase and Subsequent PCR to Amplify Polymerase Gene

*E. coli* cells expressing Taq polymerase are emulsified and PCR carried out using primers flanking the polymerase cassette in the expression vector. Emulsification of up to 5×10$^8$ cells (per 600 µl total volume) leads to discernible product formation as judged by agarose gel electrophoresis. The cells therefore segregate into the aqueous compartments where conditions are suitable for self-amplification of the polymerase gene by the expressed Taq polymerase. Similar emulsions are estimated to contain about 1×10$^{10}$ compartments per ml (Tawfik D. and Griffiths A. D., 1998, *Nature Biotech.* 16, 652). The large number of cells that can be emulsified allows for selection from diverse repertoires of randomised protein.

Example 11

Maintenance of Genotype-Phenotype Linkage in Emulsion

To be viable for a selection method, the majority of aqueous compartments in the emulsion should harbour a single cell, and the integrity of compartments should be maintained during thermal cycling. This is tested by including in the emulsion cells harbouring a competitor template distinguishable by its smaller size.

*E. coli* expressing Taq polymerase are co-emulsified with *E. coli* expressing the Stoffel fragment at a ratio of one to one. The, Stoffel fragment is poorly active under the conditions used in emulsion, and thus amplification of its expression cassette by the same primer pair used for Taq self-amplification is the result of co-compartmentalisation with a cell expressing active Taq polymerase or leakage of Taq polymerase between compartments. After PCR, the vast majority of products are found to correspond to the active Taq polymerase gene thus validating the premise of one cell per durable compartment (see FIG. 2, Ghadessy et al., 2001, *PNAS* 98, 4552).

Example 12

Test Selection of Active over Inactive Taq Polymerase

To demonstrate that the method can select for potentially rare variants, a 10$^6$ fold excess of cells expressing inactive polymerase over those expressing the active form are co-emulsified. After PCR and cloning of amplified product, a single expression screen using a 96 well format indicated a $10^4$ fold enrichment for the active polymerase.

Example 13

Directed Evolution of Taq Polymerase Variants with Increased Thermal Stability

Polymerases with increased thermostability are of potential practical importance, reducing activity loss during thermocycling and allowing higher denaturation temperatures for the amplification of GC rich templates. Thus, we first used the selection method of our invention for the directed evolution of Taq variants with increased thermostability, starting from preselected libraries (L1*, L2*) and progressively increasing the temperature and duration of the initial thermal denaturation. After 3 rounds of selection, we isolated T8 (Table 1), a Taq clone with an 11-fold longer half-life at 97.5° C. than the already thermostable wt Taq enzyme (Table 2), making T8 the most thermostable member of the Pol I family on record. Clones are screened and marked by a PCR assay. Briefly, 2 µl of induced cells are added to 30 µl PCR mix and amplification of a 0.4 kb fragment is assayed under selection conditions (e.g. increasing amounts of heparin). Thermostability and heparin resistance of purified His tagged wt and mutant Taq clones is determined as in Lawyer et al., 1993, *PCR Methods Appl.* 2, 275-287; Lawer et al., 1989, *J. Biol. Chem.* 264, 6427-37, using activated salmon sperm DNA and normalized enzyme concentrations. Mutations conferring thermostability to T8 (and to a majority of less thermostable mutants) cluster in the 5'-3' exonuclease domain (Table 1). Indeed, truncation variants of Taq polymerase (F. C. Lawyer et al., 1993, *PCR Methods Appl.* 2, 275-87; W. M. Barnes, 1992, *Gene* 112, 29-35) lacking the exonuclease domain show improved thermostability, suggesting it may be less thermostable than the main polymerase domain. The lower thermostability of the exonuclease domain may have functional significance (for example reflecting a need for greater flexibility), as the stabilizing mutations in T8 appear to reduce exonuclease activity (approx. 5-fold) (5'-3' exonuclease activity is determined essentially as in (Y. Xu et al., 1997, *J. Mol. Biol.* 268, 284-302) but in 1×Taq buffer with 0.25 mM dNTP's and the 22-mer oligonucleotide of (Y. Xu et al., 1997, *J. Mol. Biol.* 268, 284-302) 5' labelled with Cy5 (Amersham). Steady-state kinetics are measured as in A. H. Polesky, T. A. Steitz, N. D. Grindley, C. M. Joyce, 1990, *J. Biol. Chem.* 265, 14579-91, using the homopolymeric substrate poly(dA)$_{200}$ (Pharmacia) and oligo(dT)$_{40}$ primer at 50° C. (at least at low temperature).

TABLE 1

Properties of Selected Clones

| Round | Taq variant Taq$_{wt}$ | Thermo-stability* 1 | Heparin Resistance* 1 |
| --- | --- | --- | --- |
| 1 | T646 (G46V, A109P, F285L) | 2x | n.d. |
|   | T788 (F73S, R205K, K219E, M236T, A608V) | 4x | n.d. |
| 2 | T9 (F278L, P298S) | 4x | n.d. |
|   | T13 (R205K, K219E, M236T, A608V) | 7x | n.d. |
| 3 | T8 (F73S, R205K, K219E, M236T, E434D, A608V) | 11x | <0.5x |
| 1 | H32 (E9K, P93S, K340E, Q534R, T539A, V703A, R778K) | n.d. | 8x |
| 2 | H94 (K225E, L294P, A454S, L461R, D578G, N583S) | n.d. | 32x |
| 3 | H15 (K225E, E388V, K540R, D578G, N583S, M747R) | 0.3x | 130x |

*as judged by PCR (relative to Taq$_{wt}$), at 97.5° C.
**as judged by PCR (relative to Taq$_{wt}$)
Clones in bold are related through underlined mutations. Clones are ranked in relation to wt Taq.

Two libraries of Taq polymerase variants generated using error-prone PCR are expressed in *E. coli* (library L1, 8×10$^7$ clones, library L2, 2×10$^7$ clones; see example 5) and emulsified as before. The first round of PCR is carried out to enrich for active variants using the standard Taq polymerase thermocycling profile outlined above. Enriched amplification products are purified, and recloned to generate libraries comprising of active variants (L1*, L2*; approx. 10$^6$ clones for each library). A screen of the L1* and L2* libraries respectively showed 81% and 77% of randomly picked clones to be active.

Selective pressure is applied to the L1* and L2* libraries during the next round of PCR by pre-incubating emulsions at 99° C. for 6 or 7 minutes prior to the normal PCR cycle. Under these conditions, the wild-type Taq polymerase loses all activity. Amplified products are enriched and cloned as above and a 96-well expression screen used to select for active variants under normal PCR conditions. This yielded 7 clones form the L2* library and 10 clones from the L1* library. These are then screened for increased thermostability using a temperature gradient PCR block, with a 5 minute pre-incubation at temperatures of 94.5 to 99° C. prior to standard cycling. As judged by gel electrophoresis, 5 clones from each library are present with increased thermostability compared to wild-type. These mutants are able to efficiently amplify the 320 b.p. target after pre-incubation at 99° C. for 5 minutes. The wild-type enzyme has no discernible activity after pre-incubation at temperatures above 97° C. for 5 minutes or longer.

Example 14

Assay for Thermal Stability of Polymerase

Thermal inactivation assays of WT and purified His-tagged polymerases are carried out in a standard 50 µl PCR mixture comprising 1× SuperTaq buffer (HT Biotech), 0.5 ng plasmid DNA template, 200 µM each of dATP, dTTP, and dGTP, primers 3 and 4 (10 µM), and polymerase (approximately 5 nM). Reaction mixtures are overlaid with oil and incubated at 97.5° C., with 5 µl aliquots being removed and stored on ice after defined intervals. These aliquots are assayed in a 50 µl activity reaction buffer comprising 25 mM N-tris[hydroxymethyl-3-amino-propanesulfonic acid (TAPS)(pH 9.5), 1 mM β-mercaptoethanol, 2 mM MgCl2, 200 µM each dATP, dTTP, and dGTP, 100 µM[α-$^{32}$P]dCTP (0.05 Ci/mmole), and 250 µg/ml activated salmon sperm DNA template. Reactions are incubated for 10 minutes at 72° C., stopped by addition of EDTA (25 mM final). Reaction volumes are made up to 500 µl with solution S (2 mM EDTA, 50 ug/ml sheared salmon sperm DNA) and 500 µl 20% TCA (v/v) 12% sodium pyrophosphate (v/v) added. After 20 minutes incubation on ice, reactions are applied to 24 mm GF/C filters (Whatman). Unincorporated nucleotides are removed by 3 washes with 5% TCA (v/v), 2% sodium pyrophosphate (v/v) followed by two washes with 96% ethanol (v/v). Dried filters are counted in scintillation vials containing Ecoscint A (National Diagnostics). The assay is calibrated using a known amount of the labeled dCTP solution (omitting the washes).

Example 15

Directed Evolution of Taq Polymerase Variants with Increased Activity in the Presence of the Inhibitor Heparin As indicated above, the methods of our invention can also be used to evolve resistance to an inhibitor of enzymatic activity. Heparin is a widely used anticoagulant, but also a potent inhibitor of polymerase activity, creating difficulties for PCR amplifications from clinical blood samples (J. Satsangi, D. P. Jewell, K. Welsh, M. Bunce, J. I. Bell, 1994, *Lancet* 343, 1509-10). While heparin can be removed from blood samples by various procedures, these can be both costly and time-consuming. The availability of a heparin-compatible polymerase would therefore greatly improve characterisation of therapeutically significant amplicons, and obviate the need for possibly cost-prohibitive heparinase treatment of samples (Taylor A. C., 1997, *Mol Ecol.* 6, 383).

The L1* and L2* libraries are combined, and selected in emulsion for polymerases active in up to 0.16 units heparin per μl. After a single round, 5 active clones are isolated in the 96 well PCR screen incorporating 0.1 units/30 μl reaction, with the wild-type showing no activity. Titration shows that 4 of these clones to be active in up to four times the amount of heparin inhibiting wild-type (0.06 units/30 μl versus 0.015 units/30 μl). The other clone is active in up to eight times the amount of heparin inhibiting wild-type (0.12 units/30 μl versus 0.015 units/30 μl).

Figure 7:
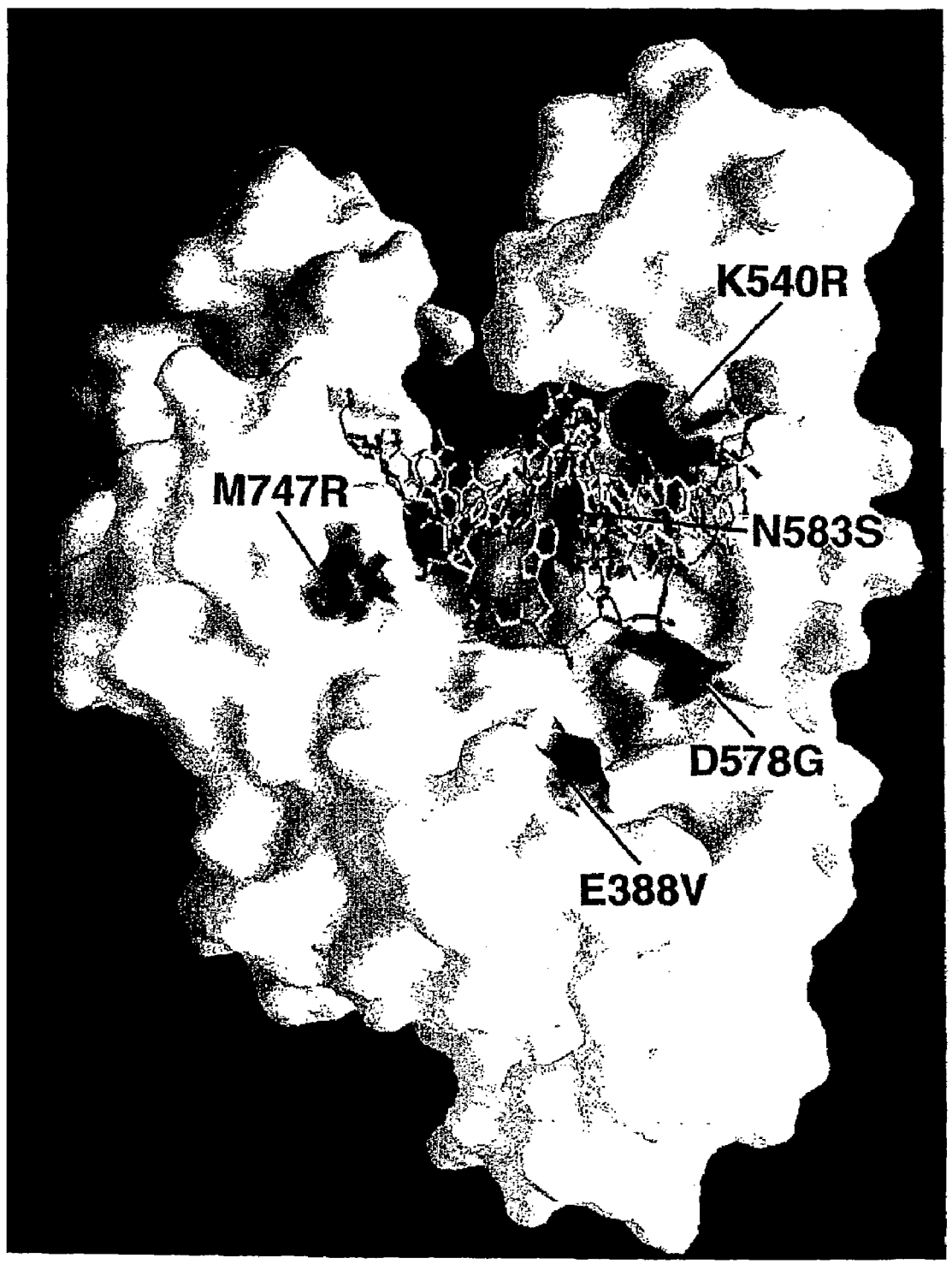
FIG. 7 is a diagram showing a model of a Taq-DNA complex.
Figure 8:
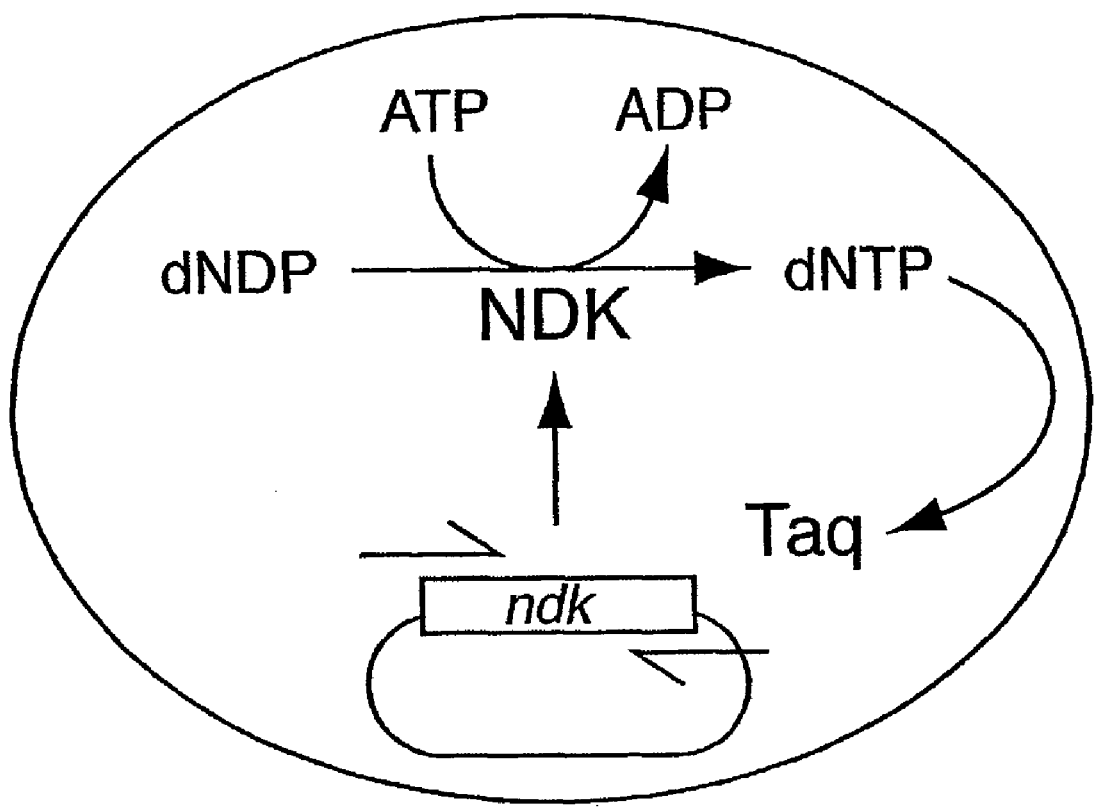
FIG. 8: A: General scheme of a cooperative CSR reaction.
Figure 8:
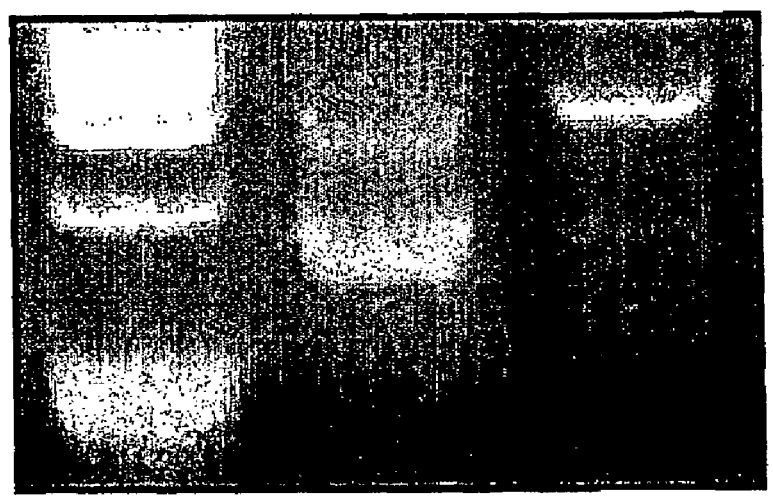

Using selection in the presence of increasing amounts of heparin, we isolated H15, a Taq variant functional in PCR at up to 130-times the inhibitory concentration of heparin (Table 2). Intriguingly, heparin resistance conferring mutations also cluster, in this case in the base of the finger and thumb polymerase subdomains, regions involved in binding duplex DNA. Indeed, judging from a recent high-resolution structure of a Taq-DNA complex (Y. Li, S. Korolev, G. Waksman, 1998, *EMBO J.* 17, 7514-25) four out of six residues mutated in H15 (K540, D578, N583, M747) directly contact either template or product strand (as shown in FIG. 7). H15 mutations appear to be neutral (or mutually compensating) as far as affinity for duplex DNA is concerned (while presumably reducing affinity for heparin) (Table 2) ($K_D$ for DNA is determined using BIAcore. Briefly, the 68-mer used in (M. Astatke, N. D. Grindley, C. M. Joyce, 1995, *J. Biol. Chem.* 270, 1945-54) is biotinylated at the 5' end and bound to a SA sensorchip and binding of polymerases is measured in 1×Taq buffer (see above) at 20° C. Relative $K_D$ values are estimated by the PCR ranking assay using decreasing amounts of template). The precise molecular basis of heparin inhibition is not known, but our results strongly suggest overlapping (and presumably mutually exclusive) binding sites for DNA and heparin in the polymerase active site, lending support to the notion that heparin exerts its inhibitory effect by mimicking and competing with duplex DNA for binding to the active site. Our observation that heparin inhibition is markedly reduced under conditions of excess template DNA, (see, Clones are screened and ranked by a PCR assay. Briefly, 2 μl of induced cells are added to 30 μl PCR mix and amplification of a 0.4 kb fragment is assayed under selection conditions (e.g. increasing amounts of heparin). Thermostability and heparin resistance of purified His tagged wt and mutant Taq clones is determined as in (F. C. Lawyer et al., 1993, *PCR Methods Appl.* 2, 275-87; F. C. Lawyer et al., 1989, *J. Biol. Chem.* 264, 6427-37) using activated salmon sperm DNA and normalized enzyme concentrations, Table 2) appears consistent with this hypothesis.

TABLE 2

Properties of Selected Taq Clones

| Taq clone | $T_{1/2}$ (97.5° C.) (min) | Heparin resistance (units/ml) | | $K_D$ (nM$^{-1}$) | $k_{cat}$ (s$^{-1}$) | $K_{M\text{-}dTTP}$ (μM) | 5'-3' exo activity | Mutation Rate$^§$ |
|---|---|---|---|---|---|---|---|---|
| Taq* | n.d. | n.d. | 0.6*** | 0.8$^†$ | 4.0$^‡$ | 43.2 | n.d. | 1.1 |
| Taq$_{wt}$ | 1.5** | 90** | 0.6*** | 0.8 | 9.0 | 45.0 | 1 | 1 |
| T8 | 16.5** | n.d. | 0.3*** | 1.2 | 8.8 | 48.6 | 0.2 | 1.2 |
| H15 | 0.3*** | 1750* | 84*** | 0.79 | 6.8 | 47.2 | 1.5 | 0.9 |

*commercial Taq preparation (HT Biotechnology),
**with N-terminal His$_6$ tag, measured by CTP$^{32}$ incorporation into salmon sperm DNA,
***no tag, measured by PCR assay, $^†$Taq, published value: 1nM$^{-1}$ (1), Klenow (Cambio), 4nM$^{-1}$,
$^‡$*E. coli* DNA Pol I, published value: 3.8 s$^{-1}$ (A. H. Polesky, T. A. Steitz, N. D. Grindley, C. M. Joyce, 1990, J. Biol. Chem. 265, 14579-91),
$^§$in relation to Taq$_{wt}$ measured by mutS ELISA (Genecheck) (P. Debbie et al., 1997, Nucleic Acids Res. 25, 4825-4829), Pfu (Stratagene): 0.2.

Example 16

Template Evolution in Emulsion Selection

A classic outcome of in vitro replication experiments is an adaptation of the template sequence towards more rapid replication (S. Spiegelman, 1971, *Q. Rev. Biophys.* 4, 213-253). Indeed, we also observe template evolution through silent mutations. Unlike the coding mutations (AT to GC vs. GC to AT/29 vs. 16), non-coding mutations display a striking bias (AT to GC vs. GC to AT/0 vs. 42) towards decreased GC content, generally thought to promote more efficient replication by facilitating strand separation and destabilizing secondary structures. Apart from selecting for adaptation, our method may also select for adaptability; i.e. polymerases might evolve towards an optimal, presumably higher, rate of self-mutation (M. Eigen, 1971, *Naturwissenschaften* 58, 465-

523). Indeed, mutators can arise spontaneously in asexual bacterial populations under adaptive stress (F. Taddei et al., 1997, *Nature* 387, 700-2; P. D. Sniegowski, P. J. Gerrish, R. E. Lenski, 1997, *Nature* 387, 703-5). By analogy, it could be argued that our method might favour polymerase variants that are more error-prone and hence capable of faster adaptive evolution. However, none of the selected polymerases displayed increased error rates (Table 2). Eliminating recombination and decreasing the mutational load during our method cycle may increase selective pressures towards more error-prone enzymes.

Example 17

Assay for Heparin Tolerance of Polymerases

Heparin tolerance of polymerases is assayed using a similar assay to that for thermal stability. Heparin is serially diluted into the activity buffer (0-320 units/45 µl) and 5 µl of enzyme in the standard PCR mixture above are added. Reactions are incubated and incorporation assayed as above.

Example 18

Selection for Taq Variants with Increased Ability to Extend from a 3' Mismatched Base The primers used are Primer 9 (LMB388ba5WA) and Primer 10 (8fo2WC). This primer combination presents polymerase variants with a 3' purine-purine mismatch (A-G), and a 3' pyrimidine-pyrimidine mismatch (C-C). These are the mismatches least tolerated by Taq polymerase (Huang et al., 1992, *Nucleic Acids Res.* 20(17), 4567-73) and are poorly extended.

The selection protocol is essentially the same as before, except that these two primers are used in emulsion. Extension time is also increased to 8 minutes. After two rounds of selection, 7 clones are isolated which display up to a 16-fold increase in extension off the mismatch as judged by a PCR ranking assay (see example 2: using primers 5 and 11) and standardised for activity using the normal primer pair. These clones are subsequently shuffled back into the original L1* and L2* libraries along with wild-type Taq and the selection process repeated, albeit with a lower number of cycles (10) during the CSR reaction. This round of selection yielded numerous clones, the best of which displayed up to 32-fold increase in mismatch extension as judged by PCR (see example 2) using primers 5 and 11.

Incorporation of an incorrect base pair by Taq polymerase can stall the polymerisation process as certain mismatches (see above) are poorly extended by Taq. As such, Taq polymerase alone cannot be used in the amplification of large (>6 Kb) templates (Barnes). This problem can be overcome by supplementing Taq with a polymerase that has a 3'-5' exonuclease activity (eg Pfu polymerase) that removes incorrectly incorporated bases and allows resumption of polymerisation by Taq. The clones above are therefore investigated for their ability to carry out amplification of large DNA fragments (long-distance PCR) from a lambda DNA template, as incorporation of an incorrect base would not be expected to stall polymerisation. Using primers 12 (LBA23) and 13 (LFO46) (1 uM each) in a 50 ul PCR reaction containing 3 ng lambda DNA (New England Biolabs) dNTPs (0.2 mM), 1×PCR buffer (HT Biotech) clone M1 is able to amplify a 23 Kb fragment using 20 repetitions of a 2-step amplification cycle (94° C., 15 seconds; 68° C., 25 minutes). Wild-type polymerase is unable to extend products above 13 kb using the same reaction buffer. Commercial Taq (Perkin Elmer) could not extend beyond 6 kb using buffer supplied by the manufacturer.

Example 19

Selection Using Self-Sustained Sequence Replication (3SR)

To demonstrate the feasibility of 3SR within emulsion, the Taq polymerase gene is first PCR-amplified from the parent plasmid (see example 1) using a forward primer that is designed to incorporate a T7 RNA polymerase promoter into the PCR product. A 250 µl 3SR reaction mix comprising the modified Taq gene (50 ng), 180 units T7 RNA polymerase (USB, 63 units reverse transcriptase (HT Biotech), rNTPs (12.5 mM), dNTPs (1 mM), $MgCl_2$ (10 mM), primer Taqba2T7 (primer 12; 125 pmoles), primer 88fo2 (primer 4; 125 pmoles), 25 mM Tris-HCl (pH 8.3), 50 mM KCl, and 2.0 mM DTT is made. 200 µl of this is emulsified using the standard protocol. After prolonged incubation at room temperature, amplification of the Taq gene (representing a model gene size) within emulsion is seen to take place as judged by standard gel-electrophoresis.

To further expand the scope of the method, the 3SR reaction is carried out in an in-vitro transcription/translation extract (EcoPro, Novagen). The inactive Taq gene (see example 1) is amplified from parental plasmid using primers 2 (TaqfoSal) and 12 (Taqba2T7). 100 ng (approx. $1 \times 10^{10}$ copies) is added to make up 100 ul of the aqueous phase comprising EcoPro extract (70 ul), methionine (4 ul), reverse transcriptase (84 units, HT Biotech), primer 12 (Taqba2T7, 2 uM), primer 13 (TaqfoLMB2, 2 uM), dNTPs (250 uM). The aqueous phase is emulsified into 400 ul oil-phase using the standard protocol. After incubation at 37° C. overnight, the emulsion is extracted using the standard protocol and the aqueous phase further purified using a PCR-purification column (Qiagen). Complete removal of primers is ensured by treating 5 µl of column eluate with 2 µl ExoZap reagent (Stratagene). DNA produced in emulsion by 3SR is rescued by using 2 µl of treated treated column eluate in an otherwise standard 50 ul PCR reaction using 20 cycles of amplification and primers 6 (LMB, ref 2) and 12 (Taqba2T7). Compared to background (the control reaction where reverse transcriptase is omitted from the 3SR reaction in emulsion), a more intense correctly sized band could be seen when products are visualised using agarose gel electrophoresis. The 3SR reaction can therefore proceed in the transcription/translation extracts, allowing for the directed evolution of agents expressed in aqueous compartments.

WT Taq polymerase has limited reverse transcriptase activity (Perler et al., 1996, *Adv. Protein Chem.* 48, 377-435). It is also known that reverse transcriptases (eg HIV reverse transcriptase that has both reverse transcriptase and polymerase activities) are considerably more error prone than other polymerases. This raises the possibility that a more error-prone polymerase (where increased tolerance for non-cognate substrate is evident) might display increased reverse transcriptase activity. The genes for Taq variants M1, M4 as well as the inactive mutant are amplified from parental plasmids using primers 12 (Taqba2T7) and 2 (TaqfoSal) and the 3SR reaction is carried out as above in the transcription/translation extract (Novagen) with the exception that reverse transcriptase is not exogenously added. In control reactions, methionine is omitted from the reaction mix. After 3 hours incubation at 37° C., the reaction is treated as above and PCR carried out using primer pair 6 and 12 to rescue products synthesised during the 3SR reaction. Of the clones tested, clone M4 gave a more intense correctly sized band compared to control reaction when products are visualised using agarose gel electrophoresis. Clone M4 would therefore appear to possess some degree of reverse transcriptase activity. This result shows that it is possible to express functionally active replicases in vitro. When coupled to selection by compartmentalisation, novel replicases could be evolved.

Selection of Agents Modifying Replicase Activity

Example 19 and the following Examples describes how the methods of our invention may be employed to select an enzyme which is involved in a metabolic pathway whose final product is a substrate for the replicase. These Examples show a method for selection of nucleoside diphosphate kinase (NDP Kinase), which catalyses the transfer of a phosphate group from ATP to a deoxynucleoside diphosphate to produce a deoxynucleoside triphosphate (dNTP). Here, the selectable enzyme (NDK) provides substrates for Taq polymerase to amplify the gene encoding it. This selection method differs from the compartmentalized self-replication of a replicase (CSR, Ghadessy and Holliger) in that replication is a coupled process, allowing for selection of enzymes (nucleic acids and protein) that are not replicases themselves. Bacteria expressing NDK (and containing its gene on an expression vector) are co-emulsified with its substrate (in this case, dNDPs and ATP) along with the other reagents needed to facilitate its amplification (Taq polymerase, primers specific for the ndk gene, and buffer). Compartmentalization in a water-in-oil emulsion ensures the segregation of individual library variants. Active clones provide the dNTPs necessary for Taq polymerase to amplify the ndk gene. Variants with increased activity provide more substrate for its own amplification and hence post-selection copy number correlates to enzymatic activity within the constraints of polymerase activity. Additional selective pressure arises from the minimum amount of dNTPs required for polymerase activity, hence clones with increased catalytic activity are amplified preferentially at the expense of poorly active variants (selection is for $k_{cat}$ as well as $K_m$).

By showing that we can evolve an enzyme whose product feeds into the polymerase reaction, we hope to eventually co-evolve multiple enzymes linked through a pathway where one enzyme's product is substrate for the next. Diversity could be introduced into two or more genes, and both genes could be co-transformed into the same expression host on plasmids or phage. We hope to develop cooperative enzyme systems that enable selection for the synthesis of unnatural substrates and their subsequent incorporation into DNA.

Example 20

Induced Expression of NDP Kinase in Bacterial Cells

A pUC19 expression plasmid containing the EcoRI/HindIII restriction fragment with the open reading frame of Nucleoside Diphosphate Kinase from Myxococcus Xanthus is cloned. Plasmid is prepared from an overnight culture and transformed into the ndk-, pykA-, pykF-strain of E. coli QL1387. An overnight culture of QL1387/pUC19ndk is grown in the presence of chloramphenicol (10 µg/ml final concentration), ampicillin (100 µg/ml final concentration) and glucose (2%) for 14-18 hours. The overnight culture is diluted 1:100 in (2XTY, 10 µg/ml chloramphenicol, 100 µg/ml anipicillin and 0.1% glucose). Cells are grown to an O.D. (600 nm) of 0.4 and induced with IPTG (1 mM final concentration) for 4 hours at 37° C. After protein induction, cells are washed once in SuperTaq buffer (10 mM tris-HCL pH 9, 50 mM KCl, 0.1% Triton X-100, 1.5 mM MgCl2, HT Biotechnology) and resuspended in $\frac{1}{10}$ volume of the same buffer. The number of cells is quantified by spectrophotometric analysis with the approximation of O.D.600 $0.1=1\times10^8$ cells/ml.

Example 21

Phosphoryl Transfer Reaction in Aqueous Compartments Within an Emulsion

To establish whether deoxynucleoside diphosphates can be phosphorylated by NDP kinase in Taq buffer, a standard PCR reaction is carried out in which dNTPs are replaced by dNDPs and ATP, a donor phosphate molecule. Nucleoside diphosphate kinase is expressed from E. coli QL1387 (a ndk and pyruvate kinase deficient strain of E. coli) as described in the previous example. Cells are mixed with the PCR reaction mix.

Washed cells are added to a PCR reaction mixture (approx. 8e5 cells/µl final concentration) containing SuperTaq buffer, 0.5 µM primers, 100 µM each dNDP, 400 µM ATP, SuperTaq polymerase (0.1 unit/µl final concentration, HT Biotechnology).

After breaking open the cells at 65° C. for 10 min, incubating the reaction mixture for 10 minutes at 37° C., and thermocycling (15 cycles of 94° C. 15 sec, 55° C. 30 sec, 72° C. 1 min 30 sec), amplified products are visualized on a standard 1.5% agarose/TBE gel stained with ethidium bromide (Sambrook). The results of this experiment show that expressed NDP kinase can phosphorylate dNDPs to provide Taq polymerase with substrates for the PCR amplification of the ndk gene.

The experiment is repeated, with the additional step of emulsifying the reaction mixture with mineral oil and detergent as described above. It is found that NDP kinase is active within aqueous compartments of an emulsion.

Example 22

Compartmentalization of NDK Variants by Emulsification

The original emulsion mix allowed for the diffusion of small molecules between compartments during thermocycling. However, by adjusting the water to oil ratio and minimizing the thermocycling profile, the exchange of product and substrate between compartments is minimized, resulting in a tighter linkage of genotype to phenotype. Given the diffusion rates can be controlled by modifying the emulsion mix, it may be possible to adjust buffer conditions after emulsification, possibly allowing for greater control of selection conditions (i.e. adjusting pH with the addition of acid or base, or starting/stopping reactions with the addition of substrates or inhibitors).

150 µl of PCR reaction mix (SuperTaq buffer, 0.5 µM each primer, 100 µM each dNDP, 400 µM ATP, 0.1 unit/µl Taq polymerase, $8\times10^5$ cells/µl of QL1387/ndk) are added dropwise (1 drop/5 sec) to 450 µl oil phase (mineral oil) in the presence of 4.5% v/v Span 80, 0.4% v/v Tween 80 and 0.05% v/v Triton X-100 under constant stirring in a 2 ml round bottom biofreeze vial (Corning). After addition of the aqueous phase, stirring is continued for an additional 5 minutes. Emulsion reactions are aliquoted (100 µl) into thin-walled PCR tubes and thermocycled as indicated above.

Recovery of amplified products after emulsification is carried out as follows. After thermocycling, products are recovered by extraction with 2 volumes of diethyl ether, vortexed, and centrifuged for 10 minutes in a tabletop microfuge. Amplification products are analyzed as before.

Example 23

Minimizing Background Kinase Activity

Background kinase activity levels are determined by emulsifying E. coli TG1 cells in Taq buffer with substrates, as described above. It is found that native nucleoside diphosphate kinase from E. coli retained enough activity after the initial denaturation to provide significant kinase activity in our assay. The pUC19 expression plasmid containing the ndk gene is transformed into a ndk deficient strain of E. coli QL1387. Compared to a catalytic knockout mutant of mx ndk (H117A), the background kinase activity is determined to be negligible in our assay (amplified products could not be visualized by agarose gel electrophoresis) when ndk is expressed from the knockout strain.

Example 24

Maintenance of the Genotype-Phenotype Linkage in Emulsion

A catalytic knockout mutation (NDK H117A) of NDP kinase is co-emulsified with wild-type NDP kinase in equal amounts. The inactive mutant of ndk is distinguished by a smaller amplification product, since the 5' and 3' regions flanking the ORF downstream from the priming sites are removed during construction of the knockout mutant. Our emulsification procedure gives complete bias towards amplification of the active kinase, as determined by agarose gel electrophoresis.

Example 25

Method for the Parallel Genotyping of Heterogenous Populations of Cells

The approach involves compartmentation of the cells in question in the emulsion (see WO9303151) together with PCR reagents etc. and polymerase. However, instead of linking genes derived from one cell by PCR assembly, one (or several) biotinylated primers are used as well as a streptavidin coated polystyrene beads (or any other suitable means of linking primers onto beads). Thus, PCR fragments from one single cell are transferred to a single bead. Beads are pooled, interrogated for presence of a certain mutation or allele using fluorescently labelled probes (as described for "Digital PCR") and counted by FACS. Multiplex PCR allows the simultaneous interrogation of 10 or maybe more markers. Single beads can also be sorted for sequencing.

Applications include, for example, diagnosis of asymptomatic tumors, which hinge on the detection of a very small number of mutant cells in a large excess of normal cells. The advantage of this method over cytostaining is through-put. Potentially $10^8$-$10^9$ cells can be interrogated simultaneously.

Example 25

Short-Patch CSR

The present example relates to the selection of polymerases with low catalytic activity or processivity. Compartmentalized Self-Replication (CSR), as described, is a method of selecting polymerase variants with increased adaptation to distinct selection conditions. Mutants with increased catalytic activity have a selective advantage over ones that are less active under the selection conditions. However, for many selection objectives (e.g. altered substrate specificity) it is likely that intermediates along the evolutionary pathway to the new phenotype will have lowered catalytic activity. For example, from kinetic studies of E. coli DNA polymerase I, mutations such as E710A increased affinity and incorporation of ribonucleotides at the expense of lower catalytic rates and less affinity for wild-type substrates (deoxyribonucleotides) (F. B. Perler, S. Kumar, H. Kong, 1996, *Adv. in Prot. Chem.* 48, 377-430). The corresponding mutant of Taq DNA polymerase I, E615A, could incorporate ribonucleotides into PCR products more efficiently than wild-type polymerase. However, using wild-type substrates, it is only able to synthesize short fragments and not the full-length Taq gene, as analyzed by agarose gel electrophoresis. Therefore it would be difficult to select for this mutation by CSR. In another selection experiment in which Beta-glucuronidase is evolved into a β-galactosidase, the desired phenotype is obtained after several rounds of selection but at the expense of catalytic activity. It is also found that selected variants in the initial rounds of selection are able to catalyze the conversion of several different substrates not utilized by either parental enzyme, and at much lower catalytic rates (T. A. Steitz, 1999, *J. Biol. Chem.* 274, 17395-8).

In order to address the problem of being able to select polymerase variants with low catalytic activity or processivity such as may occur along an evolutionary trajectory to a desired phenotype, a variant of CSR, in which only a small region (a "patch") of the gene under investigation is randomized and replicated, is employed. The technique is referred to as "short-patch CSR" (spCSR). spCSR allows for less active or processive polymerases to still become enriched during a round of selection by decreasing the selective advantage given to highly active or processive mutants. This method expands on the previously described method of compartmentalized self-replication, but, because the entire gene is not replicated, the short patch method is also useful for example for investigating specific domains independent of the rest of the protein.

There are many ways to introduce localised diversity into a gene, among these are error-prone PCR (using manganese or synthetic bases, as described above for the Taq polymerase library), DNA shuffling (C. A. Brautigani, T. A. Steitz, 1998, *Curr. Opin. Struct. Biol.* 8, 54-63; Y. Li, S. Korolev, G. Waksman, 1998, *EMBO J.* 17, 7514-25), cassette mutagenesis (E. Bedford, S. Tabor, C. C. Richardson, 1997, *Proc. Natl. Acad. Sci. USA* 94, 479-84), and degenerate oligonucleotide directed mutagenesis (Y. Li, V. Mitaxov, G. Waksman, 1999, *Proc. Natl. Acad. Sci. USA* 96, 9491-6; M. Suzuki, D. Baskin, L. Hood, L. A. Loeb, 1996, *Proc. Natl. Acad. Sci. USA* 93, 9670-5) and its variants, e.g. sticky feet mutagenesis (J. L. Jestin, P. Kristensen, G. Winter, 1999, *Angew. Chem. Int. Ed.* 38, 1124-1127), and random mutagenesis by whole plasmid amplification (T. Oberholzer, M. Aibrizio, P. L. Luisi, 1995, *Chem. Biol.* 2, 677-82). Combinatorial alanine scanning (A. T. Haase, E. F. Retzel, K. A. Staskus, 1990, *Proc. Natl. Acad. Sci. USA* 87, 4971-5) may be used to generate library variants to determine which amino acid residues are functionally important.

Structural (M. J. Embleton, G. Gorochov, P. T. Jones, G. Winter, 1992, *Nucleic Acids Res.* 20, 3831-7), sequence alignment (D. S. Tawfik, A. D. Griffiths, 1998, *Nat. Biotechnol.* 16, 652-656), and biochemical data from DNA polymerase I studies reveal regions of the gene involved in nucleotide binding and catalysis. Several possible regions to target include regions 1 through 6, as discussed in D. S. Tawfik, A. D. Griffiths, 1998, *Nat. Biotechnol.* 16, 652-656 (regions 3, 4, and 5 are also referred to as Motif A, B, and C, respectively, in Taq DNA polymerase I). Other possible targeted regions would be those regions conserved across several diverse species, those implicated by structural data to contact the nucleotide substrate or to be involved in catalysis or in proximity to the active site, or any other region important to polymerase function or substrate binding.

During a round of selection, each library variant is required to replicate only the region of diversity. This can be easily achieved by providing primers in a PCR reaction which flank the region diversified. CSR selections would be done essentially as described. After CSR selection the short region which is diversified and replicated now is reintroduced into the starting gene (or another genetic framework e.g. a library of mutants of the parent gene, a related gene etc.) using either appropriately situated restriction sites or PCR recombination methods like PCR shuffling or Quickchange mutagenesis etc. The spCSR cycle may be repeated many times and multiple regions could be targeted simultaneously or iteratively with flanking primers either amplifying individual regions separately or inclusively.

To increase stringency in selections at a later stage spCSR is tunable simply by increasing the length of replicated sequence as defined by the flanking primers up to full length CSR. Indeed, for selection for processivity i.a. it may be beneficial to extend the replicated segment beyond the encoding gene to the whole vector using strategies analogous to iPCR (inverted PCR).

spCSR can have advantages over full length CSR not only when looking for polymerase variants with low activities or processivities but also when mapping discrete regions of a protein for mutability, e.g. in conjunction with combinatorial alanine scanning (A. T. Haase, E. F. Retzel, K. A. Staskus, 1990, *Proc. Natl. Acad. Sci. USA* 87, 4971-5) to determine which amino acid residues are functionally important. Such information may be useful at a later stage to guide semi-rational approaches, i.e. to target diversity to residues/regions not involved in core polymerase activity. Furthermore spCSR may be used to transplant polypeptide segments between polymerases (as with immunoglobulin CDR grafting). A simple swap of segments may lead initially to poorly active polymerases because of steric clashes and may require "reshaping" to integrate segments functionally. Reshaping may be done using either full length CSR (e.g. from existing random mutant libraries) or spCSR targeted to secondary regions ("Vernier zone" in antibodies).

Short patches may also be located at either N-or C-terminus as extensions to existing polymerase gene sequences or as internal insertions. Precedents for such phenotype modifying extensions and insertions exist in nature. For example both a C-terminal extension of T5 DNA pol and the thioredoxin-binding insertion in T7 DNA pol are critical for processivity in these enzymes and enable them to efficiently replicate the large (>30 kb) T-phage genomes. N-or C-terminal extensions have also been shown to enhance activity in other enzymes.

Example 26

Low Temperature CSR Using Klenow Fragment

Klenow fragment was cloned from *E. coli* genomic DNA into expression vector pASK75 (as with Taq) and expressed in *E. coli* strain DH5αZ1 (Lutz R. and Bujard H., 1997, *Nucleic Acids Res.* 25, 1203). Cells were washed and resuspended in 10 mM Tris pH 7.5. $2 \times 10^8$ resuspended cells (20 µl) were added to 200 µl low temperature PCR buffer (LTP) (Iakobashvili, R. and Lapidot, A., 1999, *Nucleic Acids Res.* 27, 1566) and emulsified as described (Ghadessy et al., 2001, *PNAS* 98, 4552). LTP was 10 mM Tris (pH 7.5), 5.5M L-proline, 15% w/v glycerol, 15 mM MgCl2+ suitable primers (because proline lowers melting temperature, primers need to be 40-mers or longer) and dNTP's and emulsified as described. Low temperature PCR cycling was 70° C. 10 min, 50× (70° C. 30 sec, 37° C. 12 min). Aqueous phase was extracted as described and puried selection products reamplified as described (Ghadessy et al., 2001, *PNAS* 98, 4552).

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are apparent to those skilled in molecular biology or related fields are intended to be within the scope of the following claims.

TABLE 3

Primer Sequences Used in Examples

| Primer | Designation | Sequence (5' to 3') |
|---|---|---|
| Primer 1 (SEQ ID NO: 1) | TaqbaXba | GGCGACTCTAGATAACGAGGGCAAAAAAT GCGTGGTATGCTTCCTCTTTTTGAGCCCA AGGG |
| Primer 2 (SEQ ID NO: 2) | TaqfoSal | GCGGTGCGGAGTCGACTCACTCCTTGGCG GAGAGCCAGTCCTC |
| Primer 3 (SEQ ID NO: 3) | 88ba4 | AAAAATCTAGATAACGAGGGCAA |
| Primer 4 (SEQ ID NO: 4) | 88fo2 | ACCACCGAACTGCGGGTGACGCCAAGCG |
| Primer 5 (SEQ ID NO: 5) | Taqba(scr) | GGGTACGTGGAGACCCTCTTCGGCC |
| Primer 6 (SEQ ID NO: 6) | LMB2 | GTAAAACGACGGCCAGT |
| Primer 7 (SEQ ID NO: 7) | LMB3 | CAGGAAACAGCTATGAC |
| Primer 8 (SEQ ID NO: 8) | 88ba4LMB3 | CAGGAAACAGCTATGACAAAAATCTAGAT AACGAGGGCAA |
| Primer 9 (SEQ ID NO: 9) | 88fo2LMB2 | GTAAAACGACGGCCAGTACCACCGAACTG CGGGTGACGCCAAGCG |
| Primer 10 (SEQ ID NO: 10) | LMB388ba5 WA | CAG GAA ACA GCT ATG ACA AAA ATC TAG ATA ACG AGG G<u>A</u> (A-G mismatch) |
| Primer 11 (SEQ ID NO: 11) | 8fo2WC | GTA AAA CGA CGG CCA GTA CCA CCG AAC TGC GGG TGA CGC CAA GC<u>C</u> (C-C mismatch) |
| Primer 12 (SEQ ID NO: 12) | LBA23 | GGAGTAGATGCTTGCTT TTCTGAGCC |
| Primer 13 (SEQ ID NO: 13) | LF046 | GCTCTGGT TATCTGCATC ATCGTCTGCC |

The invention claimed is:

1. A method of selecting an active nucleic acid replicase, the method comprising the steps of: (a) providing a pool of nucleic acids comprising nucleic acid members each encoding a nucleic acid replicase; (b) subdividing the pool of nucleic acids into compartments, such that each compartment comprises a nucleic acid member and the contents of each compartment are not in contact with the contents of other compartments; (c) expressing the nucleic acid member in the compartment to form the nucleic acid replicase encoded by said nucleic acid member; (d) providing conditions within the compartment under which the nucleic acid member may be processed by the nucleic acid replicase encoded by said nucleic acid member; and (e) detecting processing of the nucleic acid member by the nucleic acid replicase encoded by said nucleic acid member, whereby an active nucleic acid replicase is selected.

2. The method of claim 1, wherein the processing of the nucleic acid member results in one copy of said nucleic acid member.

3. The method of claim 1, wherein the processing of the nucleic acid member comprises either a fill-in reaction of a 5' overhang appended to said nucleic acid member or an extension of a 3' end of said nucleic acid member.

4. The method of claim 1 in which the processing of the nucleic acid member results in more than one copy of said nucleic acid member.

5. The method of claim 4, in which the processing of the nucleic acid member is an exponential amplification.

6. The method of claim 4, in which the processing is carried out by a polymerase chain reaction (PCR), a nested PCR, a ligase chain reaction (LCR), a transcription based amplification system (TAS), a self-sustaining sequence replication (3SR), nucleic acid sequence-based amplification (NASBA), a transcription-mediated amplification reaction (TMA), or a strand-displacement amplification (SDA).

7. The method of claim 4, wherein the number of copies of the nucleic acid member is proportional to the activity of the nucleic acid replicase.

8. The method of claim 4, in which the processing is detected by assaying the copy number of the nucleic acid member.

9. The method of claim 4, in which the processing is detected by assaying the presence of a tag on the nucleic acid member.

10. The method of claim 4, in which the processing is detected by determining the nucleic acid replicase activity of the polypeptide encoded by the nucleic acid member.

11. The method of claim 1, in which the conditions in the compartment are selected to permit selection of a active nucleic acid replicase with a particular desired property.

12. The method of claim 4, in which the replicase activity of the nucleic acid replicase is a template-dependent replicase activity selected from a polymerase activity, a reverse transcriptase activity and a ligase activity.

13. The method of claim 1, wherein the step of expressing the nucleic acid member to form the nucleic acid replicase encoded by said nucleic acid member is carried out by in vitro transcription and translation.

14. The method of claim 1, wherein the step of expressing the nucleic acid member to form the nucleic acid replicase encoded by said nucleic acid member is carried out by in vivo transcription and translation in an expression host cell.

15. The method of claim 14 wherein said expression host cell is a bacterial cell.

16. The method of claim 1, in which the compartments comprise aqueous compartments of a water-in-oil emulsion.

17. The method of claim 16, in which the water-in-oil emulsion is produced by emulsifying an aqueous phase with an oil phase and a surfactant comprising Span80, Tween80, and TritonX100.

18. The method of claim 17 wherein said surfactant comprises 4.5% v/v Span80, 0.4% v/v Tween80 and 0.1% v/v TritonX100.

19. The method of claim 1 wherein the active nucleic acid replicase that is selected is a variant of a Taq polymerase which has greater thermostability than said Taq polymerase.

20. The method of claim 1 wherein the active nucleic acid replicase that is selected is a variant of a Taq polymerase which is inhibited to a lesser extent by heparin than is said Taq polymerase.

* * * * *